United States Patent
Banerjee et al.

(10) Patent No.: US 10,340,027 B2
(45) Date of Patent: Jul. 2, 2019

(54) IDENTIFICATION OF MULTI-MODAL ASSOCIATIONS BETWEEN BIOMEDICAL MARKERS

(75) Inventors: Nilanjana Banerjee, Armonk, NY (US); Angel Janevski, New York, NY (US); Sitharthan Kamalakaran, Pelham, NY (US); Vinay Varadan, New York, NY (US); Nevenka Dimitrova, Pelham Manor, NY (US); Robert Lucito, East Meadow, NY (US)

(73) Assignee: Koninklijke Philips N.V., Eindhoven (NL)

( * ) Notice: Subject to any disclaimer, the term of this patent is extended or adjusted under 35 U.S.C. 154(b) by 969 days.

(21) Appl. No.: 13/877,346

(22) PCT Filed: Oct. 4, 2011

(86) PCT No.: PCT/IB2011/054366
§ 371 (c)(1),
(2), (4) Date: Apr. 2, 2013

(87) PCT Pub. No.: WO2012/046191
PCT Pub. Date: Apr. 12, 2012

(65) Prior Publication Data
US 2013/0196877 A1    Aug. 1, 2013

Related U.S. Application Data

(60) Provisional application No. 61/391,111, filed on Oct. 8, 2010.

(51) Int. Cl.
*G01N 33/48* (2006.01)
*G16B 25/00* (2019.01)
*G16B 5/00* (2019.01)
*G06G 7/58* (2006.01)
*G16B 20/00* (2019.01)

(52) U.S. Cl.
CPC .............. *G16B 25/00* (2019.02); *G16B 5/00* (2019.02); *G16B 20/00* (2019.02)

(58) Field of Classification Search
None
See application file for complete search history.

(56) References Cited

U.S. PATENT DOCUMENTS

| 2006/0019256 A1 | 1/2006 | Clarke |
| 2009/0011049 A1 | 1/2009 | Van Criekinge et al. |
| 2010/0273674 A1 | 10/2010 | Kamalakaran |

FOREIGN PATENT DOCUMENTS

| CN | 1852974 A | 10/2006 |
| CN | 101039951 A | 9/2007 |
| WO | 2009037635 A2 | 3/2009 |

OTHER PUBLICATIONS

Horvath, S. Dong, J. (2008) "Geometric Interpretation of Gene Coexpression Network Analysis". PLoS Comput Biol 4(8): e1000117. doi: 10.1371/journal.pcbi.1000117.
Helleman, J, Smid, M. Jansen, M.P., Van Der Burg, M.E., Berns, E.M. (2010) "Pathway analysis of gene lists associated with platinum-based chemotherapy resistance in ovarian cancer: the big picture". Gynecologic Oncology, vol. 117, issue 2, pp. 170-176. Rotterdam, The Netherlands.
Banerjee, et al., "Pathway and network analysis probing epigenetic influences on chemosensitivity in ovarian cancer", Genomic Signal Processing and Statistics (GENSIPS), 2010 IEEE International Workshop, Nov. 10-12, 2010, pp. 1-4.

*Primary Examiner* — Eric S Dejong

(57) ABSTRACT

The present invention relates to a method for identifying multi-modal associations between biomedical markers which allows for the determination of network nodes and/or high ranking network members or combinations thereof, indicative of having a diagnostic, prognostic or predictive value for a medical condition, in particular ovarian cancer. The present invention further relates to a biomedical marker or group of biomedical markers associated with a high likelihood of responsiveness of a subject to a cancer therapy, preferably a platinum based cancer therapy, wherein said biomedical marker or group of biomedical markers comprises at least 1, 2, 3, 4, 5, 6, 7, 8, 9, 10, 11, 12, 13, 14, 15, 16, 17, 8, 19, 20 or all markers selected from PKMYT1, SKIL, RAB8A, HIRIP3, CTNNB1, NGFR, ZCCHC11, LSP1, CD200, PAX8, CYBRD1, HOXC11, TCEAL1, FZD10, FZD1, BBS4, IRS2, TLX3, TSPAN2, TXN, and CFLAR. Furthermore, an assay for detecting, diagnosing, graduating, monitoring or prognosticating a medical condition, or for detecting, 1 diagnosing, monitoring or prognosticating the responsiveness of a subject to a therapy against said medical condition, in particular ovarian cancer, is provided, as well as a corresponding method for classifying a subject comprising and a medical decision support system.

10 Claims, 4 Drawing Sheets

Specification includes a Sequence Listing.

SEQUENCE LISTING

```
<160> NUMBER OF SEQ ID NOS: 34

<210> SEQ ID NO 1
<211> LENGTH: 2121
<212> TYPE: DNA
<213> ORGANISM: Homo sapiens

<400> SEQUENCE: 1
tggaattttt ggcgcgagca gctccgcgcg cgttcacggg ccgttccccc tcacgggagt      60
cctccgcccg ggcgtccgga acagtcgacg gcagactccg gcccgctgag ccacccgagg     120
ggtcccgtgg cctccgcgga cccggaatct gggccctcgc ggaccgcgc cccgcccagt      180 cgccccaggg cttccccaca cccacggagt gaagtcagcc gcggccctgc ctgggaggaa     240
cttaccgtct accgggaaag gtggccagca gatgtgtcgg gcctggtgag agggtgaggc     300
gagacggccc gatcgcccag ggccccggaa gctgcggagg tcaccccgc ctggccttag      360 ctcagggaca ccctggattc acgtgggagc ccctgctcct gcctccccg tcccaccact      420 gaggctgttg ggccaggcca gtcatgctag aacggcctcc tgcactggcc atgcccatgc     480
ccacggaggg caccccgcca cctctgagtg gcacccccat cccagtccca gcctacttcc     540
gccacgcaga acctggattc tccctcaaga ggcccagggg gctcagccgg agcctcccac     600
ctccgccccc tgccaagggc agcattccca tcagccgcct cttccctcct cggacccag      660 gctggcacca gctgcagccc cggcgggtgt cattccgggg cgaggcctca gagactctgc     720
agagccctgg gtatgaccca agccggccag agtccttctt ccagcagagc ttccagaggc     780
tcagccgcct gggccatggc tcctacggag aggtcttcaa ggtgcgctcc aaggaggacg     840
gccggctcta tgcggtaaag cgttccatgt caccattccg gggccccaag gacgggccc      900 gcaagttggc cgaggtgggc agccacgaga aggtggggca gcacccatgc tgcgtgcggc     960
tggagcaggc ctgggaggag ggcggcatcc tgtacctgca gacggagctg tgcgggccca    1020
gcctgcagca acactgtgag gcctggggtg ccagcctgcc tgaggcccag gtctgggct     1080 acctgcggga cacgctgctt gccctggccc atctgcacag ccagggcctg gtgcacctg     1140 atgtcaagcc tgccaacatc ttcctggggc cccggggccg ctgcaagctg ggtgacttcg    1200
gactgctggt ggagctgggt acagcaggag ctggtgaggt ccaggaggga gaccccgct     1260 acatggcccc cgagctgctg cagggctcct atgggacagc agcggatgtg ttcagtctgg    1320
gcctcaccat cctggaagtg gcatgcaaca tggagctgcc ccacgtggg gagggctggc    1380 agcagctgcg ccagggctac ctgcccctg agttcactgc cggtctgtct tccgagctgc    1440
gttctgtcct tgtcatgatg ctggagccag accccaagct gcgggccacg gccgaggccc    1500
tgctggcact gcctgtgttg aggcagccgc gggcctgggg tgtgctgtgg tgcatggcag    1560
cggaggccct gagccgaggg tgggccctgt ggcaggccct gcttgccctg ctctgctggc    1620
tctggcatgg gctggctcac cctgccagct ggctacagcc cctgggcccg ccagccaccc    1680
cgcctggctc accaccctgc agtttgctcc tggacagcag cctctccagc aactgggatg    1740
```

| | |
|---|---:|
| acgacagcct agggccttca ctctcccctg aggctgtcct ggcccggact gtggggagca | 1800 |
| cctccacccc ccggagcagg tgcacaccca gggatgccct ggacctaagt gacatcaact | 1860 |
| cagagcctcc tcgggctcc ttcccctcct ttgagcctcg gaacctcctc agcctgtttg | 1920 |
| aggcaccccta gacccaacc tgagccccag actctgcctc tgcacttttta acctttatc | 1980 |
| ctgtgtctct cccgtcgccc ttgaaagctg gggcccctcg ggaactccca tggtcttctc | 2040 |
| tgcctggccg tgtctaataa aaagtatttg aaccttggga gcacccaagc ttgctcatgt | 2100 |
| ggcaaaaaaa aaaaaaaaa a | 2121 |

<210> SEQ ID NO 2
<211> LENGTH: 3526
<212> TYPE: DNA
<213> ORGANISM: Homo sapiens

<400> SEQUENCE: 2

| | |
|---|---:|
| gatgtgtgtg gggttcggag ccgcgccggc acagccgaag ggagcgggcg agcggcgacg | 60 |
| gcggcggcgg cgggcacaga ttaattaaaa gaagaatgaa ctataatcct tgaagataac | 120 |
| tgggcaattt tttaagtcgg aggctgttct tactggtgtg aggatttaca cacgtcttca | 180 |
| gttttttcagc acagaccagc agaccatcat ttttagagga aatactccct ctgccctcct | 240 |
| ttttggtttc cttggtggta aagattaaat ttggttgcat cattttgact tgtgtttgag | 300 |
| tctagatttt atggcacaag gaatggcata aacttttcat gtgttttggt taaacaaac | 360 |
| cagaccattg cattgaccct ggacatcttt aattgagaaa ttggtaactt tattttaata | 420 |
| tgtatatctg aagaattcaa gaaaacaaag gcatcctcag aggtgtgcct cttttctttta | 480 |
| ttattagagg caaaacgaac aattttatag gatttgtagt gaaattatac cagattataa | 540 |
| ggagaaccaa aactaagtcg caaaatttat taatttaagg ggctctcgct ttgaaagttt | 600 |
| gagagtaagt tacgataggc atttgtatcc attcattact ttcctctttt caaataagca | 660 |
| actaaataga aatgctaatc tcagacttaa ttatttaaca gaagagtgta ccatggaaaa | 720 |
| cctccagaca aatttctcct tggttcaggg ctcaactaaa aaactgaatg ggatgggaga | 780 |
| tgatggcagc cccccagcga aaaaaatgat aacggacatt catgcaaatg gaaaaacgat | 840 |
| aaacaaggtg ccaacagtta agaaggaaca cttggatgac tatggagaag caccagtgga | 900 |
| aactgatgga gagcatgtta agcgaacctg tacttctgtt cctgaaactt tgcatttaaa | 960 |
| tcccagtttg aaacacacat tggcacaatt ccatttaagt agtcagagct cgctgggtgg | 1020 |
| accagcagca tttctgctc ggcattccca agaaagcatg tcgcctactg tatttctgcc | 1080 |
| tcttccatca cctcaggttc ttcctggccc attgctcatc ccttcagata gctccacaga | 1140 |
| actcactcag actgtgttgg aaggggaatc tatttcttgt tttcaagttg gaggagaaaa | 1200 |
| gagactctgt ttgccccaag tcttaaattc tgttctccga gaatttacac tccagcaaat | 1260 |
| aaatacagtg tgtgatgaac tgtacatata ttgttcaagg tgtacttcag accagcttca | 1320 |
| tatcttaaag gtactgggca tacttccatt caatgcccca tcctgtgggc tgattacatt | 1380 |
| aactgatgca caaagattat gtaatgcttt attgcggcca cgaacttttc ctcaaaatgg | 1440 |
| tagcgtactt cctgctaaaa gctcattggc ccagttaaag gaaactggca gtgcctttga | 1500 |
| agtggagcat gaatgcctag gcaaatgtca gggtttattt gcaccccagt tttatgttca | 1560 |
| gcctgatgct ccgtgtattc aatgtctgga gtgttgtgga atgtttgcac cccagacgtt | 1620 |
| tgtgatgcat tctcacagat cacctgacaa agaacttgc cactgggct ttgaatcagc | 1680 |
| taaatggcat tgctatcttc atgtgaacca aaaatactta ggaacacctg aagaaagaa | 1740 |

| | |
|---|---|
| actgaagata attttagaag aaatgaagga gaagtttagc atgagaagtg gaaagagaaa | 1800 |
| tcaatccaag acagatgcac catcaggaat ggaattacga tcatggtatc ctgttataaa | 1860 |
| gcaggaaggt gaccatgttt ctcagacaca ttcatttta caccccagct actacttata | 1920 |
| catgtgtgat aaagtggttg ccccaaatgt gtcacttact tctgctgtat cccagtctaa | 1980 |
| agagctcaca aagacagagg caagtaagtc catatcaaga cagtcagaga aggctcacag | 2040 |
| tagtggtaaa cttcaaaaaa cagtgtctta tccagatgtc tcacttgagg aacaggagaa | 2100 |
| aatggattta aaacaagta gagaattatg tagccgttta gatgcatcaa tctcaaataa | 2160 |
| ttctacaagt aaaaggaaat ctgagtctgc cacttgcaac ttagtcagag acataaacaa | 2220 |
| agtgggaatt ggccttgttg ctgccgcttc atctccgctt cttgtgaaag atgtcatttg | 2280 |
| tgaggatgat aagggaaaaa tcatggaaga agtaatgaga acttatttaa acaacagga | 2340 |
| aaaactaaac ttgattttgc aaaagaagca acaacttcag atggaagtaa aaatgttgag | 2400 |
| tagttcaaaa tctatgaagg aactcactga agaacagcag aatttacaga aagagcttga | 2460 |
| atctttgcag aatgaacatg ctcaaagaat ggaagaattt tatgttgaac agaaagactt | 2520 |
| agagaaaaaa ttggagcaga taatgaagca aaaatgtacc tgtgactcaa atttagaaaa | 2580 |
| agacaaagag gctgaatatg caggacagtt ggcagaactg aggcagagat ggaccatgc | 2640 |
| tgaggccgat aggcaagaac tccaagatga actcagacag gaacgggaag caagacagaa | 2700 |
| gttagagatg atgataaaag agctaaagct gcaaattctg aaatcatcaa agactgctaa | 2760 |
| agaatagaaa ctgttaaaga gattcatctg tgtattactg acaaggtttt ttttgtttgt | 2820 |
| tgcttgcttt ggtaattgaa ttctgaagaa tttatctgca tgacgataac taggcattct | 2880 |
| atccatttgt agatcagaga aagtgaagag attatatatt agtacttaaa tttttacatt | 2940 |
| ttccaaatga atgaaaatgt atgtttcttt gtactttttt aaaaaaatca gcttagtaac | 3000 |
| aatactatat ggtttcaact agtaggtaat ctgcttatat ttctaatgca aacttaacaa | 3060 |
| ttgtgtactt tttaaaagct gcaatatgtg ttggaaaata gctgtggtca attttgttat | 3120 |
| ccatatttca gactcaattt tagatacaat ggtggcttta tatttaagt atatagagct | 3180 |
| actcaaggag ttgaatctcc ccttttctca ttaacacaat ttttctaagt tgatatggtg | 3240 |
| tactcattaa catacaccaa atttacttt actttgttca gattgtggaa tgaatttcca | 3300 |
| ccagttctct tctttttaat gtgtacccta ggaggaattt tactgaggtt atagcatacc | 3360 |
| ccatgagcac agtggggaag aagaatgtgt tgttatgtgc tgctgctaaa cagaagcagc | 3420 |
| agttgtaatt tgttttcag tttaaatgtg gttatagtta gattttttt taagcagcaa | 3480 |
| cttttcaaaa ataaaatgtg ataatttctg aaaaaaaaaa aaaaaa | 3526 |

<210> SEQ ID NO 3
<211> LENGTH: 2194
<212> TYPE: DNA
<213> ORGANISM: Homo sapiens

<400> SEQUENCE: 3

| | |
|---|---|
| gtgccggcca atgggaggtg cgctcgggct gcttccggct ccgcgctccg ctcgcccct | 60 |
| cccaaggtct ccccgcgact ggcgggacgc aggggcgggc gtcggccgcg gtgacgcgca | 120 |
| gcgggcctgg agccaataag gggcgggctc ggtgctgatg acggtgctg gtggccagtg | 180 |
| gagaggcgct ggccgcactt cccgtcgggg agagagtgta atatggcgaa gacctacgat | 240 |
| tacctgttca agctgctgct gatcggggac tcggggtgg ggaagacctg tgtcctgttc | 300 |

| | |
|---|---|
| cgcttctccg aggacgcctt caactccact tttatctcca ccataggaat tgactttaaa | 360 |
| attaggacca tagagctcga tggcaagaga attaaactgc agatatggga cacagccggt | 420 |
| caggaacggt ttcggacgat cacaacggcc tactacaggg gtgcaatggg catcatgctg | 480 |
| gtctacgaca tcaccaacga gaagtccttc gacaacatcc ggaactggat tcgcaacatt | 540 |
| gaggagcacg cctctgcaga cgtcgaaaag atgatactcg ggaacaagtg tgatgtgaat | 600 |
| gacaagagac aagtttccaa ggaacgggga gaaaagctgg ccctcgacta tggaatcaag | 660 |
| ttcatggaga ccagcgcgaa ggccaacatc aatgtggaaa atgcattttt cactctcgcc | 720 |
| agagatatca aagcaaaaat ggacaaaaaa ttggaaggca cagcccca ggggagcaac | 780 |
| cagggagtca aaatcacacc ggaccagcag aagaggagca gcttttccg atgtgttctt | 840 |
| ctgtgaggaa caccgcctta ctctgagcct cgctcagccc agctgactgt gcctgttctg | 900 |
| agtgagcccc tcactcagcc ggggccctcc cacctccaac gccccgccca cgccgcggcc | 960 |
| accgggccca cggccaccag aatgcaattg agaaatcgtt tattttagta actgtctgat | 1020 |
| cttttttcaac tttggagatg gaataagtta aaaatttgct attttttcctg taacatctgc | 1080 |
| tgaacgggcc cacccacacg ttgtatattc agagagagag agggagtcaa ggtgtgaccg | 1140 |
| tcgaccacag ccagtgtcag gcctctgcct ctgggccttt gctttgtggc ctcactgcaa | 1200 |
| cacaaagctc caccaggagg ctggttcacg tcccctacca cggaagcgag gtcccagaag | 1260 |
| gccagcggtg gttccaggag caacagctcc caaaccctga gcaaggcaac cgatcgccag | 1320 |
| gaccaggaag catcacccag gagatttggc gcccacttcc acctcttctc tcagttttgg | 1380 |
| acaagtgaca aaccattttg ccccctcact cttcttttt aactgttaaa ccaaaggaaa | 1440 |
| gcacaaatga aggaaatcct gtgtaaagca ttgagaagga agaagcctg gagcagcctc | 1500 |
| tcctgtccac agccaggggt taggtctgca ggcccgtctg cggtcccat cgagcatcaa | 1560 |
| ggggacgctg tgtgtgctgc aagtgacccc gaaaacaacc acagccgtca catggtcctc | 1620 |
| ctgaagttgg ggcaccctcc tctcagcacc aaaatggccc ccactccttc gtgtcctccc | 1680 |
| gctatctcca aatcggacgt tctttctagc tgagatttt attttccac atctgtagtg | 1740 |
| ccatgaagcg attctgtctt tgacttccaa tggcaaacct gggtgatcgg gaacaagcac | 1800 |
| gttgtaccct tggctggaca tggccaagac acaaggcatt ccacggcggc aagctgaccg | 1860 |
| cacagcagtc tggcttgatt ttcagccgtc atcattgggt tctgtttga cagctctgct | 1920 |
| gtcccatagg gactgcgact gggaccaggt caaccacgcc aggggggtgt caccagcctt | 1980 |
| ttctttttt ctttcttttt ttttttttcc tccttaagct gctgtcaatc caaaccattg | 2040 |
| gcatcatcgt ttcttttgaa ttaaaaccaa catatcagca atagtctgct ctccccggga | 2100 |
| atctctaaca tgctctgttt acatcgataa atgcacttaa ggaaaacaaa caaattaaag | 2160 |
| ctcatcttaa agtccaaaaa aaaaaaaaaa aaaa | 2194 |

<210> SEQ ID NO 4
<211> LENGTH: 2389
<212> TYPE: DNA
<213> ORGANISM: Homo sapiens

<400> SEQUENCE: 4

| | |
|---|---|
| agcgacgcgg tgacgccaca aaaatggcgg acgctggaaa gcgccgttcc tgactctaat | 60 |
| gtacttagac acttgaagcc acaaaaggat ttatccccga ggttcctcat ctgctcgcga | 120 |
| ggatgccttt tctcttctgc cttgcgaaat aacagcagcc tagctgttgc ccgtgaccag | 180 |
| tgagaaaggc agcgtcgcgg gctgattagg tttcacccaa agggtgccgg cgccgaattg | 240 |

```
gtttctaacg agaactttta aaatgatccg ttccaaaaaa gggtaggagc cgcgagaccc    300
tccaactgcc cagagaaaac aagtctcgtc tggcaaagtt ctcggcccac gcggtccgcg    360
gccaagggcc aacggtccct cgccccacgt tgccgcagca ctgcgcgtgc gcgagccgct    420
gtcaaacgcg ctgacggagg ccgagaagaa aaaaaggcgg gagccgtcaa tcccgggttg    480
agcaaaatgg cgcgggagaa ggagatgcag gagttcaccc gtagcttctt ccgaggccgc    540
ccggacctca gcacgcttac gcattccatc gtgcggcgga ggtacttagc tcactcgggc    600
cgcagccacc tggagcccga ggagaagcag gcactgaagc ggctggtgga ggaggagctg    660
ctgaagatgc aggtggatga agccgcttcc agggaagaca aactggacct taccaagaag    720
ggcaagaggc ctcccacccc ttgtagcgac ccggagagaa aaaggttccg cttcaattca    780
gagtcggagt ccggctctga agcctccagc ccagactact ttggaccccc agcaaagaat    840
ggggtggcag cagaagtcag cccagccaaa gaggagaatc aaggcgagc ctcaaaggca    900
gttgaggaga gcagtgatga ggaacggcag agggacctgc ccgcacagag gggagaggag    960
agcagtgagg aggaggaaaa ggggtacaag gggaagacta ggaagaaacc tgtggtaaag   1020
aagcaggcac caggcaaggc ctcagtcagt aggaagcagg ccaggaagaa aagtgaggag   1080
agcgaggcag aacccgttca gaggacagca agaaggtgg agggaaataa aggaactaaa   1140
agcctgaagg aaagtgaaca ggagagtgaa gaggagatcc tagcccagaa gaaagagcag   1200
agagaggagg aagtggagga ggaagagaaa gaagaggatg aggaaaaggg ggattggaaa   1260
cccagaacca ggagcaatgg ccggagaaag tcagctaggg aggagaggag ctgtaagcag   1320
aaaagccagg caaagaggct cttgggagac tcagacagcg aggaagagca gaaagaggca   1380
gccagcagtg gggatgacag tgggagagat agagaacccc cagtgcagag gaagagtgag   1440
gacaggaccc agcttaaggg tgggaagagg ttgagtggaa gcagcgagga cgaggaagac   1500
agtgggaagg gggaacccac agctaaaggc tctagaaaga tggccagact gggcagcacc   1560
agtggtgagg aaagtgactt ggagagggag gtaagtgaca cgcgaggcag gggaggcccc   1620
caggggagaa ggaagaaccg ctcttccaag aagagctcca ggaaaggcag gacacgaagc   1680
tcctcttcct cctcagatgg aagtccagag gccaaaggag ggaaggctgg ctcaggtcgc   1740
cgtggagagg accaccccggc tgtgatgagg ctgaagcgct acattcgggc ctgtggtgcc   1800
catcgaaact acaagaagct gttgggctcc tgttgctcac acaaggagcg cctgagtatc   1860
ctccgggcag aactggaagc gctaggcatg aagggtaccc cttccctagg gaagtgtcgg   1920
gccctgaagg agcagaggga ggaggcagct gaggtggcct ccttggatgt tgcgaacatc   1980
atcagtggct cgggccggcc acgcagacgt acagcctgga acccttagg agaagcagca   2040
cccccagggg agctgtaccg acggaccctg gactcagatg aagagcggcc ccgtcccgca   2100
ccccccagact ggtcacatat gcgtggcatc atcagcagtg atggcgagag taactgagct   2160
ctgccaccccc caggagggac ccttgataca tgtacaaagc atacatagca cccccttgccc   2220
tgtgtctgtg gaacagaagc agcttccttc agagaagact gcagctccca aggacacaag   2280
ctgtttgggat gctacttctc agcttcacgc tgtccctttta aggtgtttat tttttaagac   2340
tcaataaagg agtgttttta atcacctcat caaaaaaaaa aaaaaaaa                2389
```

<210> SEQ ID NO 5
<211> LENGTH: 3720
<212> TYPE: DNA
<213> ORGANISM: Homo sapiens

<400> SEQUENCE: 5

```
aggatacagc ggcttctgcg cgacttataa gagctccttg tgcggcgcca ttttaagcct    60
ctcggtctgt ggcagcagcg ttggcccggc cccgggagcg gagagcgagg ggaggcggag   120
acggaggaag gtctgaggag cagcttcagt ccccgccgag ccgccaccgc aggtcgagga   180
cggtcggact cccgcggcgg gaggagcctg ttcccctgag ggtatttgaa gtataccata   240
caactgtttt gaaaatccag cgtggacaat ggctactcaa gctgatttga tggagttgga   300
catggccatg gaaccagaca gaaaagcggc tgttagtcac tggcagcaac agtcttacct   360
ggactctgga atccattctg gtgccactac cacagctcct tctctgagtg gtaaaggcaa   420
tcctgaggaa gaggatgtgg atacctccca gtcctgtat gagtgggaac agggattttc   480
tcagtccttc actcaagaac aagtagctga tattgatgga cagtatgcaa tgactcgagc   540
tcagagggta cgagctgcta tgttccctga cattagat gagggcatgc agatcccatc   600
tacacagttt gatgctgctc atcccactaa tgtccagcgt ttggctgaac catcacagat   660
gctgaaacat gcagttgtaa acttgattaa ctatcaagat gatgcagaac ttgccacacg   720
tgcaatccct gaactgacaa aactgctaaa tgacgaggac caggtggtgg ttaataaggc   780
tgcagttatg gtccatcagc tttctaaaaa ggaagcttcc agacacgcta tcatgcgttc   840
tcctcagatg gtgtctgcta ttgtacgtac catgcagaat acaaatgatg tagaaacagc   900
tcgttgtacc gctgggacct tgcataacct ttcccatcat cgtgagggct tactggccat   960
ctttaagtct ggaggcattc ctgccctggt gaaaatgctt ggttcaccag tggattctgt  1020
gttgttttat gccattacaa ctctccacaa ccttttatta catcaagaag gagctaaaat  1080
ggcagtgcgt ttagctggtg ggctgcagaa atggttgcc ttgctcaaca aaacaaatgt  1140
taaattcttg gctattacga cagactgcct tcaaatttta gcttatggca accaagaaag  1200
caagctcatc atactggcta gtggtggacc ccaagcttta gtaaatataa tgaggaccta  1260
tacttacgaa aaactactgt ggaccacaag cagagtgctg aaggtgctat ctgtctgctc  1320
tagtaataag ccggctattg tagaagctgg tggaatgcaa gctttaggac ttcacctgac  1380
agatccaagt caacgtcttg ttcagaactg tctttggact ctcaggaatc tttcagatgc  1440
tgcaactaaa caggaaggga tggaaggtct ccttgggact cttgttcagc ttctgggttc  1500
agatgatata aatgtggtca cctgtgcagc tggaattctt tctaacctca cttgcaataa  1560
ttataagaac aagatgatgg tctgccaagt gggtggtata gaggctcttg tgcgtactgt  1620
ccttcgggct ggtgacaggg aagacatcac tgagcctgcc atctgtgctc ttcgtcatct  1680
gaccagccga caccaagaag cagagatggc ccagaatgca gttcgccttc actatggact  1740
accagttgtg gttaagctct acacccacc atcccactgg cctctgataa aggctactgt  1800
tggattgatt cgaaatcttg ccctttgtcc cgcaaatcat gcacctttgc gtgagcaggg  1860
tgccattcca cgactagttc agttgcttgt tcgtgcacat caggataccc agcgccgtac  1920
gtccatgggt gggacacagc agcaatttgt ggaggggtc cgcatggaag aaatagttga  1980
aggttgtacc ggagcccttc acatcctagc tcgggatgtt cacaaccgaa ttgttatcag  2040
aggactaaat accattccat tgtttgtgca gctgctttat tctcccattg aaaacatcca  2100
aagagtagct gcaggggtcc tctgtgaact tgctcaggac aaggaagctg cagaagctat  2160
tgaagctgag ggagccacag ctcctctgac agagttactt cactctagga atgaaggtgt  2220
ggcgacatat gcagctgctg tttttgttccg aatgtctgag acaagccac aagattacaa  2280
gaaacggctt tcagttgagc tgaccagctc tctcttcaga acagagccaa tggcttggaa  2340
```

```
tgagactgct gatcttggac ttgatattgg tgcccaggga gaaccccttg gatatcgcca    2400
ggatgatcct agctatcgtt cttttcactc tggtggatat ggccaggatg ccttgggtat    2460
ggaccccatg atggaacatg agatgggtgg ccaccaccct ggtgctgact atccagttga    2520
tgggctgcca gatctggggc atgcccagga cctcatggat gggctgcctc caggtgacag    2580
caatcagctg gcctggtttg atactgacct gtaaatcatc ctttaggtaa gagttttaa    2640 aaagccagtt tgggtaaaat acttttactc tgcctacaga acttcagaaa gacttggttg    2700
gtagggtggg agtggtttag gctatttgta aatctgccac aaaaacaggt atatactttg    2760
aaaggagatg tcttggaaca ttggaatgtt ctcagatttc tggttgttat gtgatcatgt    2820
gtggaagtta ttaactttaa tgttttttgc cacagctttt gcaacttaat actcaaatga    2880
gtaacatttg ctgttttaaa cattaatagc agcctttctc tctttataca gctgtattgt    2940
ctgaacttgc attgtgattg gcctgtagag ttgctgagag ggctcgaggg gtgggctggt    3000
atctcagaaa gtgcctgaca cactaaccaa gctgagtttc ctatgggaac aattgaagta    3060 aacttttgt tctggtcctt tttggtcgag gagtaacaat acaaatggat tttgggagtg    3120
actcaagaag tgaagaatgc acaagaatgg atcacaagat ggaatttatc aaaccctagc    3180
cttgcttgtt aaattttttt tttttttttt ttaagaatat ctgtaatggt actgactttg    3240
cttgctttga agtagctctt tttttttttt tttttttttt tttgcagtaa ctgtttttta    3300
agtctctcgt agtgttaagt tatagtgaat actgctacag caatttctaa ttttttaagaa    3360 ttgagtaatg gtgtagaaca ctaattcata atcactctaa ttaattgtaa tctgaataaa    3420
gtgtaacaat tgtgtagcct ttttgtataa aatagacaaa tagaaaatgg tccaattagt    3480 ttcctttta atatgcttaa aataagcagg tggatctatt tcatgttttt gatcaaaaac    3540
tatttgggat atgtatgggt agggtaaatc agtaagaggt gttatttgga accttgtttt    3600
ggacagttta ccagttgcct tttatcccaa agttgttgta acctgctgtg atacgatgct    3660
tcaagagaaa atgcggttat aaaaaatggt tcagaattaa acttttaatt cattcgattg    3720
```

<210> SEQ ID NO 6  
<211> LENGTH: 3420  
<212> TYPE: DNA  
<213> ORGANISM: Homo sapiens
<400> SEQUENCE: 6

```
agagcgagcc gagccgcggc cagctccggc gggcaggggg ggcgctggag cgcagcgcag     60
cgcagcccca tcagtccgca aagcggaccg agctggaagt cgagcgctgc cgcgggaggc    120
gggcgatggg ggcaggtgcc accggccgcg ccatggacgg gccgcgcctg ctgctgttgc    180
tgcttctggg ggtgtccctt ggaggtgcca aggaggcatg ccccacaggc ctgtacacac    240
acagcggtga gtgctgcaaa gcctgcaacc tgggcgaggg tgtggcccag ccttgtggag    300
ccaaccagac cgtgtgtgag ccctgcctgg acagcgtgac gttctccgac gtggtgagcg    360
cgaccgagcc gtgcaagccg tgcaccgagt gcgtggggct ccagagcatg tcggcgccgt    420
gcgtggaggc cgacgacgcc gtgtgccgct gcgcctacgg ctactaccag gatgagacga    480
ctgggcgctg cgaggcgtgc cgcgtgtgcg aggcggctc gggcctcgtg ttctcctgcc    540
aggacaagca gaacaccgtg tgcgaggagt gccccgacgg cacgtattcc gacgaggcca    600
accacgtgga cccgtgcctg ccctgcaccg tgtgcgagga caccgagcgc cagctccgcg    660
agtgcacacg ctgggccgac gccgagtgcg aggagatccc tggccgttgg attacacggt    720
```

```
ccacacccccc agagggctcg acagcacag ccccagcac ccaggagcct gaggcacctc      780
cagaacaaga cctcatagcc agcacggtgg caggtgtggt gaccacagtg atgggcagct      840
cccagcccgt ggtgacccga ggcaccaccg acaacctcat ccctgtctat tgctccatcc      900
tggctgctgt ggttgtgggc cttgtggcct acatagcctt caagaggtgg aacagctgca      960
agcagaacaa gcaaggagcc aacagccggc cagtgaacca gacgcccca ccagagggag     1020
aaaaactcca cagcgacagt ggcatctccg tggacagcca gagcctgcat gaccagcagc     1080
cccacacgca gacagcctcg ggccaggccc tcaagggtga cggaggcctc tacagcagcc     1140
tgccccagc caagcgggag gaggtggaga agcttctcaa cggctctgcg ggggacacct     1200
ggcggcacct ggcgggcgag ctgggctacc agcccgagca catagactcc tttacccatg     1260
aggcctgccc cgttcgcgcc ctgcttgcaa gctgggccac ccaggacagc gccacactgg     1320
acgccctcct ggccgccctg cgccgcatcc agcgagccga cctcgtggag agtctgtgca     1380
gtgagtccac tgccacatcc ccggtgtgag cccaaccggg gagccccgc cccgccccac     1440
attccgacaa ccgatgctcc agccaacccc tgtggagccc gcaccccac cctttggggg     1500
gggcccgcct ggcagaactg agctcctctg gcaggacct cagagtccag gccccaaaac     1560
cacagccctg tcagtgcagc ccgtgtggcc ccttcacttc tgaccacact tcctgtccag     1620
agagagaagt gccctgctg cctccccaac cctgcccctg cccgtcacc atctcaggcc     1680
acctgccccc ttctcccaca ctgctaggtg gccagcccc tcccaccaca gcaggtgtca     1740
tatatggggg gccaacacca gggatggtac taggggaag tgacaaggcc cagagactc     1800
agagggagga atcgaggaac cagagccatg gactctacac tgtgaacttg gggaacaagg     1860
gtggcatccc agtggcctca accctccctc agccctctt gccccccacc ccagcctaag     1920
atgaagagga tcgaggcttt gtcagagctg ggaggggttt tcgaagctca gcccacccc     1980
ctcatttttgg atataggtca gtgaggccca gggagaggcc atgattcgcc caaagccaga     2040
cagcaacggg gaggccaagt gcaggctggc accgccttct ctaaatgagg ggcctcaggt     2100
ttgcctgagg gcgaggggag ggtggcaggt gaccttctgg gaaatggctt gaagccaagt     2160
cagctttgcc ttccacgctg tctccagacc cccacccctt ccccactgcc tgcccacccg     2220
tggagatggg atgcttgcct agggcctggt ccatgatgga gtcaggtttg gggttcgtgg     2280
aaagggtgct gcttccctct gcctgtccct ctcaggcatg cctgtgtgac atcagtggca     2340
tggctccagt ctgctgccct ccatcccgac atggacccgg agctaacact ggcccctaga     2400
atcagcctag gggtcaggga ccaaggaccc ctcaccttgc aacacacaga cacacgcaca     2460
cacacacaca ggaggagaaa tctcactttt ctccatgagt tttttctctt gggctgagac     2520
tggatactgc ccggggcagc tgccagagaa gcatcggagg gaattgaggt ctgctcggcc     2580
gtcttcactc gccccccggt ttggcgggcc aaggactgcc gaccgaggct ggagctggcg     2640
tctgtcttca agggcttaca cgtggaggaa tgctcccccca tcctcccctt ccctgcaaac     2700
atggggttgg ctgggcccag aaggttgtga tgaagaaag tgggccagtg tgggaatgcg     2760
gcaagaagga attgacttcg actgtgacct gtggggattt ctcccagctc tagacaaccc     2820
tgcaaaggac tgttttttcc tgagcttggc cagaagggg ccatgaggcc tcagtggact     2880
ttccacccccc tccctggcct gttctgtttt gcctgaagtt ggagtgagtg tggctcccct     2940
ctatttagca tgacaagccc caggcaggct gtgcgctgac aaccaccgct ccccagccca     3000
gggttccccc agccctgtgg aagggactag gagcactgta gtaaatggca attctttgac     3060
ctcaacctgt gatgagggga ggaaactcac ctgctggccc ctcacctggg cacctgggga     3120
```

| | | |
|---|---|---|
| gtgggacaga gtctgggtgt atttattttc ctccccagca ggtggggagg gggtttgggg | 3180 | |
| gcttgcaagt atgttttagc atgtgtttgg ttctggggcc ccttttttact ccccttgagc | 3240 | |
| tgagatggaa ccctttttggc ccccgagctg ggggccatga gctccagacc cccagcaacc | 3300 | |
| ctcctatcac ctcccctcct tgcctcctgt gtaatcattt cttgggccct cctgaaactt | 3360 | |
| acacacaaaa cgttaagtga tgaacattaa atagcaaaga aagaaaaata gtacaaagag | 3420 | |

<210> SEQ ID NO 7
<211> LENGTH: 5864
<212> TYPE: DNA
<213> ORGANISM: Homo sapiens

<400> SEQUENCE: 7

| | | |
|---|---|---|
| ttcgcggcgc ggcggacatg gcggtggagt cctgagctag tcgtgtcccg gcctccagcg | 60 | |
| gcggcagcgg cgacggcggc ggcagcagga ggcggaggga gagcaggagc cactgagatg | 120 | |
| aggaggcgtc gcgcgcgcct gtagctcgcg ggcctcgcag tttgcttgcc taaactggac | 180 | |
| ttgaagcaat ttaaactact ggagatctgc cattttataa tatcacaatt ggaaagaaac | 240 | |
| agattttcaa ataatggaag agtctaaaac cttaaaaagt gaaaatcatg aaccaaagaa | 300 | |
| gaatgttatt tgtgaagaaa gcaaagcagt tcaagttata ggtaatcaaa cattgaaagc | 360 | |
| tagaaatgat aaatccgtaa aagaaattga gaacagctct ccaaatagga atagtagtaa | 420 | |
| aaaaaataag caaaatgata tttgtataga aaaaacagaa gttaaatcat gtaaagtaaa | 480 | |
| tgctgccaac cttccaggtc ctaaagattt ggggttagtc cttcgagatc aaagtcattg | 540 | |
| caaagcaaaa aaatttccta attcaccggt gaaagccgaa aaggcaacca tttcacaggc | 600 | |
| aaaatcagaa aaggcaacca gtttacaggc aaaagcagaa aaatcaccaa agtcacctaa | 660 | |
| ttcagtgaaa gcagaaaaag catccagtta tcagatgaag tcagaaaaag taccaagttc | 720 | |
| accagcagaa gcagaaaagg gacccagttt actgttgaaa gacatgagac agaagacaga | 780 | |
| attacaacag attggaaaaa aaattccaag ctcctttact tctgtggaca aagtgaatat | 840 | |
| tgaagctgta gggggagaaa atgtgctctc gcaaaactca ccacgatctc agaagcaaca | 900 | |
| gacatgtaca gataatactg gtgattctga tgatagtgct tcaggaattg aagacgtatc | 960 | |
| ggacgattta agtaaaatga gaatgatga atctaataaa gaaaattctt cagagatgga | 1020 | |
| ctacttagaa aatgccactg tgatagatga atctgcattg acacctgagc agaggctggg | 1080 | |
| gttgaaacaa gcagaagaac gcttagaaag agatcacatc tttcgacttg aaaaacgatc | 1140 | |
| accagaatat accaattgtc ggtatctatg caaactttgc ttaattcaca ttgaaaaatat | 1200 | |
| ccaggggggct cataaacata taaaggagaa acgacataag aaaaatattt tggaaaaaca | 1260 | |
| agaagaaagt gagcttcgtt ctctgccacc tccttccccct gcccacttgg ctgctttaag | 1320 | |
| tgttgcagtc attgaattag caaagaaaca tggaataaca gatgatgacc tcagagtccg | 1380 | |
| tcaggaaatt gtggaggaaa tgtcaaaggt tataacgaca tttttaccag aatgttcact | 1440 | |
| taggttgtat ggctcatctc tgactagatt tgctctgaaa agtagtgatg ttaatataga | 1500 | |
| tataaaattt cctcccaaga tgaatcatcc agatcttctg ataaaagtac ttgggatttt | 1560 | |
| aaagaaaaat gtattatatg tagatgtgga atctgatttt cacgctaaag ttcctgttgt | 1620 | |
| ggtgtgcaga gatcgaaaaa gtggtttact ttgtagagtg agtgcaggaa acgatatggc | 1680 | |
| atgtctcact actgatttac ttactgccct tggcaaaata gaacctgtct ttattcccttt | 1740 | |
| ggtgttagcc tttcgctact gggctaagtt gtgctatatt gactcccaaa ctgatggtgg | 1800 | |

```
aatcccttct tactgttttg ctttaatggt gatgttttt ctacaacaga gaaaacccc     1860 tcttcttcct tgcttacttg gaagttggat tgaaggcttt gacccaaaaa gaatggatga     1920
ctttcagctg aagggcatag tagaagagaa gtttgtgaag tgggaatgta attcaagtag     1980
tgcaactgag aaaaactcaa ttgctgagga aacaaagct aaggcagacc aaccaaaaga      2040
tgataccaag aagacagaaa cagacaacca agtaatgcc atgaaggaaa acatggcaa       2100 atctccttta gcattggaaa caccaaatcg ggtatccttg ggacagttat ggttagagct     2160
gcttaaattc tacacactgg attttgcttt ggaggaatat gtcatatgtg tacggataca     2220
agatatttta acaagagaaa ataaaaactg gcctaaaagg cgaatagcca ttgaagatcc     2280
attttcagtc aagaggaatg ttgcacggag cttaaacagc cagctggttt acgaatatgt     2340
tgtggagaga tttagggcag cttatcggta ttttgcctgt cctcagacga agggtggaaa     2400
taagtctaca gtggatttca agaaaagaga gaaggggaaa ataagcaata agaaaccagt     2460
caagtcgaac aatatggcaa ccaatggttg tattctgctt ggggaaacca cagaaaaaat     2520
aaatgcagaa agagagcaac ctgttcaatg tgatgaaatg gactgtacat cacagagatg     2580
tattattgac aacaacaatt tgttggtaaa tgaactagat tttgctgacc acggacagga     2640
ctcttcatct ctttctacca gcaaaagcag tgaaatagag ccaaaattag ataagaaaca     2700
agatgattta gcgccttcag aaacttgttt aaaaaaagag ctcagccaat gtaattgcat     2760
tgatttgtct aagtcgcctg acccagataa atctactgga acagactgca ggtcaaattt     2820
agaaacagag agttcacatc agagtgtgtg caccgacaca tctgctacct cttgcaactg     2880
caaagctaca gaagatgctt ctgaccttaa tgatgatgat aacctcccca cccaggaatt     2940
atattatgtg tttgataagt ttattttaac ctctggcaag ccaccaacga tagtatgcag     3000
catctgcaaa aaggatggcc attcaaagaa tgattgccca gaggatttta ggaaaattga     3060
tttaaaacct ctaccaccaa tgacaaaccg atttcgggaa atacttgatt tagtatgtaa     3120
aagatgtttt gatgagttat caccaccttg ttctgaacaa cacaacaggg agcaaatttt     3180
aattggcttg gaaaagttta ttcaaaaaga atatgatgaa aaggcaaggt tgtgcttatt     3240
tggctcttct aagaatggat ttggatttcg tgatagtgat ctggatattt gtatgacccc     3300
ggaaggccat gaaaatgcag agaaattaaa ttgtaaggaa ataattgaaa atttggcaaa     3360
aattcttaag agacatccag gtttaagaaa cattttgcct ataactactg ccaaagtgcc     3420
tatagtaaaa tttgaacaca ggcgaagtgg gttagaaggc gatatcagtt tatataatac     3480
gttggctcaa cataacacaa gaatgctagc tacttatgca gctattgatc ctagagtgca     3540
gtatttggga tatactatga agtgtttgc taagcgatgt gacattgggg atgcttccag      3600
gggaagttta tcttcatatg catatatcct tatggtgctg tactttctgc agcagagaaa     3660
gccacctgtt atcccagttc tacaagagat ctttgatgga aaacagattc cacagagaat     3720
ggttgatgga tggaatgctt tcttctttga taaaacagaa gaactgaaaa agcgtttacc     3780
ttcacttgga aagaacacag aatcattagg ggagctttgg ctgggactgc ttcgtttcta     3840
tactgaagag tttgatttca aggaatatgt aattagcatt cggcagaaaa agctgttgac     3900
aacttttgag aagcagtgga cttccaagtg cattgcaatt gaagaccctt ttgacttgaa     3960
tcataacctt ggtgctggag tttccagaaa aatgaccaat ttcatcatga aagcatttat     4020
caatggaagg aaacttttg gtaccccttt ttatccactc attggcagag aagctgagta     4080
cttctttgat tccagagtat taacagatgg agaactggct cccaatgata gatgttgccg     4140
tgtgtgtgga aaaataggcc actacatgaa agactgccct aaaaggaaaa gcagtttact     4200
```

| | |
|---|---|
| gtttagacta aagaagaaag acagtgaaga agagaaggaa gggaatgaag aagagaaaga | 4260 |
| ttcccgagat gttcttgacc cccgagacct ccacgatact cgagacttta gagacccgag | 4320 |
| agacctcaga tgttttatat gtggagatgc tggacatgta cgaagggagt gcccagaggt | 4380 |
| caagctggcc cgtcagagga atagcagtgt ggcagcagcc cagctggtcc gcaaccttgt | 4440 |
| aaatgctcaa caggtggctg gttcagctca gcaacagggt gatcagtcca taaggactag | 4500 |
| acagtcatca gaatgttctg aatcaccatc ttattctcct cagcctcagc catttccaca | 4560 |
| gaactcttcc cagtcagctg ctattactca gccttcatct cagccaggat cccaacctaa | 4620 |
| gcttggccca cctcagcagg gagcccaacc tccccatcag gtccagatgc cactgtataa | 4680 |
| cttccccag tcaccaccag ctcagtattc tcccatgcac aatatgggat gttgccaat | 4740 |
| gcaccctctc cagatccctg ccccgtcctg gccatccat ggccagtga tccactctgc | 4800 |
| accaggcagt gcccccagca atattggcct aaatgatccc agcatcatct ttgcacagcc | 4860 |
| tgctgccaga cctgtggcaa tccctaacac gtctcacgat ggacactggc cccgtactgt | 4920 |
| ggctccaaat tccctggtaa acagtggtgc agtggggaat tcagagccag gctttcgagg | 4980 |
| actgactcct ccaattcctt gggaacatgc accgcgtccc catttccccc ttgtcccagc | 5040 |
| ttcgtggcct tatggtttgc atcaaaactt catgcatcag ggaaatgccc gattccagcc | 5100 |
| caacaaacct ttctatactc aagacagatg tgccacccgt cggtgtagag agcgttgtcc | 5160 |
| ccacccacca agaggaaacg tgtcggagta atgcgagtcc attttctttc agctggtcta | 5220 |
| ccgatgcaca gcaaccagcc aatcctgctg tctcaagggt atccgtacct caatgtcagt | 5280 |
| tacattcagc agaaaaagtg acatttaatg gaaagcaaaa caaatcaggt cctgatttaa | 5340 |
| aattttaaca cgtttagata gcttatttaa attctaagac tgtttttaca gactgtatta | 5400 |
| tttgtatata aatatgaact atagttttta ctagtatcac caaattgagt gatacaaatt | 5460 |
| tcatctattt tattacccta tttttaaggg aattttatgt tttgtttaac cttgatgaat | 5520 |
| tgtataaaga gagaatttaa aaaattacat tctttatttt ctattagctg tattcatact | 5580 |
| ttggttgctt cagactttat atattgttct taaaagttag gaaagaattt catgtgtttt | 5640 |
| aaattgtcac ttctattctt tacagaacct tgtagtgcca aaaacttttt aaaaggtaaa | 5700 |
| aaaataaaat aaaattacaa catgaagatt cagattttt ttcttttcca tacttgtata | 5760 |
| ttgaacattc aaacttgaat ggaaagttga ttttgtctgt atttgaagta cttctatttt | 5820 |
| aagttaataa atcttttga caagagttaa aaaaaaaaaa aaaa | 5864 |

<210> SEQ ID NO 8
<211> LENGTH: 1756
<212> TYPE: DNA
<213> ORGANISM: Homo sapiens

<400> SEQUENCE: 8

| | |
|---|---|
| acaccctgac ccaagccgag acaggttcca aacctcaacc tgcagccgga aggggaagt | 60 |
| gaaactcggc tgggggtggg ggctcagaag ccgccccaga aagcactgaa agccacagca | 120 |
| cgtacaccca ctccagggat ctgccagcac cctgtggggc ccagactaca ggctgatggc | 180 |
| ggaggcttcg agtgacccgg gtgccgagga gcgggaagag ttgctgggc ccactgctca | 240 |
| gtggagcgtg gaggacgagg aggaggccgt ccacgagcaa tgccagcatg agagagacag | 300 |
| gcagcttcag gccaggacg aggagggagg cggccatgtc ccgagcggc cgaagcagga | 360 |
| gatgctcctc agcctgaagc cctcggaggc ccctgaactg gatgaggacg agggctttgg | 420 |

| | |
|---|---|
| cgactggtcc cagaggccag agcagcggca gcagcacgag ggggcgcagg gcgccttgga | 480 |
| cagcggagag cccccccagt gcaggagtcc tgaggggag caagaggaca ggcccggcct | 540 |
| gcatgcctac gaaaaggagg acagtgatga agtccacctg gaggagttga gtctgagcaa | 600 |
| ggaggggcca ggcccagagg acactgtcca ggacaacctg ggggccgcag ggctgagga | 660 |
| ggaacaggag gagcaccaga aatgtcagca gcccaggaca cccagcccct tggtcttgga | 720 |
| ggggaccatc gaacagagct cgcctcccct gagccctacc accaaactca tcgacaggac | 780 |
| cgagtcccta aaccgctcca tagagaagag taacagtgtg aagaaatccc agccagactt | 840 |
| gcccatctcc aagattgatc agtggctgga acaatacacc caggccatcg agaccgctgg | 900 |
| ccggaccccc aagctagccc gccaggcctc catagagctg cccagcatgg ctgtggccag | 960 |
| taccaagagt cggtgggaga cgggtgaggt acaggctcag tctgcggcca agactccgtc | 1020 |
| ctgcaaggat attgtggctg agacatgag caagaaaagc ctctgggagc agaagggagg | 1080 |
| ctccaagacc tcatcaacaa ttaagagcac cccatctggg aagaggtata agtttgtggc | 1140 |
| caccgggcat gggaagtatg agaaggtgct tgtggaaggg ggcccggctc ctaggcgtc | 1200 |
| ccatctcgct tcctgggtct gcaggtccag ccggctggca ccctccatgt acccagggga | 1260 |
| gattccagcc agacacccgc ccccggccc tggctaagaa gttgcttcct gttgccagca | 1320 |
| tgacctaccc tcgcctcttt gatgccatcc gctgccacct cctttgctc ctggacccct | 1380 |
| tagcctctct gccttccac tctctgacca ccgcccccgc cctccccacc cagctccgct | 1440 |
| tcttgttact tgggggagga agaaactcc tgatcattgg ccaaagggac ttaccctgg | 1500 |
| agaggccaag tgccttctag gaagttagga ggttgaggca cagcctgtgc agagagggtg | 1560 |
| ggtcaccccc ccagatccaa ggagaaactg caggtcaagg gctgataacg gccatgcagg | 1620 |
| atgcttgatg ctgcgtcccc cgctgcttgc cgcccccac cccgccattt tgtataataa | 1680 |
| agctccctgt gtattctcaa aaaaaaaaa aaaaaaaaaa aaaaaaaaaa aaaaaaaaa | 1740 |
| aaaaaaaaaa aaaaaa | 1756 |

<210> SEQ ID NO 9
<211> LENGTH: 2226
<212> TYPE: DNA
<213> ORGANISM: Homo sapiens

<400> SEQUENCE: 9

| | |
|---|---|
| aaacggagtg ggagaagggg gctagcgagg aggaagaggc gggaggtgcg gcagggggcac | 60 |
| aggtgacgct cctcccgcct gcctagcaga gctccaggcg cacatccgca gtcagccacc | 120 |
| tcgcgcgcgc ctccaggagc aaggatggag aggctggtga tcaggatgcc cttctctcat | 180 |
| ctgtctacct acagcctggt ttgggtcatg gcagcagtgg tgctgtgcac agcacaagtg | 240 |
| caagtggtga cccaggatga agagagcag ctgtacacac ctgcttcctt aaaatgctct | 300 |
| ctgcaaaatg cccaggaagc cctcattgtg acatggcaga aaagaaagc tgtaagccca | 360 |
| gaaaacatgg tcaccttcag cgagaaccat ggggtggtga tccagcctgc ctataaggac | 420 |
| aagataaaca ttacccagct gggactccaa aactcaacca tcaccttctg gaatatcacc | 480 |
| ctggaggatg aagggtgtta catgtgtctc ttcaatacct tggttttgg gaagatctca | 540 |
| ggaacggcct gcctcaccgt ctatgtacag cccatagtat cccttcacta caaattctct | 600 |
| gaagaccacc taaatatcac ttgctctgcc actgcccgcc cagcccccat ggtcttctgg | 660 |
| aaggtccctc ggtcagggat tgaaaatagt acagtgactc tgtctcaccc aaatgggacc | 720 |
| acgtctgtta ccagcatcct ccatatcaaa gaccctaaga tcaggtggg gaaggaggtg | 780 |

```
atctgccagg tgctgcacct ggggactgtg accgacttta agcaaaccgt caacaaaggc      840
tattggtttt cagttccgct attgctaagc attgtttccc tggtaattct tctcgtccta      900
atctcaatct tactgtactg gaaacgtcac cggaatcagg accgagagcc ctaaataagt      960
cacacagcac cctgaaagtg attccctggt ctacttgaat ttgacacaag agaaaagcag     1020
gaggaaaagg ggccattctc caaaggacct gaaagagcaa agaggtggg agcgaaagcc      1080 ttaaggatcc cacgactttt tactgccatc tgagctactc agtgtttgaa tcccaagagg     1140
aagtcagttt acctctcagg tctgttgtag gacttgattt tgtaaagcaa tgccatgtta     1200
tgtggttgaa agggcactgg acttagttag tatcaggagc actgagctca cagactgact     1260
tgggctccta ctggtgggga cctctgttag tcactttacc tcatccaaag tataaaggaa     1320
ttggaccaaa taatttacca catagctcta aaacttaatt taaaatgtaa ttccagaaaa     1380
aaaaagggaa taagcaaagg gggaagaatt gaaagagaga gagaagaaag aatacagaga     1440
gcttaccttt tgcctttctg ttgatgttac atctcttctt cctatgttct taggtctatg     1500
agtctgtttc cccatcattt ggtatctagt ccagttcctg cttactgctt tgctaatagc     1560
tggccttgct agaatccttg gtttcactgc tgttcttcat gtgcttctat gagatttact     1620
ccaacacaaa taggactgaa tttattgtga agtaacattg gcaatcttaa cttattcatt     1680
taacttattt ttatagctag ataaatattg ttagtcttag acaatagctc acatttttg      1740 agaagcatgc cctccctgtc catttgtctt ataacatgac ccagccctat tttacgtcat     1800
tctaaattca gcctcatata atgaaaatac attatgaaaa cagatgttta ggagatttcc     1860
tgtatagcag tcagccaatt catatgcttt gtctctgctg gcttcttttt ccatgcgtta     1920
acttttccca atagcagagg aggcaaatat gagcatacaa tcccttttgt ctaaagatat     1980
tgttccagct agtggaatga tgttgaatct ttaataacca taattagttg cttttttcagt    2040 atcttctgct ttgtctgtgt ctatccagtg gcctaggaat taaagtgtaa gttgtttcg      2100 ctgttaaatt ggatatttat atatatatat agcaagattt tcatgtgtta tttaattctg     2160
tattgtttct tatatttgta gtaaaatatt gaacaattaa aagtgttgac tccaaaaaaa     2220
aaaaaa                                                                 2226

<210> SEQ ID NO 10
<211> LENGTH: 4065
<212> TYPE: DNA
<213> ORGANISM: Homo sapiens

<400> SEQUENCE: 10
gggaacaaac ttcagaagga ggagagacac cgggcccagg gcaccctcgc gggcggaccc       60
aagcagtgag ggcctgcagc cggccggcca gggcagcggc aggcgcggcc cggacctacg      120
ggaggaagcc ccgagccctc ggcgggctgc gagcgactcc ccggcgatgc ctcacaactc      180
catcagatct ggccatggag ggctgaacca gctgggaggg gcctttgtga atggcagacc      240
tctgccggaa gtggtccgcc agcgcatcgt agacctggcc caccagggtg taaggccctg      300
cgacatctct cgccagctcc gcgtcagcca tggctgcgtc agcaagatcc ttggcaggta      360
ctacgagact ggcagcatcc ggcctggagt gatagggggc tccaagccca aggtggccac      420
ccccaaggtg gtggagaaga ttggggacta caaacgccag aaccctacca tgtttgcctg      480
ggagatccga accggctcc tggctgaggg cgtctgtgac aatgacactg tgcccagtgt      540
cagctccatt aatagaatca tccggaccaa agtgcagcaa ccattcaacc tccctatgga      600
```

| | |
|---|---|
| cagctgcgtg gccaccaagt ccctgagtcc cggacacacg ctgatcccca gctcagctgt | 660 |
| aactcccccg gagtcacccc agtcggattc cctgggctcc acctactcca tcaatgggct | 720 |
| cctgggcatc gctcagcctg cagcgacaa gaggaaaatg gatgacagtg atcaggatag | 780 |
| ctgccgacta agcattgact cacagagcag cagcagcgga ccccgaaagc accttcgcac | 840 |
| ggatgccttc agccagcacc acctcgagcc gctcgagtgc ccatttgagc ggcagcacta | 900 |
| cccagaggcc tatgcctccc ccagccacac caaaggcgag cagggcctct acccgctgcc | 960 |
| cttgctcaac agcaccctgg acgacgggaa ggccaccctg accccttcca acacgccact | 1020 |
| ggggcgcaac ctctcgactc accagaccta ccccgtggtg gcagatcctc actcacccct | 1080 |
| cgccataaag caggaaaccc ccgaggtgtc cagttctagc tccaccccct cctctttatc | 1140 |
| tagctccgcc tttttggatc tgcagcaagt cggctccggg gtcccgccct tcaatgcctt | 1200 |
| tccccatgct gcctccgtgt acgggcagtt cacgggccag gccctcctct cagggcgaga | 1260 |
| gatggtgggg cccacgctgc ccggataccc accccacatc cccaccagcg acagggcag | 1320 |
| ctatgcctcc tctgccatcg caggcatggt ggcaggaagt gaatactctg gcaatgccta | 1380 |
| tggccacacc ccctactcct cctacagcga ggcctggcgc ttccccaact ccagcttgct | 1440 |
| gagttcccca tattattaca gttccacatc aaggccgagt gcaccgccca ccactgccac | 1500 |
| ggcctttgac catctgtagt tgccatgggg acagtgggag cgactgagca acaggaggac | 1560 |
| tcagcctggg acaggcccca gagagtcaca caaaggaatc tttatttatt acatgaaaaa | 1620 |
| taaccacaag tccagcattg cggcacactc cctgtgtggt taatttaatg aaccatgaaa | 1680 |
| gacaggatga ccttggacaa ggccaaactg tcctccaaga ctccttaatg aggggcagga | 1740 |
| gtcccaggga aagagaacca tgccatgctg aaaaagacaa aattgaagaa gaaatgtagc | 1800 |
| ccccagccgg tacccaccaa aggagagaag aagcaatagc cgaggaactt gggggggatgg | 1860 |
| cgaatggttc ctgcccgggc caagggggtg cacagggcac ctccatggct ccattattaa | 1920 |
| cacaactcta gcaattatgg accataagca cttccctcca gcccacaagt cacagcctgg | 1980 |
| tgccgaggct ctcctcacca gccacccagg gagtcacctc cctcagcctc ccgcctgccc | 2040 |
| cacacggagg ctctggctgt cctctttctc cactccattt gcttggctct ttctacacct | 2100 |
| ccctcttggg catgggctga gggctggagc gagtccctca gaaattccac caggctgtca | 2160 |
| gctgacctct tttgcctgct gctgtgaagg tatagcacca ccccaggtcc tcctgcagtg | 2220 |
| cggcatcccc ttggcagctg ccgtcagcca ggccagcccc agggagctta aaacagacat | 2280 |
| tccacagggc ctgggcccct ggggaggtgag gtgtggtgtg cggcttcacc cagggcagaa | 2340 |
| caaggcagaa tcgcaggaaa cccgcttccc cttcctgaca gctcctgcca agccaaatgt | 2400 |
| gcttcctgca gctcacgccc accagctact gaagggaccc aaggcacccc ctgaagccag | 2460 |
| cgatagaggg tccctctctg ctccccagca gctcctgccc ccaaggcctg actgtatata | 2520 |
| ctgtaaatga aactttgttt gggtcaagct tccttctttc taaccccag actttggcct | 2580 |
| ctgagtgaaa tgtctctctt tgccctgtgg ggcttctctc cttgatgctt ctttcttttt | 2640 |
| ttaaagacaa cctgccatta ccacatgact caataaacca ttgctcttca tctcaggctt | 2700 |
| tggggttggc tggggaagga ggcatcccgg ggctgggctt tctcccaaga acatcagagc | 2760 |
| tgagtagccg acaaactcac tttggggccg tgggctggaa gggaccatct gatgcccag | 2820 |
| agctctggct tggccttctc cctctgcctt taattcacgt tgaacgctgg gtacctcact | 2880 |
| catcccaagt tcttcaacac tgagcaaatg caaggatagc acagtactga gccaaccata | 2940 |
| gactccccac aaggagttgc tgttgttatt aacaggaagc cagagaatca gcagggtggg | 3000 |

```
ttagtgaggg atccgggaat agctgtgact ggagcctgca taaacagctc tgaagggaga    3060
gagaagactg ggctctcttg tgtgccaggc acagtatgga aggcttcata taagttaagc    3120
tgaaattagc cctgttttac atacagcttc attttacata tgaggaaact gaggctttga    3180
aaaaaatgag atgtcttgtc caagatgaaa agtagtagat tcaaccaagt cctcttactc    3240
taagcccaac gcttttaccc aaaacccag agtcctcatc agggatgcca atggttcta     3300 gacccagtgg aggttctgga gctgccactg gggatttaat ttcttttgat ttgctaaaga    3360
tttgacctga ctgaatggag aggtagagtg tagtgtggcc aggacaaggt gagggaggct    3420
gtagagactt agcactttag gccaaccacc tccaggaaat ctgggaaatg caatgtgaca    3480
gctcgggctc tgcactccag ggggctgtct ggtgtccaca tggaccttct ccatgtggga    3540
cacagctgga acaaggggc aggggcctgc agctgggatg cccaggtgaa tatgggcagc     3600
tggacaaaca acactgggat tgagtcagat agaaggggcc caaggactcc agggctggga    3660
ggacagaggc tgggagagag ggctcttacc tccttaggcc tcccaaagag cggttaggga    3720
tgctgccatg gatggcatgg caggggaac cctcctggaa gaaaatccat ctcttctgaa     3780
gggatctgag atgcggctgg tttttcaatg gcagaacttc cctctgcagc gcgactccga    3840
atccatgaca tctgagagtc ttcctgacca caaacctctg ggatcccgag ggctccctac    3900
ccaagaatca ctttgagcac agcatcccaa ggagcccata gagcgatccc ttgcattcac    3960
agccacagcc cctctgggga cactctgtac ccccggcaga cccttttccaa ctcacaacca    4020 ataaaggggc ttgggctgtg ctttgactaa ggtgaaaaaa aaaaa                    4065

<210> SEQ ID NO 11
<211> LENGTH: 4390
<212> TYPE: DNA
<213> ORGANISM: Homo sapiens

<400> SEQUENCE: 11
gagttggggc cagctcccca cccccaagag gccccacatt ccgggccagc agcccagaaa      60
gtccctcccc gcaggcggag acagcccaa gaagtcgacg ccccggtccc gccgcccggc      120
cactacccag agggctgccg ccgcctctcc aagttcttgt ggccccgcg gtgcggagta     180 tggggcgctg atggccatgg agggctactg gcgcttcctg gcgctgctgg ggtcggcact    240
gctcgtcggc ttcctgtcgg tgatcttcgc cctcgtctgg gtcctccact accgagaggg    300
gcttggctgg gatgggagcg cactagagtt taactggcac ccagtgctca tggtcaccgg    360
cttcgtcttc atccagggca tcgccatcat cgtctacaga ctgccgtgga cctggaaatg    420
cagcaagctc ctgatgaaat ccatccatgc agggttaaat gcagttgctg ccattcttgc    480
aattatctct gtggtggccg tgtttgagaa ccacaatgtt aacaatatag ccaatatgta    540
cagtctgcac agctgggttg gactgatagc tgtcatatgc tatttgttac agcttctttc    600
aggtttttca gtctttctgc ttccatgggc tccgctttct ctccgagcat ttctcatgcc    660
catacatgtt tattctggaa ttgtcatctt tggaacagtg attgcaacag cacttatggg    720
attgacagag aaactgattt tttccctgag agatcctgca tacagtacat tccgccaga    780 aggtgttttc gtaaatacgc ttggccttct gatcctggtt tcggggcccc tcatttttg    840 gatagtcacc agaccgcaat ggaaacgtcc taaggagcca aattctacca ttcttcatcc    900
aaatggaggc actgaacagg gagcaagagg ttccatgcca gcctactctg gcaacaacat    960
ggacaaatca gattcagagt taaacagtga agtagcagca aggaaaagaa acttagctct    1020
```

```
ggatgaggct gggcagagat ctaccatgta aaatgttgta gagatagagc catataacgt    1080
cacgtttcaa aactagctct acagttttgc ttctcctatt agccatatga taattgggct    1140
atgtagtatc aatatttact ttaatcacaa aggatggttt cttgaaataa tttgtattga    1200
ttgaggccta tgaactgacc tgaattggaa aggatgtgat taatataaat aatagcagat    1260
ataaattgtg gttatgttac ctttatcttg ttgaggacca caacattagc acggtgcctt    1320
gtgcagaata gatactcaat atgtgaatat gtgtctacta gtagttaatt ggataaactg    1380
gcagcatccc tggcctgttg tcatgcagtc atttcctgtt aattctggga gacaatgatt    1440
tcacaactag cgggaagcag tcctaaaagt ttaaaatccg ataaggaata tctgggacag    1500
ggtttagatc atgactctac acagatacca tgatgagagt atattaaaga aatttaggaa    1560
agcacctggt tccttttctcc ccatgcctgc cttctgctcc ctccccagct ggtttgggct    1620
caaattgtcc ctggagacta gggtttatgt tagggtattg atagattaga gcaggtggtt    1680
gaagagatct tctctggtca gacttggaag aatttccaaa actgaagtta gccccaagac    1740
ttccctaggg ttgatgtact ttatgatcca gatgctaaac ttcttagaat gaaaatatgc    1800
ttcaacactt aagtagcata cactgcccta caaacctcag agagcacttt tccccaagtt    1860
cttgttttta tttttgaaag tactcacaca gcacttacta tgctccaaac actcctctaa    1920
gcactttaca catattagct cattcagtcc ccagacagac gggatgaagt aggtattgtt    1980
actgttccca ttttacaggt gagagatttg aagcctgggg aggctagtaa ctcaccccaa    2040
ggtcacacgg ctcatacatg gtgggactga gactcagatg caggcagtct ggcacctcag    2100
tctggattct aaccatttca ctaagctatt tttgtcttgt actactttga cccacccctg    2160
aataaacctc aattgctgga gtggggtgta gttattaaag ggatgctttt tacctttttgc    2220 tgtttgctgt ggcagattcc ccagataacc aaggaaaagg ggccacccat acctggaaat    2280
aggccatagg gccctacta ctgccaacaa gccatggcct accttgacac ttgtttgatc    2340
ttaaaattgt gtcttggtaa caaaagattt ggacaggcat atctgtagct ttcaagttaa    2400
ttaattgcaa tattttttc ttcaggattt tagctgctga caactttca gtttggagct    2460 aaaagagacc tgtctcatgg tctgcccttc cctggggcaa tagctagggt cttttcctgat    2520 tttatggaa ttttagggga tattttgagc tttgggttct cagtagtgaa ttgagacttg    2580
gaggtgactt tcatgtttg gagtatcatc tctgtctggg atctgggctg acaaattaaa    2640
acctagagta gtgcttatgc tgaaatgata cttttcattt tttggttgat ttttttgcct    2700
tcccttcaat tttaaactga agcatttaa tatgggtaga aactctacac caaatacact    2760
aaacattttg gtgcttagtg gatttctttt taggtaactg gtacttactt ccaaagactg    2820
aatacaagcc acactccatc atatccctta aacttcatga aaaccattc aagatcccct    2880 tgctgcaaca ctgttctctt cttctctact aaattctatt tccaaaattg gtaatagagc    2940
cagaaggatc cccagtaccc agccctctgc ctggcacaaa gtggtagcac aattaaattc    3000
agtatgggtg gagcatggta cagtcttggt gccatagaag gagtagttgc atagtcacac    3060
atcatttgat aagttggatg ttccattaca tagaggaaca caaaattcca gggttttgg    3120 aggaagggat tagatagtga ctaagccgcc agaattgagg tggccattcc tttttgtata    3180
ggctaagaaa caggttatca gtgaaaagtt aattatggct ttgcactag aatagcactg    3240 ttgcaaagta tttaagcacc ccccatctca gcccttatt ttatctttca tgtgggctaa    3300
tgtgaggata atcttacaga tattatagga atttcttttc tatctttatg aaaacaacgt    3360
atataaaata tatctagaaa acctttgttt gagactctta tttaatgggc ttttgattct    3420
```

```
aatgataatt gtacctttat ctttcaaaag ctgatatttc ctacctaagc atctcccgag    3480
aaaaatatct cattaaaaag cccataaata ataggggaga agaaagcctt aggtatcaat    3540
tccaaaacag tgattgaaat ttcccaaaat aattatggct tctgtcatct ccagagataa    3600
tctggcttgg tttaccccat aatctaattt cagaaaagaa agctttattt taacactcat    3660
ctgaatcaac attaaagcct tttctctcaa agcgtttatt gagaaactca atgaatata     3720 ctttttgaat tactgtcatc aaaagtgtac ggcttcctgt gctgcttgtg tcaaatggaa    3780
cctgccctct aaagcacttt cttccttta cttgcgtggt ttcatgtaag ctgtgctgtt    3840
tagaaacaac atctcagact ttacaaagaa atgacaaaga aggcaattgc acttttaag    3900 ggatatcgac aagcagtttc tgttttctaa aggacaaaat acagagtgtg tgtcattttt    3960
aattagattc ttttccctgc tgagttggaa attccagtgc agcactgatt gaccacagtt    4020
gccaatctaa aagcacaaag acagaagtaa agctttatgc taatttatt tcaatatgat    4080 agaaaattta tcttggtatg tccttttta gataactcca gcaggaaact gtaactgcta    4140
tgtctttagg aaaatgtaga agaaagaaca ttattgttct ttaattccta caaggtactc    4200 gaaaaccta agtgaaaag atttctatct ttttatctta gcgcatttat ggaaaaaata    4260
ttaactatcc tgaatatttt ataattttgt aggaaaaata tgcatctatt ttttcttgac    4320
ttcttttata tagtaataaa agttattttg gaagctcaaa aaaaaaaaa aaaaaaaaa     4380 aaaaaaaaaa                                                          4390

<210> SEQ ID NO 12
<211> LENGTH: 2100
<212> TYPE: DNA
<213> ORGANISM: Homo sapiens

<400> SEQUENCE: 12
gtgctcagag agagagagac taagacggat aacgcgtcat ctcgccttcc caaattttcc      60
cccctcgcta gaccgggtcc aaaacctcca tccggagccg gcaggagagg agaacgatgt     120
ttaactcggt caacctgggc aacttctgct ctccgtcgcg caaggagagg ggcgcagatt     180
tcggcgagcg agggagctgc gcctccaacc tctatctgcc cagttgcact tactacatgc     240
ccgagttctc cacggtctcc tccttcctgc cccaggcccc ctctcgtcag atctcctatc     300
cctactcggc ccaagtgccc ccggtccggg aggtctccta cggcctggag ccatccggca     360
agtggcacca tcggaacagc tactcctcct gctatgcggc ggccgacgag cttatgcacc     420
gggagtgcct gcctccttcc accgtcaccg agatcctcat gaaaacgaa ggctcctacg     480 gcggccacca ccacccagc gccccgcacg caaccccgc cggcttctac tcctcagtca     540
acaagaacag cgtcctgcct caagccttcg accgtttctt cgacaacgcc tactgcggtg     600
gcggcgaccc gccgccgag ccccctgct ccggcaaggg cgaggccaag ggggagcccg     660
aggcaccccc ggcctcggga ctggcgtccc gggctgaggc gggtgccgag gcggaggctg     720
aggaggagaa cacaaatccc agctcgtccg gttcagccca ctccgtggcc aaggagccgg     780
ccaaaggagc cgccccaac gccccccgca cccgcaagaa cgcgctgccct tattcgaaat     840 tccagatccg ggaactggag cgagagtttt tcttcaacgt gtatatcaac aaagagagc     900 ggctgcagct gtcccggatg ctgaacctga cggaccgaca agtgaaaatt tggttcaga     960 acagaaggat gaaagaaaag aaactgagca gagaccggct gcagtatttc tcgggaaatc    1020
ctctgctgta acctgcagac cgggcccttt tggggcgggg gggaggggaa aattatttta    1080
```

```
tttatttttt attttttatt ttctaactcg tcttctttcc gccggtggaa aactggactg    1140
tggccagggc tggccccccac cgctgtggcc ggcactccat tccggaacct cctggaccct    1200
ctatctgact ctcgctgtgg gacagggacc gggcctggaa aggggtgaa gggaagtgtc    1260 tgatgcacgg cgagtgaaca ccgttggcgc cgaggccaag actttgattt aaaagaaaac    1320
acacctcggc gacaatgtct tgctgctcgg attaggtggg ggaggggcga cagtagtgag    1380
cgcctgagcc gaacaatcct cgaactaaaa gccttcccctt gcccatgtga aaagatccgc    1440
taagacagca tgtctgccag cggaaacttc tcgagctccc ccctctaccc cgccccacct    1500
tgccccacta ctttaggggg cagctaaatg tgatcctgcc ttgctgtgaa atttctgtac    1560
cttcaacctg gtgttaggtg tgcaaagtcc gtgtcctacc tccgtcttcg ccaaggcccc    1620
gcccgagcct agttgttctc ccctgaatg tgtagaacct tcctttgaaa tttcttaatc    1680
ggtgcattga ggtttccaca tcttttttcca agcagtgccc cacttcatgg atttatagct    1740
atagtctatg cagtcgttac ctctttttttt ttttttttta agaaaattga agattggggt    1800
ggtggaggca gtagggagat gggattgggc acctcccccg tgctggggcc tggatttttg    1860
taaataaatt tcccaagcgt ttcttttccac ctggagggaa agggggggac gcccccagtg    1920
agattcaaat cacgcatctc tactcctctg cgtgagtgcg tgtgtacatg tgcactcccc    1980
accctgctcc cttcccagag ggattgctgt gaaattttttt tggtggcaaa taaagataaa    2040
tttcattctg ttcaaaaaaa aaaaaaaaaa aaaaaaaaaa aaaaaaaaaa aaaaaaaaaa    2100

<210> SEQ ID NO 13
<211> LENGTH: 1220
<212> TYPE: DNA
<213> ORGANISM: Homo sapiens

<400> SEQUENCE: 13 tcttttttttt gcctgtccac catctcccta ttaccctttg gtcgagaggg aaagcagaag      60
aagtctgctg gtcacagcgg ggcacctcga ggagaggacg actaggagca cacggcccgg     120
aaaggtccag gtcagggaag ggaataactg tgcttgaaga agaaaattcc caacatggac     180
aaaccacgca aagaaaatga agaagagccg cagagcgcgc ccaagaccga tgaggagagg     240
cctccggtgg agcactctcc cgaaaagcag tcccccgagg agcagtcttc ggaggagcag     300
tcctcggagg aggagttctt tcctgaggag ctcttgcctg agctcctgcc tgagatgctc     360
ctctcggagg agcgcccctcc gcaggagggt cttttccagga aggacctgtt tgaggggcgc     420
cctcccatgg agcagcctcc ttgtggagta ggaaaacata agcttgaaga aggaagcttt     480
aaagaaaggt tggctcgttc tcgcccgcaa tttagagggg acatacatgg cagaaattta     540
agcaatgagg agatgataca ggcagcagat gagctagaag agatgaaaag agtaagaaac     600
aaactgatga taatgcactg gaaggcaaaa cggagccgtc cttatcctat ttaatgtgtt     660 cggccttttaa ttctgttttg cctgctaata gtattgccat tgccacctgg actttctgtt     720
tgcattttct taatgccttt tcccatattc tgaattttaa ctttttgtga ggctttattt     780
tagatgttta gcatgtaact cgcttaaagt tgaggtttcc ccctaaaatc tacaagtttc     840
cctctttcag tcatgagccc tacacatttg catgaaagat gtacattata tattgtgaaa     900
cgaaaaaagc aattttcaaa tggtatatat tgtatcccat ttttgtaaaa aaatgtata     960 tttatatatt aatatgcaaa gaaaagcta aagtataga cttcaaaggc ataacagtgg    1020
ttgtgtggta agataatagg tgatttttta aattttgtt ttatctgaat ttctcatttt    1080
ttcaggacaa acgttttact tgtgttgcaa aaatatataa tgaaaaaatc acacaatttt    1140
```

| | | |
|---|---|---|
| gaagaaaact gtcaatcagc ttataacgac aatgtggcac ttaataaata cttgtcagaa | 1200 | |
| ctttaaaaaa aaaaaaaaaa | 1220 | |

<210> SEQ ID NO 14
<211> LENGTH: 3260
<212> TYPE: DNA
<213> ORGANISM: Homo sapiens

<400> SEQUENCE: 14

| | |
|---|---|
| tcgaaacagc tgccggctgg tcccggccga ggccggcgca gggagggagg agccgcccgg | 60 |
| gctgtggggg cgccgcgagc tgggccggcc tcggtgtgcc cgcgccgcca gcccgctcca | 120 |
| gacgcgccac ctgggcgctc aagaagagg ccgaagtttg ccgcggccgt gagttggagc | 180 |
| tcgcgccggg ccgctgcgcc gggagctccg ggggcttccc tcgcttcccg gtattgtttg | 240 |
| caaactttgc tgctctccgc cgcggccccc aactcggcgg acgccgggcg cggagagccg | 300 |
| agccgggggg gctgtgcgca cgcgtcgggc caggccgggc gggcatgggc gggggcccga | 360 |
| gcagggtgg agagccgggg ccagcagcag cccgtgcccg ggagcggcgg cgctgagggg | 420 |
| cgcggagctc cccgcgagga cacgtccaac gccagcatgc agcgcccggg ccccgcctg | 480 |
| tggctggtcc tgcaggtgat gggctcgtgc gccgccatca gctccatgga catggagcgc | 540 |
| ccgggcgacg gcaaatgcca gcccatcgag atcccgatgt gcaaggacat cggctacaac | 600 |
| atgactcgta tgcccaacct gatgggccac gagaaccagc gcgaggcagc catccagttg | 660 |
| cacgagttcg cgccgctggt ggagtacggc tgccacggcc acctccgctt cttcctgtgc | 720 |
| tcgctgtacg cgccgatgtg caccgagcag gtctctaccc ccatcccgc ctgccgggtc | 780 |
| atgtgcgagc aggcccggct caagtgctcc ccgattatgg agcagttcaa cttcaagtgg | 840 |
| cccgactccc tggactgccg gaaactcccc aacaagaacg accccaacta cctgtgcatg | 900 |
| gaggcgccca caacggctc ggacgagccc accggggct cgggcctgtt ccgccgctg | 960 |
| ttccggccgc agcggcccca cagcgcgcag gagcaccgc tgaaggacgg gggccccggg | 1020 |
| cgcggcggct gcgacaaccc gggcaagttc caccacgtgg agaagagcgc gtcgtgcgcg | 1080 |
| ccgctctgca cgcccggcgt ggacgtgtac tggagccgcg aggacaagcg cttcgcagtg | 1140 |
| gtctggctgg ccatctgggc ggtgctgtgc ttcttctcca gcgccttcac cgtgctcacc | 1200 |
| ttcctcatcg acccggcccg cttccgctac cccgagcgcc ccatcatctt cctctccatg | 1260 |
| tgctactgcg tctactccgt gggctacctc atccgcctct cgccggcgc cgagagcatc | 1320 |
| gcctgcgacc gggacagcgg ccagctctat gtcatccagg agggactgga gagcaccggc | 1380 |
| tgcacgctgg tcttcctggt cctctactac ttcggcatgg ccagctcgct gtggtgggtg | 1440 |
| gtcctcacgc tcacctggtt cctggccgcc ggcaagaagt ggggccacga ggccatcgaa | 1500 |
| gccaacagca gctacttcca cctggcagcc tgggccatcc cggcggtgaa gaccatcctg | 1560 |
| atcctggtca tgcgcagggt ggcggggggac gagctcaccg ggtctgcta cgtgggcagc | 1620 |
| atggacgtca acgcgctcac cggcttcgtg ctcattcccc tggcctgcta cctggtcatc | 1680 |
| ggcacgtcct tcatcctctc gggcttcgtg gccctgttcc acatccggag ggtgatgaag | 1740 |
| acgggcggcg agaacacgga caagctggag aagctcatgg tgcgtatcgg gctcttctct | 1800 |
| gtgctgtaca ccgtgccggc cacctgtgtg atcgcctgct acttttacga acgcctcaac | 1860 |
| atggattact ggaagatcct ggcggcgcag cacaagtgca aaatgaacaa ccagactaaa | 1920 |
| acgctggact gcctgatggc cgcctccatc cccgccgtgg agatcttcat ggtgaagatc | 1980 |

| | |
|---|---:|
| tttatgctgc tggtggtggg gatcaccagc gggatgtgga tttggacctc caagactctg | 2040 |
| cagtcctggc agcaggtgtg cagccgtagg ttaaagaaga agagccggag aaaaccggcc | 2100 |
| agcgtgatca ccagcggtgg gatttacaaa aaagcccagc atccccagaa aactcaccac | 2160 |
| gggaaatatg agatccctgc ccagtcgccc acctgcgtgt gaacagggct ggagggaagg | 2220 |
| gcacagggc gcccggagct aagatgtggt gcttttcttg gttgtgtttt tctttcttct | 2280 |
| tcttcttttt tttttttat aaaagcaaaa gagaaataca taaaaaagtg tttaccctga | 2340 |
| aattcaggat gctgtgatac actgaaagga aaatgtact taagggtttt tgttttgttt | 2400 |
| tggttttcca gcgaagggaa gctcctccag tgaagtagcc tcttgtgtaa ctaatttgtg | 2460 |
| gtaaagtagt tgattcagcc ctcagaagaa aacttttgtt tagagccctc cctaaatata | 2520 |
| catctgtgta tttgagttgg cttgctacc catttacaaa taagaggaca gataactgct | 2580 |
| ttgcaaattc aagagcctcc cctgggttaa caaatgagcc atccccaggg cccaccccca | 2640 |
| ggaaggccac agtgctgggc ggcatccctg cagaggaaag acaggacccg ggcccgcct | 2700 |
| cacccccag tggatttgga gttgcttaaa atagactccg gccttcacca atagtctctc | 2760 |
| tgcaagacag aaacctccat caaacctcac atttgtgaac tcaaacgatg tgcaatacat | 2820 |
| tttttctct ttccttgaaa ataaaaagag aaacaagtat tttgctatat ataaagacaa | 2880 |
| caaaagaaat ctcctaacaa aagaactaag aggcccagcc ctcagaaacc cttcagtgct | 2940 |
| acattttgtg gcttttttaat ggaaaccaag ccaatgttat agacgtttgg actgatttgt | 3000 |
| ggaaaggagg ggggaagagg gagaaggatc attcaaaagt tacccaaagg gcttattgac | 3060 |
| tctttctatt gttaaacaaa tgatttccac aaacagatca ggaagcacta ggttggcaga | 3120 |
| gacactttgt ctagtgtatt ctcttcacag tgccaggaaa gagtggtttc tgcgtgtgta | 3180 |
| tatttgtaat atatgatatt tttcatgctc cactatttta ttaaaaataa aatatgttct | 3240 |
| ttagtttgct gctaaaaaaa | 3260 |

<210> SEQ ID NO 15
<211> LENGTH: 4350
<212> TYPE: DNA
<213> ORGANISM: Homo sapiens

<400> SEQUENCE: 15

| | |
|---|---:|
| agttgaggga ttgacacaaa tggtcaggcg gcggcggcgg agaaggaggc ggaggcgcag | 60 |
| ggggagccg agcccgctgg gctgcggaga gttgcgctct ctacggggcc gcggccacta | 120 |
| gcgcggcgcc gccagccggg agccagcgag ccgaggccca ggaaggcggg acacgacccc | 180 |
| ggcgcgccct agccacccgg gttctccccg ccgcccgcgc ttcatgaatc gcaagtttcc | 240 |
| gcggcggcgg cggctgcggt acgcagaaca ggagccgggg gagcgggccg aaagcggctt | 300 |
| gggctcgacg gagggcaccc gcgcagaggt ctccctggcc gcaggggag ccgccgccgg | 360 |
| ccgtgcccct ggcagcccca gcggagcggc gccaagagag gagccgagaa agtatggctg | 420 |
| aggaggaggc gcctaagaag tcccgggccg ccggcggtgg cgcgagctgg aactttgtg | 480 |
| ccggggcgct ctcggcccgg ctggcggagg agggcagcgg ggacgccggt ggccgccgcc | 540 |
| gcccgccagt tgaccccgg cgattggcgc gccagctgct gctgctgctt tggctgctgg | 600 |
| aggctccgct gctgctgggg gtccgggccc aggcggcggg ccaggggcca ggccagggc | 660 |
| ccgggccggg gcagcaaccg ccgccgccgc ctcagcagca acagagcggg cagcagtaca | 720 |
| acggcgagcg gggcatctcc gtcccggacc acggctattg ccagcccatc tccatcccgc | 780 |
| tgtgcacgga catcgcgtac aaccagacca tcatgcccaa cctgctgggc cacacgaacc | 840 |

```
aggaggacgc gggcctggag gtgcaccagt tctaccctct agtgaaagtg cagtgttccg    900
ctgagctcaa gttcttcctg tgctccatgt acgcgcccgt gtgcaccgtg ctagagcagg    960
cgctgccgcc ctgccgctcc ctgtgcgagc gcgcgcgcca gggctgcgag gcgctcatga   1020
acaagttcgg cttccagtgg ccagacacgc tcaagtgtga aagttcccg gtgcacggcg    1080
ccggcgagct gtgcgtgggc cagaacacgt ccgacaaggg caccccgacg ccctcgctgc   1140
ttccagagtt ctggaccagc aaccctcagc acggcggcgg agggcaccgt ggcggcttcc   1200
cggggggcgc cggcgcgtcg gagcgaggca agttctcctg cccgcgcgcc ctcaaggtgc   1260
cctcctacct caactaccac ttcctggggg agaaggactg cggcgcacct tgtgagccga   1320
ccaaggtgta tgggctcatg tacttcgggc ccgaggagct gcgcttctcg cgcacctgga   1380
ttggcatttg gtcagtgctg tgctgcgcct ccacgctctt cacggtgctt acgtacctgg   1440
tggacatgcg gcgcttcagc tacccggagc ggcccatcat cttcttgtcc ggctgttaca   1500
cggccgtggc cgtggcctac atcgccggct tcctcctgga agaccgagtg gtgtgtaatg   1560
acaagttcgc cgaggacggg gcacgcactg tggcgcaggg caccaagaag gagggctgca   1620
ccatcctctt catgatgctc tacttcttca gcatggccag ctccatctgg tgggtgatcc   1680
tgtcgctcac ctggttcctg gcggctggca tgaagtgggg ccacgaggcc atcgaagcca   1740
actcacagta ttttcacctg gccgcctggg ctgtgccggc catcaagacc atcaccatcc   1800
tggcgctggg ccaggtggac ggcgatgtgc tgagcggagt gtgcttcgtg gggcttaaca   1860
acgtggacgc gctgcgtggc ttcgtgctgg cgccctctt cgtgtacctg tttatcggca   1920
cgtcctttct gctggccggc tttgtgtcgc tcttccgcat ccgcaccatc atgaagcacg   1980
atggcaccaa gaccgagaag ctggagaagc tcatggtgcg cattggcgtc ttcagcgtgc   2040
tgtacactgt gccagccacc atcgtcatcg cctgctactt ctacgagcag gccttccggg   2100
accagtggga acgcagctgg gtggcccaga gctgcaagag ctacgctatc ccctgccctc   2160
acctccaggc gggcggaggc gccccgccgc acccgcccat gagcccggac ttcacggtct   2220
tcatgattaa gtaccttatg acgctgatcg tgggcatcac gtcgggcttc tggatctggt   2280
ccggcaagac cctcaactcc tggaggaagt tctacacgag gctcaccaac agcaaacaag   2340
gggagactac agtctgagac ccggggctca gcccatgccc aggcctcggc cggggcgcag   2400
cgatccccca aagccagcgc cgtggagttc gtgccaatcc tgacatctcg aggtttcctc   2460
actagacaac tctcttttcgc aggctccttt gaacaactca gctcctgcaa aagcttccgt   2520
ccctgaggca aaaggacacg agggcccgac tgccagaggg aggatggaca gacctcttgc   2580
cctcacactc tggtaccagg actgttcgct tttatgattg taaatagcct gtgtaagatt   2640
tttgtaagta tatttgtatt taaatgacga ccgatcacgc gttttctttt ttcaaaagtt   2700
tttaattatt tagggcggtt taaccatttg aggcttttcc ttcttgccct tttcggagta   2760
ttgcaaagga gctaaaactg tgtgcaacc gcacagcgct cctggtcgtc ctcgcgcgcc   2820
tctccctacc acgggtgctc gggacggctg gcgccagct ccggggcgag ttcagcactg   2880
cggggtgcga ctagggctgc gctgccaggg tcacttcccg cctcctcctt ttgccccctc   2940
cccctccttc tgtcccctcc ctttctttcc tggcttgagg taggggctct aaggtacag   3000
aactccacaa accttccaaa tctggaggag ggcccccata cattacaatt cctcccttgc   3060
tcggcggtgg attgcgaagg cccgtccctt cgacttcctg aagctggatt tttaactgtc   3120
cagaactttc ctccaacttc atggggggccc acgggtgtgg gcgctggcag tctcagcctc   3180
```

-continued

| | |
|---|---|
| cctccacggt caccttcaac gcccagacac tcccttctcc caccttagtt ggttacaggg | 3240 |
| tgagtgagat aaccaatgcc aaacttttg aagtctaatt tttgagggt gagctcattt | 3300 |
| cattctctag tgtctaaaac ctggtatggg tttggccagc gtcatggaaa gatgtggtta | 3360 |
| ctgagatttg ggaagaagca tgaagctttg tgtgggttgg aagagactga agatatgggt | 3420 |
| tataaaatgt taattctaat tgcatacgga tgcctggcaa ccttgccttt gagaatgaga | 3480 |
| cagcctgcgc ttagatttta ccggtctgta aatggaaat gttgaggtca cctggaaagc | 3540 |
| tttgttaagg agttgatgtt tgcttttcctt aacaagacag caaaacgtaa acagaaattg | 3600 |
| aaaacttgaa ggatatttca gtgtcatgga cttcctcaaa atgaagtgct attttcttat | 3660 |
| ttttaatcaa ataactagac atatatcaga aactttaaaa tgtaaaagtt gtacactttc | 3720 |
| aacattttat tacgattatt attcagcagc acattctgag ggggaacaa ttcacaccac | 3780 |
| caataataac ctggtaagat ttcaggaggt aaagaaggtg gaataattga cggggagata | 3840 |
| gcgcctgaaa taaacaaaat atgggcatgc atgctaaagg gaaatgtgt gcaggtctac | 3900 |
| tgcattaaat cctgtgtgct cctcttttgg atttacagaa atgtgtcaaa tgtaaatctt | 3960 |
| tcaaagccat ttaaaaatat tcactttagt tctctgtgaa gagaggaga aaagcaatcc | 4020 |
| tcctgattgt attgttttaa actttaagaa tttatcaaaa tgccggtact taggacctaa | 4080 |
| atttatctat gtctgtcata cgctaaaatg atattggtct ttgaatttgg tatacattta | 4140 |
| ttctgttcac tatcacaaaa tcatctatat ttatagagga atagaagttt atatatatat | 4200 |
| aataccatat ttttaatttc acaaataaaa aattcaaagt tttgtacaaa attatatgga | 4260 |
| ttttgtgcct gaaaataata gagcttgagc tgtctgaact attttacatt ttatggtgtc | 4320 |
| tcatagccaa tcccacagtg taaaaattca | 4350 |

<210> SEQ ID NO 16
<211> LENGTH: 2509
<212> TYPE: DNA
<213> ORGANISM: Homo sapiens

<400> SEQUENCE: 16

| | |
|---|---|
| gaaaccgccg acttccggcc gcgcagcggt gggctgagct aaaatggctg aggagagagt | 60 |
| cgcgacgaga actcaatttc ctgtatctac tgagtctcaa aaaccccggc agaaaaaagc | 120 |
| tccagagttt cctattttgg agaagcagaa ctggttgatt catcttcatt atatccggaa | 180 |
| agattatgaa gcctgcaagg ctgttatcaa agaacagctt caagagactc agggattgtg | 240 |
| tgaatatgct atctatgtcc aagcattgat atttcgccta gaaggaaata tccaagaatc | 300 |
| cctagaactc ttccagacat gtgcagttct tagtcctcag agtgctgata acctcaagca | 360 |
| ggtggccaga tctttatttc tttttgggaa acataaagct gccattgaag tatataatga | 420 |
| agcagctaaa ctcaaccaga aagattggga gatcagccat aacctaggag tttgctacat | 480 |
| atacctgaag cagttcaaca aggcacaaga ccagttgcac aatgccctga atcttaatag | 540 |
| gcacgatctg acttatataa tgctggggaa gatccacttg ctgagggag acttggacaa | 600 |
| ggccattgaa gtctacaaga aagcagtgga gttctcacca gaaaatacag agcttcttac | 660 |
| aactttagga ttactctact tacagctcgg catttaccag aaggcatttg aacatcttgg | 720 |
| caatgcactg acttatgacc ctaccaacta caaggccatc ttggcagcag cagcatgat | 780 |
| gcagacccac ggggactttg atgttgccct caccaaatac agagttgtgg cttgtgctgt | 840 |
| tccagaaagt cctccactct ggaataacat tggaatgtgt ttctttggca agaagaaata | 900 |
| tgtggcggcc atcagctgcc tgaaacgagc caactacttg gcacccttg attggaagat | 960 |

```
tctgtataat ttgggccttg tccatttgac catgcagcag tatgcatcag cttttcattt    1020
tctcagtgcg gccatcaact tccagccaaa gatgggggag ctctacatgc tcttggcagt    1080
ggctctgacc aatctggaag atatagaaaa tgccaagaga gcctacgcag aagcagtcca    1140
cctggataag tgtaaccctt tagtaaacct gaactatgct gtgctgctgt acaaccaggg    1200
cgagaagaag aacgccctgg cccaatatca ggagatggag aagaaagtca gcctactcaa    1260
ggacaatagc tctctggaat ttgactctga tggtggaa atggctcaga agttgggagc      1320
tgctctccag gttggggagg cactggtctg gaccaaacca gttaaagatc ccaaatcaaa    1380
gcaccagacc acttcaacca gcaaacctgc cagtttccag cagcctctgg gctctaatca    1440
agctctagga caggcaatgt cttcagcagc tgcatacagg acgctcccct caggtgctgg    1500
aggaacatcc cagttcacaa agccccatc tcttcctctg gagccagagc ctgcggtgga    1560
atcaagtcca actgaaacat cagaacaaat aagagagaaa taagaataga atgaatgacc    1620
ccaaaatagg gtttttcttgg gcgaggatgt gctggattag gaaaggtgac atgacacagg   1680
cagagcagag tggcacccac cacagaatac agtgtgtgtt attacgagga gccagcagtt    1740
gagcctaagg tccttctacc tacctggtat tggcatttga ggtcggaaac cctctactgc    1800
cccataagcc aggaaaagtg aaaagagaac acagttcctt taagaactgg cagcaaggct    1860
tgaggcctta tgtatgtagc tgagtcagca aggtacatga tgctgtctgc tttcaaaagg    1920
acttttctct cctagctgac tgactccttc cttagttcaa ggaacagctg agacagacct    1980
ctgctgagta gctctgtgat gacaaagcct tggtttaact gaggtgatcc tcaggttgtg    2040
aggtttatta gtccccaagg caaacacaaa tattagatta ataatccaac tttaatagta    2100
tacatttaaa agaaaaaaaa caaaagccct ggaagttgag gccaagcctg ctgagtattg    2160
cagctgcatt tgcccaaagg gaatccagaa caagtccctc cctgtatttt gttcttgaga    2220
ggggtcagtc tagaagctag atcctatcag gatgaggagc agcagcccag ggcttgtctg    2280
gatcagcacc aacgatttta aagaaaaag gaagagtttc ttagatgagt aattgttatt     2340
gaagatagtc agtgataacc actgaccaga tgctatcaat acactatgtg tccttttag     2400 aataaagatt acatatcatc attcctttgg ggaaaattgt tattcaggta taaaaacaag    2460
agatcataat aaaaacctaa aagaacctat gaaaaaaaaa aaaaaaaaa                2509
```

<210> SEQ ID NO 17
<211> LENGTH: 7014
<212> TYPE: DNA
<213> ORGANISM: Homo sapiens

<400> SEQUENCE: 17

```
cggggaccgc gacgagcccg ggtcgccgtt ggcagcagca gcagcaacac cagcagcagc      60
agcagccccg gcggcggcgc ggaccccgag cgcccgggcg caccccggct tcccggagcg     120
cgacgcggcg gcagcagccc cggtgcggcc gcgcgcgcct taggctcggc cccgcggctc     180
ggggaccccg actcccggcc cagcgagcgc gtccccggc gccgcccgag agcccgagga      240
ggcagcggcc gcaggcagcc ggggaggggg cggccaccg cccgcgccgg gcatcctcag      300
gagccccaga gcgcggaggg gcggcgccg ccgagcggtg ctggccccg cgggcctccc       360 cggaccttcc ccaccgcctg ggcccgaggg acgcgtgatc gggcgggcgg ccgggcgcaa     420
gggtgggagg gagccgcccc cgcccgcgcc ccctccgccc ctcgcccaa ccctgggcg       480 ccgggcccgg gccgcgcggc ctgaagcgcc cgcgatggcg agcccgccgc ggcacgggcc     540
```

```
gcccgggccg gcgagcggag acggccccaa cctcaacaac aacaacaaca acaacaacca    600
cagcgtgcgc aagtgcggct acctgcgcaa gcagaagcat ggccacaagc gcttcttcgt    660
gctgcgcgga cccggcgcgg gcggcgacga ggcgacggcg ggcgggggt cggcgccgca     720 accgccgcgg ctcgagtact acgagagcga gaaaaagtgg cggagcaagg caggcgcgcc    780
gaaacgggtg atcgctctcg actgctgcct gaacatcaac aagcgcgccg acgccaagca    840
caagtacctg atcgccctct acaccaagga cgagtacttc gccgtggccg ccagaaacga    900
gcaggagcag gagggctggt accgcgcgct caccgacctg gtcagcgagg ccgcgcggc    960 cgccggagac gcgcccccg ccgcgcgcc cgcgcgtcc tgcagcgcct ccctgcccgg      1020
cgccctgggc ggctctgccg gcgccgccgg ggccgaggac agctacgggc tggtggctcc    1080
cgccacggcc gcctaccgtg aggtgtggca ggtgaacctg aagcccaagg gtctgggcca    1140
gagcaagaac ctgacggggg tgtaccgtct gtgcctgtct gcgcgcacca tcggcttcgt    1200
gaagctcaac tgcgagcagc cgtcggtgac gctgcagctc atgaacatcc gccgctgcgg    1260
ccactcggac agcttcttct tcatcgaggt gggccgctcg gccgtcacag gccccggcga    1320
gctgtggatg caggcggacg actcggtggt ggcgcagaac atccacgaga ccatcctgga    1380
ggccatgaag gcgctcaagg agctcttcga gttccggccg cgcagtaaga gccaatcgtc    1440
ggggtcgtcg gccacgcacc ccatcagcgt ccccggcgcg cgccgccacc accacctggt    1500
caacctgccc cccagccaga cgggcctggt gcgccgctcg cgcaccgaca gcctggccgc    1560 cacccccgccg gcggccaagt gcagctcgtg ccgggtgcgc accgccagcg agggcgacgg    1620
cggcgcggcg gcgggagcgg cggccgcggg cgccaggccg gtgtcggtgg ctgggagccc    1680
cctgagcccc gggccggtgc gcgcgcccct gagccgctcg cacaccctga gcggcggctg    1740
cggcggccgc gggagcaagg tggcgctgct gccggcaggg ggcgcgctgc aacacagccg    1800
ctccatgtcc atgcccgtgg cgcactcgcc gccgccgcc accagccccg gctccctgtc    1860
gtccagcagc ggccacggct cgggctccta cccgccgccg cccggccgc acccgcctct    1920 gccgcatccg ctgcaccacg ccccggcca gcggccctcc agcggcagcg cctccgcctc    1980
gggctccccc agcgacccg gcttcatgtc cctggacgag tacggctcca gcccaggcga    2040
cctgcgcgcc ttctgcagcc accgaagcaa cacgcccgag tccatcgcgg agacgccccc    2100
ggcccgagac ggcggcggcg gcggtgagtt ctacgggtac atgaccatgg acaggccccct    2160 gagccactgt ggccgctcct accgccgggt ctcggggac gcggcccagg acctggaccg    2220
agggctgcgc aagaggacct actccctgac cacgccagcc cggcagcggc cggtgcccca    2280
gccctcctct gcctcgctgg atgaatacac cctgatgcgg gccaccttct cgggcagcgc    2340
gggccgcctc tgcccgtcct gccccgcgtc ctctcccaag gtggcctacc cccctaccc    2400 agaggactac ggagacatcg agatcggctc ccacaggagc tccagcagca acctgggggc    2460
agacgacggc tacatgccca tgacgcccgg cgcggccctc gcgggcagtg ggagcggcag    2520
ctgcaggagc gacgactaca tgcccatgag ccccgccagc gtgtccgccc ccaagcagat    2580
cttgcagccc agggccgccg ccgcgccgc gccgccgtg ccttctgcgg ggcctgcggg     2640
gccagcaccc acctctgcgg cgggcaggac attcccggcg agcgggggcg gctacaaggc    2700
cagctcgccc gccgagagct cccccgagga cagtgggtac atgcgcatgt ggtgcggttc    2760
caagctgtcc atggagcatg cagatggcaa gctgctgccc aacgggggact acctcaacgt    2820 gtccccccagc gacgcggtca ccacgggcac ccgccccgac ttcttctccg cagccctgca    2880
ccccggcggg gagccgctca ggggcgttcc cggctgctgc tacagctcct gccccgctc    2940
```

```
ctacaaggcc ccctacacct gtggcgggga cagcgaccag tacgtgctca tgagctcccc    3000
cgtggggcgc atcctggagg aggagcgtct ggagcctcag gccacgccag ggcccagcca    3060
ggcggccagc gccttcgggg ccggccccac gcagccccct caccctgtag tgccttcgcc    3120
cgtgcggcct agcggcggcc gcccggaggg cttcttgggc cagcgcggcc gggcggtgag    3180
gcccacgcgc ctgtccctgg aggggctgcc cagcctgccc agcatgcacg agtacccact    3240
gccaccggag cccaagagcc ccggcgagta catcaacatc gactttggcg agcccggggc    3300
ccgcctgtcg ccgcccgcgc tcccctgct ggcgtcggcg gcctcgtcct cctcgctctt    3360
gtccgccagc agcccggcct cgtcgctggg ctcaggcacc ccgggcacca gcagcgacag    3420
ccggcagcgg tctccgctct ccgactacat gaacctcgac ttcagctccc ccaagtctcc    3480
taagccgggc ccccgagcg ccacccccgt gggctccttg gacggcctcc tgtcccccga    3540
ggcctcctcc ccgtatccgc cgttgccccc gcgtccgtcc gcgtcccccgt cgtcgtctct    3600 gcagccgccg ccaccgccgc cggccccggg ggagctgtac cgcctgcccc ccgcctcggc    3660
cgttgccacc gcccagggcc cgggcgccgc ctcatcgttg tcctcggaca ccggggacaa    3720
tggtgactac accgagatgg cttttggtgt ggccgccacc ccgccgcaac ctatcgcggc    3780
ccccccgaag ccagaagctg cccgcgtggc cagcccgacg tcgggcgtga agaggctgag    3840
cctcatggag caggtgtcgg gagtcgaggc cttcctgcag gccagccagc ccccggaccc    3900
ccaccgcggc gccaaggtca tccgcgcaga cccgcagggg ggccgccgcc gccacagttc    3960
cgagaccttc tcctccacca cgacggtcac ccccgtgtcc ccgtccttcg cccacaaccc    4020
caagcgccac aactcggcct ccgtggaaaa tgtctctctc aggaaaagca gcgagggcgg    4080
cgtgggtgtc ggccctggag ggggcgacga gccgcccacc tccccacgac agttgcagcc    4140
ggcgccccct ttggcaccgc agggccggcc gtggaccccg ggtcagcccg ggggcttggt    4200
cggttgtcct gggagcggtg gatcgcccat gcgcagagag acctctgccg gcttccagaa    4260
tggtctcaac tacatcgcca tcgacgtgag ggaggagccc gggctgccac cccagccgca    4320
gccgccgccg ccgccgcttc ctcagccggg agacaagagc tcctggggcc ggacccgaag    4380 cctcggggt ctcatcagcg ctgtgggcgt cggcagcacc ggcggcggt gcgggggcc     4440 gggtcccggt gccctgcccc ctgccaacac ctacgccagc attgacttct tgtcccacca    4500
cttgaaggag gccaccatcg tgaaagagtg aagatctgtc tggctttatc accaggatgt    4560
cacatgtcag agagtatcat taaaagaaga cgctcagcac tgtttcagcc cgaagctgct    4620
tgcagttttc ttttggatct gagcaatgac tgtgtttgga acatctgtg gactctgtta     4680 gatgaggcac caacaaggca aggtcacctg cctctttccc ttgttccggg atggggcatt    4740
catcattgtg ctgtttgcgt tttgttttgt tttgttttaa caaaattagc tgaagaagtt    4800
attctcaaga aaattggatg ttttcattgg ccttcttaaa ttgtggccag tgtctttaa     4860 tttcttcttc ttttccttt ggcaaagcag atataacctt cagcatgcta ggagagtgca     4920
cccgtaccta tggaagtggt aaaatctggt atttactggc ttacactcaa aacgaccaca    4980
gtcctacctc agttcaaggt aaagccggat ttcgtggcg ggggtcccac aggacctcct    5040
gtagtagccc ctgcgctgtg tgtctggagc gcggtcctcg gccttattga atggtccaa     5100 gtagacagct gcttgttgga ttccagtgca ggtacctgcg atgtttacgt ccacaccgag    5160
cccagtgtgg gactgacatt tctcaatgga agtgaaattt gggattggac tttgaagacg    5220
gattactaaa taataattat tatatgtaac tgaagcaacc tacttttgaa aatcaactgt    5280
```

| | |
|---|---:|
| attgggtagt gggaggtggg agggaagggc tttgggaagg ggatgaatat ctcttttac | 5340 |
| ctttaacaga cttgtttaat cttctcgatg tagatgttta tgtaggtact tcacattgca | 5400 |
| aacgccttt attctattta caagctcaga tgtctctgct ctcctgaatc ttgggcatgc | 5460 |
| ctttctgtaa ccaaaaatcc ctgtaggcgt gctagcaatt ccagggtggt ccgggtttgg | 5520 |
| cagatttgat ttttaaaaaa cgtattatct ttaataaaat gttattatgt caaccagtga | 5580 |
| ggctgccctg aacaaaaaaa acaaaaagaa aaaaaaaaaa ggaaagaaag aaactgataa | 5640 |
| aaagaggcat tccagcccct atgttattga tggaaaaaga aaaagaagaa aagcaatctc | 5700 |
| gcagtacatg ttacttgtcg aaaaaattcc ggacaagact acccttgttt tatgttttca | 5760 |
| gtattctgaa ataccagtg tgtggcagtt ctcgcagatg ttacctaaaa ctgctgaact | 5820 |
| tgaccggcag aatgttctgc cgttttctgc tccctcgaca cttgattgga gggctgtcga | 5880 |
| cctctcctcc cgtgggggct tccccagtgc ctatcttctc tgatagtcat ggagaggtta | 5940 |
| cactaattca ttggagatgt aagttgttgg ttttgttttg ttttgttttt agaaaaaatat | 6000 |
| atataaatat ataatagata tctatcgcta tagaataatg cattaataaa atgaggcttt | 6060 |
| tttagaggaa gaccaaaaaa ttcaatgtct taaaaatata tttaatggca atgcaaaagt | 6120 |
| cttcctgctt ccgtgctgaa ctttagaaca gaggattgta ttgcaagaca aagttgaatg | 6180 |
| taaagtgatc tccctgaaca ttttaaggt tttactttc tgaaattata catcacagca | 6240 |
| gtgcataggc catataatgt tagctggaag gtcaatttca gtgtatgata tactttatta | 6300 |
| agatgtataa aaatcctgaa gttttatt agttttggga ataggcatca atgggtggta | 6360 |
| tttgctttgt aactccccc aggtacgata gggactgaat atggaccctg ctgaaagcag | 6420 |
| tgtattgacg catatttaac tcgccctcta tccgtagagt agtcatgaca ctatacagat | 6480 |
| ggttcgtgtt catactgcag cttaaaacaa gcaaaataca cagatgataa tatgctaaat | 6540 |
| tttcctctat cctgtacatt tcacaaaaag gcatatgcaa tatttacatt tttaatttag | 6600 |
| tttacagaat ggaaccaaaa tgtataaatg ttatgtttgc taaaacttca caatgtatat | 6660 |
| tgggtctttg tacattttgc ctgacttacc ttaaatttaa atatttttt gctatataaa | 6720 |
| ctttaacagt tattaaacag tgttttcttt ttgggtacgt attgtttctg gatatcaaga | 6780 |
| tgttaaatat atttcttgct attgtgatat gacaagagac ttaacttatc ttgctctgtc | 6840 |
| ttccactgta cacgctgtat ataggggtca atgtgatgct gctggagacg agaataaact | 6900 |
| ggactagaat agtgcattgt atttagtctg tattgatcat ggatgccctc cttaatagcc | 6960 |
| atatgcaata aaataaagta cattatttat gaaatgaaaa aaaaaaaaaa aaaa | 7014 |

<210> SEQ ID NO 18
<211> LENGTH: 1513
<212> TYPE: DNA
<213> ORGANISM: Homo sapiens

<400> SEQUENCE: 18

| | |
|---|---:|
| gccgggcgct ccatggccgc gccgtaacgg ggacccagcc gcctcccgc ccagcccagc | 60 |
| ccagcccttc cgcccgccca ggatggaggc gcccgccagc gcgcagaccc cgcacccgca | 120 |
| cgagcccatc agcttcggca tcgaccagat ccttaacagc ccggaccagg acagcgcacc | 180 |
| cgccccgcgg ggccccgacg gcgccagcta cctgggaggg ccccccgggg gccgtccggg | 240 |
| cgccacatac ccgtctctgc ccgcctcctt tgcgggcctc ggcgcgccct tcgaggacgc | 300 |
| gggatcttac agtgtgaacc tgagcctagc gcccgcaggc gtgatccggg tgccggcgca | 360 |
| caggccgctg cccggggccg tgccaccgcc tctgccaagc gcgctacccg ccatgccctc | 420 |

```
cgtgcccacg gtctccagcc ttggcggtct caatttcccc tggatggaga gcagccgccg    480
cttcgtgaaa gaccgcttca cagcggcggc cgcactcacg cccttcaccg tgacccggcg    540
catcggccac ccctaccaga accggacgcc gcccaagcgt aagaagccgc gcacgtcctt    600
ttcccgggtg cagatctgcg agctggaaaa gcgcttccat cgccagaagt acctggcctc    660
tgccgagagg gcggcgctcg ccaagtccct caaaatgacg gacgcgcagg tcaagacctg    720
gttccaaaac cggaggacca gtggcggcgc gcagacggcg gaggagcggg aggcggagcg    780
gcagcaggcg agccggctca tgctgcagct gcaacacgac gccttccaaa agagcctcaa    840
cgactccatc cagcctgacc cgtctctgtct gcacaactcg tcactctttg ctctgcagaa    900
tctgcagccc tgggaggagg atagttccaa ggttcccgct gtcacctccc tggtgtgagc    960
ccaccagcgc gcaccgtcgc cacgatcgc gccccacc cagccgggcg ccccggaccc    1020
cccaggaggg ctgcggggga accggcgccg agagggaag gggccgccta gcccgagtag    1080
gccccagggc gcggccacag actggcgggc gcggaaggg ggtagggccc gagctccgcg    1140
cggccgcaca atccgagccc ccgccccgcg cccgtcccg ccccaggccc gggcctgaca    1200
agaaagcgcc ttacgtttct ccgccccccg cccgcacccc ccgggccggg cgcctgtatt    1260
atactttgta cttttgccca aacgtgtaaa taataaaaaa gttttggctt ttttctttag    1320
aaaccggcca cctgcttccc ccgcggggc cgctggagga agggcagccg acccggccgc    1380
tgggggaagt gccaggggcc cggggcaccc tgcgtttagg ctgggtccac tcttcttctt    1440
tttcgttcct tttatttaag tcttttttatt taataaaaaa gttagctatt tcaaaaaaaa    1500
aaaaaaaaaa aaa    1513

<210> SEQ ID NO 19
<211> LENGTH: 3213
<212> TYPE: DNA
<213> ORGANISM: Homo sapiens

<400> SEQUENCE: 19
ggagcctgcc gctccccgcg ctcgtagcgc gggcctgggg actggggatc ccgccgccgg     60
gccgcagcat ggggcgcttc cgcggggggcc tgcggtgcat caagtacctg ctgcttggct    120
tcaacctgct cttctggctg ctggatcgg ccgtcattgc ttttggacta tggtttcggt    180
tcggaggtgc cataaaggag ttatcatcag aggacaagtc cccagagtat ttctatgtgg    240
ggctgtatgt tctggttgga gccggggccc tgatgatggc cgtggggttc ttcgggtgct    300
gcggagccat gcgggagtcg caatgtgtgc ttggatcatt ttttacctgc ctcctggtga    360
tatttgctgc tgaagtaacc actggagtat ttgctttttat aggcaagggg gtagctatcc    420
gacatgttca gaccatgtat gaagaggctt acaatgatta ccttaaagac aggggaaaag    480
gcaatgggac actcatcacc ttccactcaa catttcagtg ctgtggaaaa gaaagctccg    540
aacaggtcca acctacatgc ccaaaggagc ttctaggaca caagaattgc atcgatgaaa    600
ttgagaccat aatcagtgtt aagctccagc tcattggaat tgtcggtatt ggaattgcag    660
gtctgacgat ctttggcatg atattcagca tggtcctctg ctgtgcgata cgaaactcac    720
gagatgtgat atgaagctac ttctacatga aaattgcaat ctaaagcttt cataccaaat    780
gtcacaggag ctgtctccca gctcattttt aacactgaaa tgacattagg atctaaaata    840
atttgctgtc aattgtacat ttgcatgagt acgtatgttt ggctcattac tggtttaccc    900
cttgagtgaa tgcctgttta tgatgactga gagcatattc atgtgtgatc tgcgtgtttc    960
```

```
tggaatatgc tttatacgta atgaaatctg tttgctggga attcctgatt cttgttatat    1020
aagaagaaca acctatttcg ctcccagaaa aaaaagatca aagagctttc agaaactttg    1080
agaacttggc tatttagaaa aagtgataat gggtcagttt ctcagactgt agccattgaa    1140
aattagatgc agagaattca gagatttctt cttaatggaa gtaataagct gtaagaattg    1200
agagatcaca atggagtgtt aaaactgact gtgtctaagt tgggtgtaag ggtttcctgg    1260
gtttttttat atacatgctc tccccagaat acagtaaacc acagttttag aactaaacac    1320
atctgtaaaa ctaaatatag catggaaaat ccaatttgaa taagtcatgc tttcctagaa    1380
tttaaaaata aaaagtcttt cctctggaaa gagaagtcac acagacaatc atgtgcccta    1440
taaaagtgag tgtttatagg actaaaaaac ttttaacaac ttttttaagga aatattttg     1500 ttcttataca aaaacatgta aatattgctt tattactttc attttctgac cctgctgtaa    1560
actactgcaa ccctcacatc ctcaaaggga cttttatgtc aaactcttct gtttctccaa    1620
atataaggaa aaaagactaa agcaagagat ctggcagttg aaaattgtgg gaaagagaat    1680
ttgtatgggc actgtatcta tgaaatacct cataacttac gtttacatgt tttcctaact    1740
ttttgtattt tcttgtata gccacctaga gaattcttca tagattaaga actacagttt     1800
tcaccactta acataagtaa aacaaagtcc ttcataattt aaccattagc atctttggcc    1860
aaaccaaaat aaagaaaagc atcttctcct agttgtgtgt gggcaacaga aacaagttaa    1920
ggaaacaaaa atacttatat atacacagaa caaaaataat gttcttttta tgcaaatccc    1980
ctgtgaaaat aaaattttca atgttttttt ggtcttaacg cttcatttta acttagtaaa    2040
cccaaattta ggatttacat tggcaaattt ttcagtgatt tttaacgtgt tacatttagt    2100
aaaccataga ttttttaaaa actacatttt gtaaggccac acataagtga aaatacggaa    2160
ggctttggaa accccagat gaacttctat acatgtgaaa acacaagtct ttgagtgtgc     2220
actaaaagtg tcacactccc aaaaaactca caaaacattt tgctaaaaag atatgactgc    2280
ttgaaatagt ctctctccca tggagaacca catttctctt tctgccatac ttgctactgc    2340
tactgatttt ggaggaaatt tttctagaag aacaaggtc atatttgagg caagctaaaa     2400
acttaattat acatggctac tttactgtgt ctgtagctaa agaaaaatta ttttacaaaa    2460
attacttcat gaaatatagt ttgtaccccca gtagttgaga atgtgacct tttaggcaaa     2520 gaacaggcag tccatctctc ttagctttag tttatctctc tgcctgaaga caggaaacag    2580
gcccaagtgc atactcgggt tctttccaac tcagaatcat ctctgattcc acaaaagtga    2640
gtttagtttc ctatctgaat taacaacttt aaaggagact ataatagtta aaagtggaag    2700
aatagaaata aataaattta aaatgaaatt aattaaagta gaagagaagg gttctgttcc    2760
atgtacgatt aatgtgcccc ttttggagat aagctttcca aaatatgcgt atgagtaaaa    2820
ttagagaatt ccaccactaa gcaacaatag attttatatg tgtgtgtgga tatatataca    2880
cacacacaca gaaagatgaa tatatatata tatatatctg tatagacaca catataatat    2940
atatagatat ataatcccta tatatcttga atctacaaat atctttatat gtatataatt    3000
tgaatatata catgtatgta tatacagatg tgtgtgtata tatatatata catacacata    3060
tacataaatt ttcagctatt tctgttcccc tgaactaatt tgagattaga cccaaacatg    3120
cttttaaatg tctcatgcca aggcactgaa ttaagacttc ttaatgttga aatattttaa    3180
gtgatttcat attaaatttt ctatatactg aaa                                 3213
```

<210> SEQ ID NO 20
<211> LENGTH: 508

```
<212> TYPE: DNA
<213> ORGANISM: Homo sapiens

<400> SEQUENCE: 20
tttggtgctt tggatccatt tccatcggtc cttacagccg ctcgtcagac tccagcagcc      60
aagatggtga agcagatcga gagcaagact gcttttcagg aagccttgga cgctgcaggt     120
gataaacttg tagtagttga cttctcagcc acgtggtgtg ggccttgcaa aatgatcaag     180
cctttctttc attccctctc tgaaaagtat tccaacgtga tattccttga agtagatgtg     240
gatgactgtc aggatgttgc ttcagagtgt gaagtcaaat gcatgccaac attccagttt     300
tttaagaagg gacaaaaggt gggtgaattt tctggagcca ataaggaaaa gcttgaagcc     360
accattaatg aattagtcta atcatgtttt ctgaaaatat aaccagccat tggctattta     420
aaacttgtaa ttttttaat ttacaaaat ataaaatatg aagacataaa cccagttgcc      480
atctgcgtga caataaaaca ttaatgct                                        508

<210> SEQ ID NO 21
<211> LENGTH: 2004
<212> TYPE: DNA
<213> ORGANISM: Homo sapiens

<400> SEQUENCE: 21
aacatttcag ccggtgggtg gcggggatta ggcgtgaagc ggttcagcag gcagaggttc      60
tcggacgccc tccggcgaag ccacctgttg atgcttttga ctttctgtcc ttgttcctcg     120
tcccatctgg agcatttcca attctggttt tgcggagcag caggtctgag cttgtccggc     180
gagggtggga gttggtcccg gcggagatcc agtgggaaga gccggcggct gcccgggcaa     240
ctcccccact ggaaaggatt ctgaaagaaa tgaagtcagc cctcagaaat gaagttgact     300
gcctgctggc tttctgttga ctggcccgga gctgtactgc aagacccttg tgagcttccc     360
tagtctaaga gtaggatgtc tgctgaagtc atccatcagg ttgaagaagc acttgataca     420
gatgagaagg agatgctgct cttttttgtgc cgggatgttg ctatagatgt ggttccacct     480
aatgtcaggg accttctgga tattttacgg gaaagaggta agctgtctgt cggggacttg     540
gctgaactgc tctacagagt gaggcgattt gacctgctca acgtatctt gaagatggac     600
agaaaagctg tggagaccca cctgctcagg aaccctcacc ttgtttcgga ctatagagtg     660
ctgatggcag agattggtga ggatttggat aaatctgatg tgtcctcatt aattttcctc     720
atgaaggatt acatgggccg aggcaagata agcaaggaga gagtttctt ggaccttgtg      780
gttgagttgg agaaactaaa tctggttgcc ccagatcaac tggattatt agaaaaatgc     840
ctaaagaaca tccacagaat agacctgaag acaaaaatcc agaagtacaa gcagtctgtt     900
caaggagcag ggacaagtta caggaatgtt ctccaagcag caatccaaaa gagtctcaag     960
gatccttcaa ataacttcag gctccataat gggagaagta agaacaaag acttaaggaa     1020
cagcttggcg ctcaacaaga accagtgaag aaatccattc aggaatcaga agcttttttg    1080
cctcagagca tacctgaaga gagatacaag atgaagagca agcccctagg aatctgcctg    1140
ataatcgatt gcattggcaa tgagacagag cttcttcgag acaccttcac ttccctgggc    1200
tatgaagtcc agaaattctt gcatctcagt atgcatggta tatcccagat tcttggccaa    1260
tttgcctgta tgcccgagca ccgagactac gacagctttg tgtgtgtcct ggtgagccga    1320
ggaggctccc agagtgtgta tggtgtggat cagactcact cagggctccc cctgcatcac    1380
atcaggagga tgttcatggg agattcatgc ccttatctag cagggaagcc aaagatgttt    1440
```

| | |
|---|---:|
| tttattcaga actatgtggt gtcagagggc cagctggagg acagcagcct cttggaggtg | 1500 |
| gatgggccag cgatgaagaa tgtggaattc aaggctcaga agcgagggct gtgcacagtt | 1560 |
| caccgagaag ctgacttctt ctggagcctg tgtactgcgg acatgtccct gctggagcag | 1620 |
| tctcacagct caccatccct gtacctgcag tgcctctccc agaaactgag acaagaaaga | 1680 |
| aaacgcccac tcctggatct tcacattgaa ctcaatggct acatgtatga ttggaacagc | 1740 |
| agagtttctg ccaaggagaa atattatgtc tggctgcagc acactctgag aaagaaactt | 1800 |
| atcctctcct acacataaga aaccaaaagg ctgggcgtag tggctcacac ctgtaatccc | 1860 |
| agcactttgg gaggccaagg agggcagatc acttcaggtc aggagttcga gaccagcctg | 1920 |
| gccaacatgg taaacgctgt ccctagtaaa aatacaaaaa ttaaaaaaaa aaaaaaaaaa | 1980 |
| aaaaaaaaaa aaaaaaaaaa aaaa | 2004 |

<210> SEQ ID NO 22
<211> LENGTH: 7134
<212> TYPE: DNA
<213> ORGANISM: Homo sapiens

<400> SEQUENCE: 22

| | |
|---|---:|
| cgggcttgtg ccgccgccgc cgccgccgcc gcccgggcca agtgacaaag gaaggaagga | 60 |
| agcgaggagg agccggcccc gcagccgctg acagggctct gggctggggc aaagcgcgga | 120 |
| cacttcctga gcgggcaccg agcagagccg aggggcggga gggcggccga gctgttgccg | 180 |
| cggacggggg agggggcccc gagggacgga agcggttgcc gggttcccat gtccccggcg | 240 |
| aatggggaac agtcgaggag ccgctgcctg gggtctgaag ggagctgcct ccgccaccgc | 300 |
| catggccgct ggatccagcc gccgcctgca gctgctcctg gcgcaatgag gagaggagcc | 360 |
| gccgccaccg ccaccgcccg cctctgactg actcgcgact ccgccgccct ctagttcgcc | 420 |
| gggcccctgc cgtcagcccg ccggatcccg cggcttgccg gagctgcagc gtttcccgtc | 480 |
| gcatctccga gccaccccct ccctccctct ccctccctcc tacccatccc cctttctctt | 540 |
| caagcgtgag actcgtgatc cttccgccgc ttcccttctt cattgactcg gaaaaaaaat | 600 |
| ccccgaggaa aatataatat tcgaagtact cattttcaat caagtatttg cccccgtttc | 660 |
| acgtgataca tattttttta ggatttgccc tctcttttct ctcctcccag gaaagggagg | 720 |
| ggaaagaatt gtattttttc ccaagtccta aatcatctat atgttaaata tccgtgccga | 780 |
| tctgtcttga aggagaaata tatcgcttgt tttgtttttt atagtataca aaaggagtga | 840 |
| aaagccaaga ggacgaagtc ttttctcttt tcttctgtgg gagaacttaa tgctgcattt | 900 |
| atcgttaacc taacacccca acataaagac aaaaggaaga aaaggaggaa ggaaggaaaa | 960 |
| ggtgattcgc gaagagagtg atcatgtcag ggcggcccag aaccacctcc tttgcggaga | 1020 |
| gctgcaagcc ggtgcagcag ccttcagctt ttggcagcat gaaagttagc agagacaagg | 1080 |
| acggcagcaa ggtgacaaca gtggtggcaa ctcctgggca gggtccagac aggccacaag | 1140 |
| aagtcagcta tacagacact aaagtgattg gaaatggatc atttggtgtg gtatatcaag | 1200 |
| ccaaactttg tgattcagga gaactggtcg ccatcaagaa agtattgcag gacaagagat | 1260 |
| ttaagaatcg agagctccag atcatgagaa agctagatca ctgtaacata gtccgattgc | 1320 |
| gttatttctt ctactccagt ggtgagaaga agatgaggt ctatcttaat ctggtgctgg | 1380 |
| actatgttcc ggaaacagta tacagagttg ccagacacta tagtcgagcc aaacagacgc | 1440 |
| tccctgtgat ttatgtcaag ttgtatatgt atcagctgtt ccgaagttta gcctatatcc | 1500 |
| attcctttgg aatctgccat cgggatatta accgcagaa cctcttgttg gatcctgata | 1560 |

```
ctgctgtatt aaaactctgt gactttggaa gtgcaaagca gctggtccga ggagaaccca    1620
atgtttcgta tatctgttct cggtactata gggcaccaga gttgatcttt ggagccactg    1680 attataccte tagtatagat gtatggtctg ctggctgtgt gttggctgag ctgttactag    1740
gacaaccaat atttccaggg gatagtggtg tggatcagtt ggtagaaata atcaaggtcc    1800
tgggaactcc aacaagggag caaatcagag aaatgaaccc aaactacaca gaatttaaat    1860
tccctcaaat taaggcacat ccttggacta aggattcgtc aggaacagga catttcacct    1920
caggagtgcg ggtcttccga ccccgaactc caccggaggc aattgcactg tgtagccgtc    1980
tgctggagta tacaccaact gcccgactaa caccactgga agcttgtgca cattcatttt    2040
ttgatgaatt acgggaccca aatgtcaaac taccaaatgg gcgagacaca cctgcactct    2100
tcaacttcac cactcaagaa ctgtcaagta atccacctct ggctaccatc cttattcctc    2160
ctcatgctcg gattcaagca gctgcttcaa cccccacaaa tgccacagca gcgtcagatg    2220
ctaatactgg agaccgtgga cagaccaata atgctgcttc tgcatcagct tccaactcca    2280
cctgaacagt cccgagcagc cagctgcaca ggaaaaacca ccagttactt gagtgtcact    2340
cagcaacact ggtcacgttt ggaaagaata ttaaaaagag aaaaaaatcc tgttcatttt    2400
agtgttcaat ttttttatta ttattgttgt tcttatttaa ccttgtaaaa tatctataaa    2460
tacaaaccaa tttcattgta ttctcacttt gagggagatc caggggggtgg gaggggttgt    2520 gggggagggg aaagcggagc actagaacat acaatctctc tcccacgaca atctttttt    2580 attaaaagtc tgctgttgta tactttaaaa acaggactcc tgcctcatgc cccttccaca    2640
aaagaagaaa accttttcct gtgctgatgg gttttttga actttgtttt cttttaaagt    2700
ctagtgtgag actttggtat agtgcacagc ttgaaattgg ttgggagctt agcaggtata    2760
actcaacggg gacttaaatg tcacttgtaa aattaatcca tatcttcggg tatttataga    2820
cttgcctttg gcatgttggt ggcaggtgtg gcagacaaag aaatgtgtat cattcgtaac    2880
ccagggaggt caataaagtt tggaactcta cagggaagat tcttagtaga tttgttaagg    2940
ttttgttttg ctctcagtta gtgctagtga tgtagaggct tgtacaggag gctgccagag    3000
gggaagcagc aagcaagact caggcacaca tgctctacag gtggctcttt gtttgcctga    3060
ccaaagttct ttgcaaatct tagcacagtt tcaaactagt gacctgggag gagatggaag    3120
gggtgttgag caggctgagc tagctgctga ggtcaaaggc tgatgagccc agaggaaggg    3180
gacaggtcag ggatacatct caccactgtg aataagtttg tccagatttt tttctaaagt    3240
tacttcccct tggaaagatac acttgagagg acattgtagt taaataatgt gaactgtaac    3300
agtcatctac tggtttattt ttcatatttt ttaattgaaa attgagcttg cagaaatagc    3360
cacattctac acatagttct aattttaaat ccaaatctag aatctgtatt taatttgttt    3420
tttaacctca tgcttttac atttatttat tgatgcatgt cagatggtag aaatattaaa    3480
aactacacat cagaatgata cagtcactta tacctgctga ctttatagga aagctgatga    3540
tataaatgtg tgtatatatg ttatatatac atatattcaa tactgccttt ttttttgtct    3600
acagtatcaa aattgactgg ttgaagcatg agaagaatgt ttcccccaca cccagttaag    3660 agttttgtg tctgttttct ttgtgtatca gtgaacgatg ttaagaatca gtctctcttt    3720
ttgaagaaaa agcaatattc cttggaaagc aaggagaatt gaaggactat gtttgccgtg    3780
aggaaataga ttttcatgac tagtttgttt tatactttta aggttggcat ctatgtgggc    3840
cttatatact ctaaaatgaa ctttagtcac cttggtgctt atgggccatt acttgaccta    3900
```

```
tgaatcttta aggcacaatc agttgtactt tacatttaaa gatcacttga gtgatggccg    3960 ccttccctc ctacccgctc cttccccaca tgccttccaa ggttagctgg taactgtagg     4020
gctgcagagc tgagcccatg gttgtgtgta acttgccctc accctcctca ttgccacctt    4080
aggtcacttt atgggtctcg tcctccagag ggttcggaag tggagtctgt tggcagccct    4140
cctgcaggcc ctagcaccct gtcctgctcc ttaactgtgt gtgtgactct ccaagagagt    4200
tgtcctgcct gctgaagtga accagtaccc agaaagacaa ctgtgagcca tcttggtttt    4260
cactcgctgt ttagctgagg tcttgggcca caaaggggt ttcacaaacc tctggatata    4320
tcagagttta tgagaaagga aacatgctca gtcaaaccaa atcaaacaaa ttgaatttta    4380
tgttttataa agtgcttctg aaagctaaga tttgaaagaa gtctgaaatc aaagtatttg    4440
gcagcataac tccttaaagg tagtggcgtt gatagaccat tttcagacag aatttataaa    4500
gaatctgaaa aggcaggtct gtgatagaga atggacctg cattcagatc caactgccca     4560
gcaagcgttt ggatgcagac actgctctgg acgtggtata ctccccagag tccataaaaa    4620
tcagtgctta ttttaggaaa caggttgccc cccacaactg gggtaaaaga agagagaaaa    4680
gtcacgcttt tctctcattt cattgtgtgt gcatgtgtgc gtgtgtgtgt gtgtgtgtgt    4740
gtgctgagat gtgtgatttt tctttctcaa ggatcatggt gggatcacag aactcttta     4800 tacaagtgag atccaggtct ctgaatatct ttttgtatat aataataata aaaagctcct    4860
caccaaattc aagcttgtac attatatttt ctttctgtgt ttttaaattt aagttttatt    4920
gttttgtatg taaatatgtg gacccaggaa ctgttattaa tgagcaaaaa gttactgttc    4980
agggcagtga ttctgtttaa taatcagaca aaatgtagac gagcttttta aagccatata    5040
gttttaactc tgtacagtag gtaccggcct gtattattgt aacaataact ctagcaatgt    5100
atagtgtatc tatatagttt ggagtgcctt cgcttccatg tgttttttt tttaatttgt     5160 tcttttttaa attttaattg gtttccttta tccatgtctc cctgtccacc ccctttccct    5220
ttgaaataat aactcactca taacagtatc tttgcccctt ccacagttaa gtttcagtga    5280
taccatactc aggagtggga agaggaaatc atattcgtaa tttcatttcg ttgaagccct    5340
gcctttgttt tggttctgaa tgtctttcct cctcggtagc agtgagaccg gtttcatttc    5400
atacttagtc cattcaggga cttagtgtag caccagggag ccctagagct ggaggatatc    5460
gaatagatta aattttgctc gtctcttcca caagccctaa ccatgggtct taaaacagc     5520 agattctggg agccttccat gctctctctc tctcctcttt tatctacttc cctcccaaat    5580
gagagagtga cagagaattg ttttttata aatcgaagtt tcttaatagt atcaggtttt     5640
gatacgtcag tggtctaaaa tgctatagtg caattactag cagttactgc acggagtgcc    5700
accgtgccaa tagaggactg ttgttttaac aagggaactc ttagcccatt tcctccctcc    5760
cgccatctct acccttgctc aatgaaatat cattttaatt tcttttaaaa aaaatcagtt    5820
taattcttac tgtgtgccca acacgaaggc ctttttgaa agaaaaatag aatgttttgc     5880
ctcaaagtag tccatataaa atgtcttgaa tagaagaaaa aactaccaaa ccaaaggtta    5940
ctatttttga aacatcgtgt gttcattcca gcaaggcaga agactgcacc ttctttccag    6000
tgacatgctg tgtcatttt tttaagtcct cttaattttt agacacattt ttggtttatg     6060
ttttaacaat gtatgcctaa ccagtcatct tgtctgcacc aatgcaaagg tttctgagag    6120
gagtattctc tatccctgtg gatatgaaga cactggcatt tcatctattt ttcccttttc   6180 ttttttaaagg atttaacttt ggaatcttcc aaaggaagtt tggccaatgc cagatcccca   6240
ggaatttggg gggttttctt tcttttcaac tgaaattgta tctgattcct actgttcatg    6300
```

```
ttagtgatca tctaatcaca gagccaaaca cttttctccc ctgtgtggaa aagtaggtat    6360
gctttacaat aaaatctgtc ttttctggta gaaacctgag ccactgaaaa taaaagagac    6420
aactagaagc acagtagagt cccagactga gatctacctt tgagaggctt tgaaagtaat    6480
ccctggggtt tggattattt tcacaagggt tatgccgttt tattcaagtt tgttgctccg    6540
ttttgcacct ctgcaataaa agcaaaatga caaccagtac ataaggggtt agcttgacaa    6600
agtagacttc cttgtgttaa ttttttaagtt ttttttttcct taactatatc tgtctacagg   6660
cagatacaga tagttgtatg aaaatctgct tgcctgtaaa atttgcattt ataaatgtgt    6720
tgccgatgga tcacttgggc ctgtacacat accaattagc gtgaccactt ccatcttaaa    6780
aacaaaccta aaaacaaaa tttattatat atatatatat atatatataa aggactgtgg     6840
gttgtataca aactattgca aacacttgtg caaatctgtc ttgatataaa ggaaaagcaa    6900
aatctgtata acattattac tacttgaatg cctctgtgac tgatttttttt ttcattttaa   6960 atataaactt ttttgtgaaa agtatgctca atgtttttttt tccctttccc cattcccttg   7020
taaatacatt ttgttctatg tgacttggtt tggaaatagt taactggtac tgtaatttgc    7080
attaaataaa aagtaggtta gcctggaaat gaaattaaaa aaaaaaaaaa aaaa          7134

<210> SEQ ID NO 23
<211> LENGTH: 523
<212> TYPE: DNA
<213> ORGANISM: Homo sapiens

<400> SEQUENCE: 23 cggaagttttt gctgctagtc gcggacgcaa tggcttcaag gttacttcgc ggagctggaa     60
cgctggccgc gcaggccctg agggctcgcg gccccagtgg cgcggccgcg atgcgctcca    120
tggcatctgg aggtggtgtt cccactgatg aagagcaggc gactgggttg agagggagga   180
tcatgctggc tgcaaagaag ggactggacc catacaatgt actggcccca aagggagctt    240
caggcaccag ggaagaccct aatttagtcc cctccatctc caacaagaga atagtaggct    300
gcatctgtga agaggacaat accagcgtcg tctggttttg gctgcacaaa ggcgaggccc    360
agcgatgccc ccgctgtgga gcccattaca agctggtgcc ccagcagctg gcacactgag    420
cacctgcact aaattactca aaatgtgctg taaagtttct tctttccagt aaagactagc    480
cattgcattg gctccttctc ccataaaaaa aaaaaaaaa aaa                        523

<210> SEQ ID NO 24
<211> LENGTH: 3788
<212> TYPE: DNA
<213> ORGANISM: Homo sapiens

<400> SEQUENCE: 24
gcgcgggcgc gcgcggcggc ggcgcgttcc gttccgggcc gaggctcgcg gcggaaaagt      60
tgcggggcat agacgagcgg ccccgggacg ggcagctagc gcgaccctga gccggcgccc    120
gtggtccggc catggacgac ctcgacgccc tgctggcgga cttggagtct accacctccc    180
acatctccaa acggcctgtg ttcttgtcgg aggagacccc ctactcatac ccaactggaa    240
accacacata ccaggagatt gccgtgccac ccccgtcccc ccaccccg tccagcgagg      300 ccctcaatgg cacaatcctt gaccccttag accagtggca gcccagcagc tcccgattca    360
tccaccagca gcctcagtcc tcatcacctg tgtacggctc cagtgccaaa acttccagtg    420
tctccaaccc tcaggacagt gttggctctc cgtgctcccg agtgggtgag gaggagcacg    480
```

```
tctacagctt ccccaacaag cagaaatcag ctgagccttc acccaccgta atgagcacgt    540
ccctgggcag caacctttct gaactcgacc gcctgctgct ggaactgaac gctgtacagc    600
ataacccgcc aggcttccct gcagatgagg ccaactcaag ccccccgctt cctgggccc     660
tgagccccct ctatggtgtc cagagacta acagccctt gggaggcaaa gctgggcccc     720
tgacgaaaga gaagcctaag cggaatgggg gccggggcct ggaggacgtg cggcccagtg    780
tggagagtct cttggatgaa ctggagagct ccgtgcccag ccccgtccct gccatcactg    840
tgaaccaggg cgagatgagc agcccgcagc gcgtcacctc acccaacag cagacacgca     900
tctcggcctc ctctgccacc agggagctgg acgagctgat ggcttcgctg tcggatttca    960
agatccaggg cctggagcaa agagcggatg gggagcggtg ctgggcggcc ggctggcctc   1020
gggacggcgg gcggagcagc cccggagggc aggacgaggg agggttcatg gcccagggga   1080
agacagggag cagctcaccc cctgggggc cccgaagcc cgggagccag ctggacagca     1140
tgctggggag cctgcagtct gacctgaaca agctgggggt cgccacagtc gccaaaggag   1200
tctgcggggc ctgcaagaag cccatcgccg ggcaggttgt gaccgccatg gggaagacgt   1260
ggcaccccga gcacttcgtc tgcacccact gccaggagga gatcggatcc cggaacttct   1320
tcgagcggga tggacagccc tactgtgaaa aggactacca caacctcttc tccccgcgct   1380
gctactactg caacggcccc atcctggata aagtggtgac agcccttgac cggacgtggc   1440
accctgaaca cttcttctgt gcacagtgtg gagccttctt tggtcccgaa gggttccacg   1500
agaaggacgg caaggcctac tgtcgcaagg actacttcga catgttcgca cccaagtgtg   1560
gcggctgcgc ccgggccatc ctggagaact atatctcagc cctcaacacg ctgtggcatc   1620
ctgagtgctt tgtgtgccgg gaatgcttca cgccattcgt gaacggcagc ttcttcgagc   1680
acgacgggca gccctactgt gaggtgcact accacgagcg gcgcggctcg ctgtgttctg   1740
gctgccagaa gcccatcacc ggccgctgca tcaccgccat ggccaagaag ttccacccg    1800
agcacttcgt ctgtgccttc tgcctcaagc agctcaacaa gggcaccttc aaggagcaga   1860
acgacaagcc ttactgtcag aactgcttcc tcaagctctt ctgctaggtg ccctgcccct   1920
gtctctgccc cccttcccca gccagcatcc ccaactgcga ctgtgaccta gagacttcac   1980
ccgggggtga agggtaaac ccgactgaaa ctggaaccct tgtcctccgc tggtgcggga    2040
tggacagagg gccgtgaggg gtccccctgc ttgtcttcac ccctgccaga gcctctgggc   2100
cccctcctcc ctcctgtagc tctccctagg ctgcccactc tccatcctcc caggggtag    2160
aggctggggg ctccacccca gcccatgtac gtccccacga actggcctgg ccagcacccc   2220
acactggagc catctcttcc tcatatttca gcagtgcagc cgggggcag ggaagggcag    2280
gcagggtctg ttggggtctc ttttatcct tattcctccc ccgacctaat tgtctttgtt    2340
ctgtgattat tggggacac ccggctccct ccagacaatg ccagcataaa tccatccatc    2400
caaaggcaga gaaccaaagg ggccatggaa ggttctctgt gctcctccta cccttccagt   2460
gccctaggcc tggcgactgc ccctgccttt tagacccgcc ctcccctttt atacctgctc   2520
ttgttctact gagaaaagcc tctccagcaa taatgtttc tagtcacttc ctccgtctcc    2580
gggacggcgt gcctggacac tgtaccgact ttgatagatt tctacactga ggtttgaatt   2640
catatcgcct gagttgcttt tacttctcta tacaaaatga ttttgaagag attttaaaga   2700
cgttcccttt tgtattctct tcctcatcca ccgccactgg gcctgtcact gatggtggct   2760
ctggtgtgaa gtttgctttg tactgagggt tggggtgggg aagcaatttg tattttattg   2820
tttcttagca caagcaggtg aactgggagc agctctgtga ctcccccctct ttcacttcat   2880
```

```
agctcaccag gactgtttta taaactgctg tatttggaaa cccttctttt acttcccagg    2940
ccagcaagct cttcactgaa actggttgaa gggtgttgca cccttttggg cctagaattc    3000
tgaactttat ctgttctgtt tctgtgggag gagaagggga agtatgtttt gggggggctgc   3060 ttcctgtctg agtaagccct caggagcctc tgctcccctg tgaacccact gaaccttctg    3120
agcccccact gcttctatgg ggctctctct tctgccttct caggaaagct ggtgtctgat    3180
tttggccatc aggactctga cgtctctttg gtcttgttga tttcctctgg gcatatccct    3240
tccccagatc tgctcctccc ctttcacagg tgggatcggc actcaggggg tctggaaaga    3300
aggtcataag ggagcatgat aggatttggg gcagagggac aggctcctct ggggaaaccc    3360
cccagagctc tttaccaagg atgaaagagg agccaggcct tgggctcctg atgaggagaa    3420 aggggccca ccgggtcta atggtgacag tccaaaccac tccactggcc tcctggcaga     3480
agccgagtgt gctgggtct ccgaagaggg tccctccttt ttgggggaag gtcagcccag     3540
cccctccaaa ggtctgatgt ctccactttc acccgcaggc cttaccgctc tgtttatagt    3600
gacccaccct agatcttccc caagagggac tgggtttct ggggtccatt ctctgagtca     3660
gtggttattt gaaaatttga ttttgatttt attttttctc tgtaaacttc caagctggct    3720
tttcccattt caattcctgt gatttatgcc aataaagttt gcccatgatt ttcaaaaaaa    3780
aaaaaaaa                                                              3788

<210> SEQ ID NO 25
<211> LENGTH: 2689
<212> TYPE: DNA
<213> ORGANISM: Homo sapiens

<400> SEQUENCE: 25
cggaggagca gcgagtcaag atgagagttc agccgcggcg gcagcagcag cagactggaa      60
aagtaagaag agctttcctg ccttttaat taccaaacta ctctcagttt tcaatgaatc      120
agttcaaaga aagaatgcag tctttctata cctgactcaa gaatgaacaa tccgtcagaa     180
accagtaaac catctatgga gagtggagat ggcaacacag gcacacaaac caatggtctg     240
gactttcaga agcagcctgt gcctgtagga ggagcaatct caacagccca ggcgcaggct     300
ttccttggac atctccatca ggtccaactc gctgaacaa gtttacaggc tgctgctcag      360
tctttaaatg tacagtctaa atctaatgaa gaatcggggg attcgcagca gccaagccag    420
ccttcccagc agccttcagt gcaggcagcc attccccaga cccagcttat gctagctgga    480
ggacagataa ctgggcttac tttgacgcct gcccagcaac agttactact ccagcaggca    540
caggcacagg cacagctgct ggctgctgca gtgcagcagc actccgccag ccagcagcac    600
agtgctgctg gagccaccat ctccgcctct gctgccacgc ccatgacgca gatccccctg    660
tctcagccca tacagatcgc acaggatctt caacaactgc aacagcttca acagcagaat    720
ctcaacctgc aacagtttgt gttggtgcat ccaaccacca atttgcagcc agcgcagttt    780
atcatctcac agacgcccca gggccagcag ggtctcctgc aagcgcaaaa tcttctaacg    840
caactacctc agcaaagcca agccaacctc ctacagtcgc agccaagcat caccctcacc    900
tcccagccag caacccccaac acgcacaata gcagcaaccc caattcagac acttccacag    960
agccagtcaa caccaaagcg aattgatact cccagcttgg aggagcccag tgaccttgag   1020
gagcttgagc agtttgccaa gaccttcaaa caaagacgaa tcaaacttgg attcactcag   1080
ggtgatgttg ggctcgctat ggggaaacta tatggaaatg acttcagcca aactaccatc    1140
```

| | |
|---|---|
| tctcgatttg aagccttgaa cctcagcttt aagaacatgt gcaagttgaa gccactttta | 1200 |
| gagaagtggc taaatgatgc agagaacctc tcatctgatt cgtccctctc cagcccaagt | 1260 |
| gccctgaatt ctccaggaat tgagggcttg agccgtagga ggaagaaacg caccagcata | 1320 |
| gagaccaaca tccgtgtggc cttagagaag agtttcttgg agaatcaaaa gcctacctcg | 1380 |
| gaagagatca ctatgattgc tgatcagctc aatatggaaa agaggtgat tcgtgtttgg | 1440 |
| ttctgtaacc gccgccagaa agaaaaaaga atcaacccac caagcagtgg tgggaccagc | 1500 |
| agctcaccta ttaaagcaat tttcccagc ccaacttcac tggtggcgac cacaccaagc | 1560 |
| cttgtgacta gcagtgcagc aactaccctc acagtcagcc ctgtcctccc tctgaccagt | 1620 |
| gctgctgtga cgaatctttc agttacaggc acttcagaca ccacctccaa caacacagca | 1680 |
| accgtgattt ccacagcgcc tccagcttcc tcagcagtca cgtcccctc tctgagtccc | 1740 |
| tccccttctg cctcagcctc cacctccgag gcatccagtg ccagtgagac cagcacaaca | 1800 |
| cagaccacct ccactccttt gtcctcccct cttgggacca gccaggtgat ggtgacagca | 1860 |
| tcaggtttgc aaacagcagc agctgctgcc cttcaaggag ctgcacagtt gccagcaaat | 1920 |
| gccagtcttg ctgccatggc agctgctgca ggactaaacc caagcctgat ggcaccctca | 1980 |
| cagtttgcgg ctggaggtgc cttactcagt ctgaatccag ggaccctgag cggtgctctc | 2040 |
| agcccagctc taatgagcaa cagtacactg gcaactattc aagctcttgc ttctggtggc | 2100 |
| tctcttccaa taacatcact tgatgcaact gggaacctgg tatttgccaa tgcgggagga | 2160 |
| gccccccaaca tcgtgactgc ccctctgttc ctgaaccctc agaacctctc tctgctcacc | 2220 |
| agcaaccctg ttagcttggt tctgccgccc gcagcatctg cagggaactc tgcacctgta | 2280 |
| gccagccttc acgccaccct cacctctgct gagtccatcc agaactctct cttcacagtg | 2340 |
| gcctctgcca gcggggctgc gtccaccacc accaccgcct ccaaggcaca gtgagctggg | 2400 |
| cagagctggg ctgccagaag ccttttttcac tctgcagtgt gattggactg ccagccaggt | 2460 |
| taataaactg aaaaatgtga ttggcttcct ctcgccgtgt tgtgagggca aggagagaa | 2520 |
| gggagaaaaa aaaaaaaaaa ccacacacac ccatacacac ataccagaaa agaaagaaa | 2580 |
| ggatggagac ggaacatttg cctaattttg taataaaaca ctgtcttttc aggattgctt | 2640 |
| catggattgg agaactttct aaccaaaaat taaaaaaaaa aaaaaaaa | 2689 |

<210> SEQ ID NO 26
<211> LENGTH: 1958
<212> TYPE: DNA
<213> ORGANISM: Homo sapiens

<400> SEQUENCE: 26

| | |
|---|---|
| agcagccggc gcggccgcca gcgcggtgta gggggcaggc gcggatcccg ccaccgccgc | 60 |
| gcgctcggcc cgccgactcc cggcgccgcc gccgccactg ccgtcgccgc cgccgcctgc | 120 |
| cgggactgga gcgcgccgtc cgccgcggac aagaccctgg cctcaggccg gagcagcccc | 180 |
| atcatgccga gggagcgcag ggagcgggat gcgaaggagc gggacaccat gaaggaggac | 240 |
| ggcggcgcgg agttctcggc tcgctccagg aagaggaagg caaacgtgac cgttttttttg | 300 |
| caggatccag atgaagaaat ggccaaaatc gacaggacgg cgagggacca gtgtgggagc | 360 |
| cagccttggg acaataatgc agtctgtgca gaccctgct ccctgatccc cacacctgac | 420 |
| aaagaagatg atgaccgggt ttacccaaac tcaacgtgca gcctcggat tattgccaca | 480 |
| tccagaggct ccccgctgcc tgtactgagc tgggcaaata gagaggaagt ctggaaaatc | 540 |
| atgttaaaca aggaaaagac atacttaagg gatcagcact ttcttgagca acaccctctt | 600 |

```
ctgcagccaa aaatgcgagc aattcttctg gattggttaa tggaggtgtg tgaagtctat      660
aaacttcaca gggagacctt ttacttggca caagatttct tgaccggta tatggcgaca      720
caagaaaatg ttgtaaaaac tcttttacag cttattggga tttcatcttt atttattgca      780
gccaaacttg aggaaatcta tcctccaaag ttgcaccagt ttgcgtatgt gacagatgga      840
gcttgttcag gagatgaaat tctcaccatg gaattaatga ttatgaaggc ccttaagtgg      900
cgtttaagtc ccctgactat tgtgtcctgg ctgaatgtat acatgcaggt tgcatatcta      960
aatgacttac atgaagtgct actgccgcag tatccccagc aaatctttat acagattgca     1020
gagctgttgg atctctgtgt cctggatgtt gactgccttg aatttcctta tggtatactt     1080
gctgcttcgg ccttgtatca tttctcgtca tctgaattga tgcaaaaggt ttcagggtat     1140
cagtggtgcg acatagagaa ctgtgtcaag tggatggttc catttgccat ggttataagg     1200
gagacgggga gctcaaaact gaagcacttc agggcgtcg ctgatgaaga tgcacacaac      1260
atacagaccc acagagacag cttggatttg ctggacaaag cccgagcaaa gaaagccatg     1320
ttgtctgaac aaaatagggc ttctcctctc cccagtgggc tcctcacccc gcacagagc      1380
ggtaagaagc agagcagcgg gccggaaatg gcgtgaccac cccatccttc tccaccaaag     1440
acagttgcgc gcctgctcca cgttctcttc tgtctgttgc agcggaggcg tgcgtttgct     1500
tttacagata tctgaatgga agagtgtttc ttccacaaca gaagtatttc tgtggatggc     1560
atcaaacagg gcaaagtgtt ttttattgaa tgcttatagg ttttttttaa ataagtgggt     1620
caagtacacc agccacctcc agacaccagt gcgtgctccc gatgctgcta tggaaggtgc     1680
tacttgacct aagggactcc cacaacaaca aaagcttgaa gctgtggagg ccacggtgg     1740
cgtggctctc ctcgcaggtg ttctgggctc cgttgtacca agtggagcag gtggttgcgg     1800
gcaagcgttg tgcagagccc atagccagct gggcagggg ctgccctctc cacattatca     1860
gttgacagtg tacaatgcct ttgatgaact gtttttgtaag tgctgctata tctatccatt     1920
ttttaataaa gataatactg tttttgagac aaaaaaaa                             1958

<210> SEQ ID NO 27
<211> LENGTH: 6895
<212> TYPE: DNA
<213> ORGANISM: Homo sapiens

<400> SEQUENCE: 27
gtagatttgg ttgctgtgta cgtggaagaa gcaagcgcat gcgcacatgg gcccccttcg       60
tctcagctgt gcgggaacgg ccgagggtaa catcccgggc tcgcgggagg ctgtcggggt      120
aatggccaca cgctgacaga accagccgag tggaaaaggg gagcgaagcc gttcctctgc      180
accettcccc aggcctgagg ccttcccgct tggtgctgcc gccgccactg ccggctgagg      240
aggggcgatg agttggttca acgcctccca gctctccagc ttcgctaagc aggccctgtc      300
ccaggcccag aagtctattg acaggggttct ggacatccag gaagaggagc cgagcatctg      360
ggccgagacc attccgtatg agagccgggg aataagttcc cctgtcagtg gaggatggga      420
tacttcaacc tgggggttga atcaaacac tgaacctcag agtccaccaa tagcctctcc       480
taaagcaatc acaaagccag ttcggaggac tgtggtcgat gaatctgaaa atttcttcag      540
tgcctttctc tcgccaactg atgtccagac cattcagaag agtccagtgg tatcaaaacc      600
tccagcaaaa tcacaacgac cagaagaaga agtgaaaagc agcttacatg aatccttgca      660
cattggccag tcaagaactc ctgaaacaac tgaatcacaa gtaaaagact cttctttgtg      720
```

| | |
|---|---|
| tgtttcaggg gaaactctgg cagcaggtac ttcatcacct aaaactgaag gcaagcacga | 780 |
| agaaactgtt aataaagaat cggatatgaa ggtgccaact gtaagtttga aagtatctga | 840 |
| aagtgtaatt gatgtgaaaa caactatgga aagtatatct aatacgtcta cgcagtctct | 900 |
| cacagcagaa acaaggaca tagctttgga acctaaggaa caaaaacatg aagacaggca | 960 |
| gagcaataca ccttctcctc ctgttagtac cttttcatca ggtacttcta ccaccagtga | 1020 |
| tattgaagtt ttagatcatg aaagtgtaat aagtgagagc tcagcgagct cgagacaaga | 1080 |
| gactacagat tcaaaatcaa gtcttcactt gatgcagaca tcttttcagc ttctctctgc | 1140 |
| atctgcttgt cctgaatata atcgtttaga tgatttccaa aaactcactg agagttgctg | 1200 |
| ttcatctgat gcttttgaaa gaatagactc atttagtgta cagtcattag atagccggag | 1260 |
| tgtaagtgaa atcaattcag atgatgaatt gtcaggcaag ggatatgctt tagtgcctat | 1320 |
| tatagttaat tcttcaactc caaagtctaa aacagttgaa tctgctgaag gaaaatctga | 1380 |
| agaagtaaat gaaacattag ttatacccac tgaggaagca gaaatggaag aaagtggacg | 1440 |
| aagtgcaact cctgttaact gtgaacagcc tgatatcttg gtttcttcca caccaataaa | 1500 |
| tgaaggacag actgtgttag acaaggtggc tgagcagtgt gaacctgctg aaagtcagcc | 1560 |
| agaagcactt tctgagaagg aagatgtttg caagacagtt gaatttctga atgaaaagct | 1620 |
| ggaaaaaagg gaggctcagt tattatctct tagtaaggaa aaagcacttc tagaagaagc | 1680 |
| ttttgataac ctgaaagatg aaatgttcag agtgaaagaa gaaagcagta gcatttcttc | 1740 |
| cttgaaagat gagtttactc aaagaattgc agaagcagaa aagaaagttc aactagcctg | 1800 |
| caaagagaga gatgctgcta aaaggaaat caaaaacata aaagaagaac ttgccactag | 1860 |
| attaaatagt agtgaaactg cagacctttt gaaagagaaa gatgagcaga tccgagggtt | 1920 |
| aatgaagaa ggagaaaaac tttcaaaaca gcagctgcac aattctaaca tcatcaagaa | 1980 |
| attaagagct aaagacaagg agaatgaaaa tatggttgca aagctgaaca aaaaagttaa | 2040 |
| agagctagaa gaggagttgc agcatttgaa acaggtcctt gatggcaaag aagaggttga | 2100 |
| gaaacaacat agagaaaata ttaaaaaact aaattccatg gtagaacgcc aagagaaaga | 2160 |
| tcttggccgt cttcaggtag acatggatga acttgaagaa aagaaccgaa gtattcaggc | 2220 |
| tgccctggat agtgcataca aagaacttac tgatcttcac aaagccaatg ctgcaaagga | 2280 |
| tagtgaggca caggaagctg ctctgagccg tgaaatgaaa gctaaagaag aactttctgc | 2340 |
| agcattagag aaggcccaag aagaagcccg tcagcagcaa gaaacattag ccattcaagt | 2400 |
| gggggacctt aggcttgcat tgcagcgtac agaacaagcg gctgccagaa aggaggatta | 2460 |
| tttacgccat gagatcggtg aacttcagca gagactccag gaagcagaga tcgaaaccca | 2520 |
| ggaactgagt caaagtgttt catcaacaac aagaccattg cttcgacaaa tagaaaattt | 2580 |
| gcaagcaacc ctgggatccc agacatcgtc gtgggagaaa ttagagaaga atctttctga | 2640 |
| taggcttggt gaatcccaga ccttgctggc agcagcagtt gagagagaac gtgcagctac | 2700 |
| agaagaactc cttgctaaca aaattcagat gtcttccatg gagtcacaga attctctttt | 2760 |
| aagacaggaa aacagtagat ttcaagccca gctagaatca gagaaaaata ggctgtgtaa | 2820 |
| actggaggat gagaacaata ggtaccaggt tgaattggaa aacctaaaag atgaatatgt | 2880 |
| aagaacactt gaagagacga ggaaagaaaa gacattgttg aatagtcagt tagaaatgga | 2940 |
| aagaatgaaa gttgaacaag aaaggaagaa agccatttt actcaagaaa caataaaaga | 3000 |
| aaaggaacgc aagccatttt ctgtttctag cactcccacc atgtcacgct caagttcaat | 3060 |
| aagtggtgtt gatatggcag gactacagac atcttttctg tctcaggatg agtctcatga | 3120 |

```
tcactcattt ggaccaatgc ctatatcagc aaatggaagc aatctttatg atgctgtaag    3180
gatgggagca ggatcaagca taattgaaaa cctacagtct cagctaaagc taagggaagg    3240
ggaaatcact catttacagc tagaaattgg caatctagaa aaaactcgat caataatggc    3300
tgaagaacta gttaaattaa caaatcaaaa tgatgaactt gaagagaagg tgaaggagat    3360
acccaaactt agaactcagc taagagattt ggatcaaagg tacaacacta ttctgcagat    3420
gtatggagaa aaagcagaag aggcagaaga acttcgatta gatctcgaag atgtaaaaaa    3480
tatgtacaaa actcaaatag atgaactttt aagacaaagt ctcagttaac ttgtgaaaat    3540
tgaattccca tcaaactgaa tgtaagcatt taatatctaa acatttaatg tggacttcca    3600
ataaattctt ttatagaatt agaagtgggg atttactgta gagtgtaaaa atttttttaa    3660
aattgtttta cactatgtag taatatttac agttaaatta ttttgtgcaa tatttgaact    3720
ttatttttga aactattctt taaagattta tttttaaag cattcatttt ttttccttga    3780
atagcacaga gatttattac tttatcctca tataaatatg gctagagaag aagaatggtg    3840
ttcatatatg tattgtagat atacaactag ttgtatctat aatttgtaag tgtttatata    3900
tatattaaga acatttgaag agtaatgtta acatactgaa actttgaaat ctttcacatt    3960
taaaatttca acatatctta attactgctc atgaaaatgt acattaagtg ttaaagtaaa    4020
aaattattaa atctgtggct attaaatttt aaactaattt ttttcccttta aaagtaagag    4080 tcacactgac actgtctgaa attttaaagag tgaatgattt aaacttaaaa aaaattttga    4140
tctgaaaatt tatttcaccc agctttcaca attaagtctg tataaaatgt ggtacctttt    4200
ggtacctatc cagagaaacc tgtacatatt caatgttatc tagatgtgat tggataatgg    4260
agaaaattta tttataatga ttttgcaatg gcatcaataa catttaaatg attttgaaga    4320
agtattattt tactacccta taaatgaat cgaaataat aaagttctta acataattta    4380
ctctttaaaa attacctgtt catattttgt aaacccatat ttttagcaca ttaaaaatga    4440
atgtttgata ttacagaata ttcataacaa aatggaagaa ttataggaat taacttgaat    4500
ttggcatttt taattttgtg atttatcatt ttatttttc ttgaaatttc aaacacaagg    4560
aaagcataga atagcttta aaagtagcta tgccttcttc caaatgttat tttattcaaa    4620 aaggtaaacca ggttgtgttt taaacctgtg aaatattgtg atgcatttta ttactgaaag    4680
ttatttaact gcctttactt gcacataaaa actctcattt acggccaggt gctgtggctc    4740
atgcctgtaa tcccagcact ttgggaggcc aaggcgggca tatcacctga tgtcaggagt    4800
tcaagaccag catggccagc agtttggtga accccatctc tactaaaaaa tacaaaaatt    4860
agcctggcgt ggtggtgtgc gcctgtaatc ctagctactc gggaggctga ggcaggagca    4920
ttgcttgaac ctgggaggtg gaggttacaa tgagccaaga ttgtgccact gcactccagc    4980
atgggtgaca gagaaagact ccgtctcaaa aaaaaaaaa caaactctta tttaatttt    5040 agttaaaatt aaaacactag tacttcagaa tatagataca agtacaccat cttgaagaat    5100
ttggagtttt tcagggcaat tcaaatgacc tcatttttg ttcttttgt attccagaca    5160 gtgtttctgt cattggatct ctgattggta gtgttaataa atattctttc agtgtgagcc    5220
agattcataa aattaatttt cttcatttta gtagtaaaaa gtagtctaat agcttttgt    5280 cagcttgatt ttttgtgtg tgtaatattc aagggcagaa tgacaggaca gataagcaat    5340
aagaaatgta tagaattaga aaatatagta gttccctctt acccatggga catacgttcc    5400
aagaccccca gtgaacgtct gaaaccatgg atagtataga cacctctata cactgttttt    5460
```

```
tcctatacat atatacctat gataaagttc tatttataaa tcagggacag caagagataa    5520
acaataactg caaatagaac aattataaca gtgcactgta ataaaagtga tgtaaatgtg    5580
atatgtctgt ctcttctct caaaatatct tattgtactg tactcacctg taatcagact    5640
gtggttgacc gtgagtaacc gaaaccacag aaagcaaaat cgtggataag gggagactac    5700
tctatatgaa acttaagtta caaaattctc tgaagcattt gaaactagac gttttggaat    5760
tataaaatag tccctttaaa atatccacta gtagaaaaaa acttcatttg cagagaaaag    5820
attgcaataa aactcattcc taaacttttc aattttataa aattaaacat tcttttttta    5880
tccgtattaa caatttctag ttacatagtt tctagttaca tattaccata tattactctt    5940
tatctacaaa taaatagctg atactcaaac tgatcatatt ttgattgtta aacacttgga    6000
tctctcaata cttctgtaag ttaaagtgaa cttaaacagt ttcttgaaaa actccagtag    6060
gtggcagaat acctattgaa tattcgttgc tatactttgc tgtttgtcat taaaacatct    6120
ctacccatat tcttgcaaaa taatatttat attttaatgg ataggaaaat gatttgcaat    6180
tagatgtttc cattcttgaa agaaaaaagc tgcaaataac attttcaaga atataaaaaa    6240
atgagtaaac aaagggaagg ttgtttggtc atttatagac aattaagcac agactgtaga    6300
tgtccttcca attcttggga ggctaaactg agtctaccat ttcttacatt tcttttacct    6360
atttttttgag aattgccagt tgtacagtgt ttagcatgtg gaatgtacca aatatatcta    6420
tgttgtgact taagatattc taaatgtgga taacttctga cctaggaaac atgaagtttg    6480
tagtgaagta agtgaaaaga atgttcagga aatttttttt ctccatctct tcagttggca    6540
tttattgaga gttttatttg aatgcttatt aaaagtatat gatttataat atttagaaaa    6600
tagaagaaaa aagaaaactg tagatgtttt atcttgtttt aatactgtat gtttagtacg    6660
tatacattta tgttcagtg tatcaaaatt tttcattttc attaaagtga atccaatttt    6720
ccatattcta ggtccatttt aaaccatgaa aactttaatc acatattttg taaagggctg    6780
aaagtatgat ttaaactaca gattgatata ttttaattct aaatgaaagg taatgtaaat    6840
aagcatggat ctgattgaat aaagatttta aaatagtaaa aaaaaaaaaa aaaaa         6895
```

<210> SEQ ID NO 28
<211> LENGTH: 5916
<212> TYPE: DNA
<213> ORGANISM: Homo sapiens

<400> SEQUENCE: 28

```
gcccctccct ccgcccgccc gccggcccgc ccgtcagtct ggcaggcagg caggcaatcg      60
gtccgagtgg ctgtcggctc ttcagctctc ccgctcggcg tcttccttcc tcctcccggt     120
cagcgtcggc ggctgcaccg gcggcggcgc agtccctgcg ggaggggcga caagagctga     180
gcggcggccg ccgagcgtcg agctcagcgc ggcggaggcg gcggcggccc ggcagccaac     240
atggcggcgg cggcggcggc gggcgcgggc ccggagatgg tccgcgggca ggtgttcgac     300
gtggggccgc gctacaccaa cctctcgtac atcggcgagg gcgcctacgg catggtgtgc     360
tctgcttatg ataatgtcaa caaagttcga gtagctatca agaaaatcag ccccttgag     420
caccagacct actgccagag aaccctgagg gagataaaaa tcttactgcg cttcagacat     480
gagaacatca ttggaatcaa tgacattatt cgagcaccaa ccatcgagca atgaaagat     540
gtatatatag tacaggacct catggaaaca gatctttaca agctcttgaa gacacaacac     600
ctcagcaatg accatatctg ctattttctc taccagatcc tcagagggtt aaaatatatc     660
cattcagcta acgttctgca ccgtgacctc aagccttcca acctgctgct caacaccacc    720
```

```
tgtgatctca agatctgtga ctttggcctg gcccgtgttg cagatccaga ccatgatcac    780
acagggttcc tgacagaata tgtggccaca cgttggtaca gggctccaga aattatgttg    840
aattccaagg gctacaccaa gtccattgat atttggtctg taggctgcat tctggcagaa    900
atgctttcta acaggcccat ctttccaggg aagcattatc ttgaccagct gaaccacatt    960
ttgggtattc ttggatcccc atcacaagaa gacctgaatt gtataataaa tttaaaagct   1020
aggaactatt tgctttctct tccacacaaa aataaggtgc catggaacag ctgttccca    1080
aatgctgact ccaaagctct ggacttattg gacaaaatgt tgacattcaa cccacacaag   1140
aggattgaag tagaacaggc tctggcccac ccatatctgg agcagtatta cgacccgagt   1200
gacgagccca tcgccgaagc accattcaag ttcgacatgg aattggatga cttgcctaag   1260
gaaaagctca agaactaatt ttttgaagag actgctagat tccagccagg atacagatct   1320
taaatttgtc aggacaaggg ctcagaggac tggacgtgct cagacatcgg tgttcttctt   1380
cccagttctt gaccctggt cctgtctcca gcccgtcttg gcttatccac tttgactcct    1440
ttgagccgtt tggaggggcg gtttctggta gttgtggctt ttatgctttc aaagaatttc   1500
ttcagtccag agaattcctc ctggcagccc tgtgtgtgtc acccattggt gacctgcggc   1560
agtatgtact tcagtgcacc tactgcttac tgttgcttta gtcactaatt gctttctggt   1620
ttgaaagatg cagtggttcc tccctctcct gaatccttt ctacatgatg ccctgctgac    1680
catgcagccg caccagagag agattcttcc ccaattggct ctagtcactg gcatctcact   1740
ttatgatagg gaaggctact acctagggca cttttaagtca gtgacagccc cttatttgca   1800
cttcaccttt tgaccataac tgtttcccca gagcaggagc ttgtggaaat accttggctg   1860
atgttgcagc ctgcagcaag tgcttccgtc tccggaatcc ttggggagca cttgtccacg   1920
tcttttctca tatcatggta gtcactaaca tatataaggt atgtgctatt ggcccagctt   1980
ttagaaaatg cagtcatttt tctaaataaa aaggaagtac tgcacccagc agtgtcactc   2040
tgtagttact gtggtcactt gtaccatata gaggtgtaac acttgtcaag aagcgttatg   2100
tgcagtactt aatgtttgta agacttacaa aaaaagattt aaagtggcag cttcactcga   2160
catttggtga gagaagtaca aaggttgcag tgctgagctg tgggcggttt ctggggatgt   2220
cccagggtgg aactccacat gctggtgcat atacgccctt gagctacttc aaatgtgggt   2280
gtttcagtaa ccacgttcca tgcctgagga tttagcagag aggaacactg cgtctttaaa   2340
tgagaaagta tacaattctt tttccttcta cagcatgtca gcatctcaag ttcatttttc   2400
aacctacagt ataacaattt gtaataaagc ctccaggagc tcatgacgtg aagcactgtt   2460
ctgtcctcaa gtactcaaat atttctgata ctgctgagtc agactgtcag aaaaagctag   2520
cactaactcg tgtttggagc tctatccata ttttactgat ctctttaagt atttgttcct   2580
gccactgtgt actgtggagt tgactcggtg ttctgtccca gtgcggtgcc tcctcttgac   2640
ttccccactg ctctctgtgg tgagaaattt gccttgttca ataattactg taccctcgca   2700
tgactgttac agctttctgt gcagagatga ctgtccaagt gccacatgcc tacgattgaa   2760
atgaaaactc tattgttacc tctgagttgt gttccacgga aaatgctatc cagcagatca   2820
tttaggaaaa ataattctat ttttagcttt tcatttctca gctgtccttt ttcttgttt    2880
gattttgac agcaatggag aatgggttat ataagactg cctgctaata tgaacagaaa    2940
tgcatttgta attcatgaaa ataaatgtac atcttctatc ttcacattca tgttaagatt   3000
cagtgttgct ttcctctgga tcagcgtgtc tgaatggaca gtcaggttca ggttgtgctg   3060
```

```
aacacagaaa tgctcacagg cctcactttg ccgcccaggc actggcccag cacttggatt    3120
tacataagat gagttagaaa ggtacttctg tagggtcctt tttacctctg ctcggcagag    3180
aatcgatgct gtcatgttcc tttattcaca atcttaggtc tcaaatattc tgtcaaaccc    3240
taacaaagaa gccccgacat ctcaggttgg attccctggt tctctctaaa gagggcctgc    3300
ccttgtgccc cagaggtgct gctgggcaca gccaagagtt gggaagggcc gccccacagt    3360
acgcagtcct caccacccag cccagggtgc tcacgctcac cactcctgtg gctgaggaag    3420
gatagctggc tcatcctcgg aaaacagacc cacatctcta ttcttgccct gaaatacgcg    3480
cttttcactt gcgtgctcag agctgccgtc tgaaggtcca cacagcattg acggacaca    3540 gaaatgtgac tgttaccgga taacactgat tagtcagttt tcatttataa aaaagcattg    3600
acagttttat tactcttgtt tcttttttaaa tggaaagtta ctattataag gttaatttgg    3660
agtcctcttc taaatagaaa accatatcct tggctactaa catctggaga ctgtgagctc    3720
cttcccattc cccttcctgg tactgtggag tcagattggc atgaaaccac taacttcatt    3780
ctagaatcat tgtagccata agttgtgtgc ttttttattaa tcatgccaaa cataatgtaa    3840
ctgggcagag aatggtccta accaaggtac ctatgaaaag cgctagctat catgtgtagt    3900
agatgcatca ttttggctct tcttacattt gtaaaaatgt acagattagg tcatcttaat    3960
tcatattagt gacacggaac agcacctcca ctatttgtat gttcaaataa gctttcagac    4020
taatagcttt tttggtgtct aaaatgtaag caaaaaattc ctgctgaaac attccagtcc    4080
tttcatttag tataaaagaa atactgaaca agccagtggg atggaattga aagaactaat    4140
catgaggact ctgtcctgac acaggtcctc aaagctagca gagatacgca gacattgtgg    4200
catctgggta gaagaatact gtattgtgtg tgcagtgcac agtgtgtggt gtgtgcacac    4260
tcattccttc tgctcttggg cacaggcagt gggtgtagag gtaaccagta gctttgagaa    4320
gctacatgta gctcaccagt ggttttctct aaggaatcac aaaagtaaac tacccaacca    4380
catgccacgt aatatttcag ccattcagag gaaactgttt tctctttatt tgcttatatg    4440
ttaatatggt ttttaaattg gtaacttttta tatagtatgg taacagtatg ttaatacaca    4500
catacatacg cacacatgct ttgggtcctt ccataatact tttatatttg taaatcaatg    4560
ttttggagca atcccaagtt taagggaaat attttttgtaa atgtaatggt tttgaaaatc    4620
tgagcaatcc ttttgcttat acatttttaa agcatttgtg ctttaaaatt gttatgctgg    4680
tgtttgaaac atgatactcc tgtggtgcag atgagaagct ataacagtga atatgtggtt    4740
tctcttacgt catccacctt gacatgatgg gtcagaaaca aatggaaatc cagagcaagt    4800
cctccagggt tgcaccaggt ttacctaaag cttgttgcct tttcttgtgc tgtttatgcg    4860
tgtagagcac tcaagaaagt tctgaaactg ctttgtatct gctttgtact gttggtgcct    4920
tcttggtatt gtaccccaaa attctgcata gattatttag tataatggta agttaaaaaa    4980
tgttaaagga agattttatt aagaatctga atgtttattc attatattgt tacaatttaa    5040
cattaacatt tatttgtggt atttgtgatt tggttaatct gtataaaaat tgtaagtaga    5100
aaggtttata tttcatctta attcttttga tgttgtaaac gtacttttta aaagatggat    5160
tatttgaatg tttatggcac ctgacttgta aaaaaaaaaa actacaaaaa aatccttaga    5220
atcattaaat tgtgtccctg tattaccaaa ataacacagc accgtgcatg tatagtttaa    5280
ttgcagtttc atctgtgaaa acgtgaaatt gtctagtcct tcgttatgtt ccccagatgt    5340
cttccagatt tgctctgcat gtggtaactt gtgttagggc tgtgagctgt tcctcgagtt    5400
gaatggggat gtcagtgctc ctagggttct ccaggtggtt cttcagacct tcacctgtgg    5460
```

```
ggggggggggt aggcggtgcc cacgcccatc tcctcatcct cctgaacttc tgcaaccccca    5520 ctgctgggca gacatcctgg gcaaccccctt ttttcagagc aagaagtcat aaagatagga    5580
tttcttggac atttggttct tatcaatatt gggcattatg taatgactta tttacaaaac    5640
aaagatactg gaaaatgttt tggatgtggt gttatggaaa gagcacaggc cttggaccca    5700
tccagctggg ttcagaacta ccccctgctt ataactgcgg ctggctgtgg gccagtcatt    5760
ctgcgtctct gctttcttcc tctgcttcag actgtcagct gtaaagtgga agcaatatta    5820
cttgccttgt atatggtaaa gattataaaa atacatttca actgttcagc atagtacttc    5880
aaagcaagta ctcagtaaat agcaagtctt tttaaa                                5916

<210> SEQ ID NO 29
<211> LENGTH: 5572
<212> TYPE: DNA
<213> ORGANISM: Homo sapiens

<400> SEQUENCE: 29
cctcccctcg cccggcgcgg tcccgtccgc ctctcgctcg cctcccgcct cccctcggtc      60
ttccgaggcg cccgggctcc cggcgcggcg gcggaggggg cggcaggcc ggcgggcggt     120 gatgtggcgg gactctttat gcgctgcggc aggatacgcg ctcggcgctg ggacgcgact     180
gcgctcagtt ctctcctctc ggaagctgca gccatgatgg aagtttgaga gttgagccgc     240
tgtgaggcga ggccgggctc aggcgaggga gatgagagac ggcggcggcc gcggcccgga     300
gcccctctca gcgcctgtga gcagccgcg gggcagcgcc ctcggggagc cggccggcct     360
gcggcggcgg cagcggcggc gtttctcgcc tcctcttcgt cttttctaac cgtgcagcct     420
cttcctcggc ttctcctgaa agggaaggtg gaagccgtgg gctcgggcgg gagccggctg     480
aggcgcggcg gcggcggcgg cacctcccgc tcctggagcg gggggagaa gcggcggcgg     540 cggcggccgc ggcggctgca gctccaggga gggggtctga gtcgcctgtc accatttcca     600
gggctgggaa cgccggagag ttggtctctc cccttctact gcctccaaca cggcggcggc     660
ggcggcggca catccaggga cccgggccgg ttttaaaccct cccgtccgcc gccgccgcac     720
cccccgtggc ccgggctccg gaggccgccg gcggaggcag ccgttcggag gattattcgt     780
cttctcccca ttccgctgcc gccgctgcca ggcctctggc tgctgaggag aagcaggccc     840
agtcgctgca accatccagc agccgccgca gcagccatta cccggctgcg gtccagagcc     900
aagcggcggc agagcgaggg gcatcagcta ccgccaagtc cagagccatt tccatcctgc     960
agaagaagcc ccgccaccag cagcttctgc catctctctc ctccttttc ttcagccaca    1020 ggctcccaga catgacagcc atcatcaaag agatcgttag cagaaacaaa aggagatatc    1080
aagaggatgg attcgactta gacttgacct atatttatcc aaacattatt gctatgggat    1140
ttcctgcaga aagacttgaa ggcgtataca ggaacaatat tgatgatgta gtaaggtttt    1200
tggattcaaa gcataaaaac cattacaaga tatacaatct ttgtgctgaa agacattatg    1260
acaccgccaa atttaattgc agagttgcac aatatccttt tgaagaccat aacccaccac    1320
agctagaact tatcaaaccc ttttgtgaag atcttgacca atggctaagt gaagatgaca    1380
atcatgttgc agcaattcac tgtaaagctg gaaagggacg aactggtgta atgatatgtg    1440
catatttatt acatcggggc aaattttaa aggcacaaga ggccctagat ttctatgggg    1500
aagtaaggac cagagacaaa aagggagtaa ctattcccag tcagaggcgc tatgtgtatt    1560
attatagcta cctgttaaag aatcatctgg attatagacc agtggcactg ttgtttcaca    1620
```

```
agatgatgtt tgaaactatt ccaatgttca gtggcggaac ttgcaatcct cagtttgtgg    1680
tctgccagct aaaggtgaag atatattcct ccaattcagg acccacacga cgggaagaca    1740
agttcatgta ctttgagttc cctcagccgt tacctgtgtg tggtgatatc aaagtagagt    1800
tcttccacaa acagaacaag atgctaaaaa aggacaaaat gtttcacttt tgggtaaata    1860
cattcttcat accaggacca gaggaaacct cagaaaaagt agaaaatgga agtctatgtg    1920
atcaagaaat cgatagcatt tgcagtatag agcgtgcaga taatgacaag gaatatctag    1980
tacttacttt aacaaaaaat gatcttgaca aagcaaataa agacaaagcc aaccgatact    2040
tttctccaaa ttttaaggtg aagctgtact tcacaaaaac agtagaggag ccgtcaaatc    2100
cagaggctag cagttcaact tctgtaacac cagatgttag tgacaatgaa cctgatcatt    2160
atagatattc tgacaccact gactctgatc cagagaatga accttttgat gaagatcagc    2220
atacacaaat tacaaaagtc tgaattttt tttatcaaga gggataaaac accatgaaaa    2280
taaacttgaa taaactgaaa atggacccttt ttttttttaa tggcaatagg acattgtgtc    2340
agattaccag ttataggaac aattctcttt tcctgaccaa tcttgtttta ccctatacat    2400
ccacagggtt ttgacacttg ttgtccagtt gaaaaaggt tgtgtagctg tgtcatgtat     2460
ataccttttt gtgtcaaaag gacatttaaa attcaattag gattaataaa gatggcactt    2520
tcccgtttta ttccagtttt ataaaaagtg gagacagact gatgtgtata cgtaggaatt    2580
ttttcctttt gtgttctgtc accaactgaa gtggctaaag agcttgtgca tatactggtt    2640
cacatcctac ccctttgcac ttgtggcaac agataagttt gcagttggct aagagaggtt    2700
tccgaagggt tttgctacat tctaatgcat gtattcgggt tagggaatg gagggaatgc     2760
tcagaaagga ataatttta tgctggactc tggaccatat accatctcca gctatttaca     2820
cacacctttc tttagcatgc tacagttatt aatctggaca ttcgaggaat tggccgctgt    2880
cactgcttgt tgtttgcgca ttttttttta aagcatattg gtgctagaaa aggcagctaa    2940
aggaagtgaa tctgtattgg ggtacaggaa tgaaccttct gcaacatctt aagatccaca    3000
aatgaaggga tataaaaata atgtcatagg taagaaacac agcaacaatg acttaaccat    3060
ataaatgtgg aggctatcaa caaagaatgg gcttgaaaca ttataaaaat tgacaatgat    3120
ttattaaata tgttttctca attgtaacga cttctccatc tcctgtgtaa tcaaggccag    3180
tgctaaaatt cagatgctgt tagtacctac atcagtcaac aacttacact tattttacta    3240
gttttcaatc ataatacctg ctgtggatgc ttcatgtgct gcctgcaagc ttcttttttc    3300
tcattaaata taaatatttt tgtaatgctg cacagaaatt ttcaatttga gattctacag    3360
taagcgtttt ttttctttga agatttatga tgcacttatt caatagctgt cagccgttcc    3420
acccttttga ccttacacat tctattacaa tgaattttgc agttttgcac attttttaaa    3480
tgtcattaac tgttagggaa ttttacttga atactgaata catataatgt ttatattaaa    3540
aaggacattt gtgttaaaaa ggaaattaga gttgcagtaa actttcaatg ctgcacacaa    3600
aaaaaagaca tttgattttt cagtagaaat tgtcctacat gtgctttatt gatttgctat    3660
tgaaagaata gggttttttt tttttttttt tttttttttt ttaaatgtgc agtgttgaat    3720
catttcttca tagtgctccc ccgagttggg actagggctt caatttcact tcttaaaaaa    3780
aatcatcata tatttgatat gcccagactg catacgattt taagcggagt acaactacta    3840
ttgtaaagct aatgtgaaga tattattaaa aaggtttttt ttccagaaaa tttggtgtct    3900
tcaaattata ccttcacctt gacatttgaa tatccagcca ttttgtttct taatggtata    3960
aaattccatt ttcaataact tattggtgct gaaattgttc actagctgtg gtctgaccta    4020
```

```
gttaatttac aaatacagat tgaataggac ctactagagc agcatttata gagtttgatg    4080
gcaaatagat taggcagaac ttcatctaaa atattcttag taaataatgt tgacacgttt    4140
tccatacctt gtcagtttca ttcaacaatt tttaaatttt taacaaagct cttaggattt    4200
acacatttat atttaaacat tgatatatag agtattgatt gattgctcat aagttaaatt    4260
ggtaaagtta gagacaacta ttctaacacc tcaccattga aatttatatg ccaccttgtc    4320
tttcataaaa gctgaaaatt gttacctaaa atgaaaatca acttcatgtt ttgaagatag    4380
ttataaatat tgttctttgt tacaatttcg ggcaccgcat attaaaacgt aactttattg    4440
ttccaatatg taacatggag ggccaggtca taaataatga cattataatg ggcttttgca    4500
ctgttattat ttttcctttg gaatgtgaag gtctgaatga gggttttgat tttgaatgtt    4560
tcaatgtttt tgagaagcct tgcttacatt ttatggtgta gtcattggaa atggaaaaat    4620
ggcattatat atattatata tataaatata tattatacat actctcctta ctttatttca    4680
gttaccatcc ccatagaatt tgacaagaat tgctatgact gaaaggtttt cgagtcctaa    4740
ttaaaacttt atttatggca gtattcataa ttagcctgaa atgcattctg taggtaatct    4800
ctgagtttct ggaatatttt cttagacttt ttggatgtgc agcagcttac atgtctgaag    4860
ttacttgaag gcatcacttt taagaaagct tacagttggg ccctgtacca tcccaagtcc    4920
tttgtagctc ctcttgaaca tgtttgccat acttttaaaa gggtagttga ataaatagca    4980
tcaccattct ttgctgtggc acaggttata aacttaagtg gagtttaccg gcagcatcaa    5040
atgtttcagc tttaaaaaat aaagtaggg tacaagttta atgtttagtt ctagaaattt     5100
tgtgcaatat gttcataacg atggctgtgg ttgccacaaa gtgcctcgtt tacctttaaa    5160
tactgttaat gtgtcatgca tgcagatgga aggggtggaa ctgtgcacta aagtgggggc    5220
tttaactgta gtatttggca gagttgcctt ctacctgcca gttcaaaagt tcaacctgtt    5280
ttcatataga atatatatac taaaaaattt cagtctgtta aacagcctta ctctgattca    5340
gcctcttcag atactcttgt gctgtgcagc agtggctctg tgtgtaaatg ctatgcactg    5400
aggatacaca aaaataccaa tatgatgtgt acaggataat gcctcatccc aatcagatgt    5460
ccatttgtta ttgtgtttgt taacaaccct ttatctctta gtgttataaa ctccacttaa    5520
aactgattaa agtctcattc ttgtcaaaaa aaaaaaaaaa aaaaaaaaaa aa            5572
```

<210> SEQ ID NO 30  
<211> LENGTH: 7996  
<212> TYPE: DNA  
<213> ORGANISM: Homo sapiens

<400> SEQUENCE: 30

```
atatcccagt ggcccccgtg cggcgacttt agctgctgct gtctcagccg ctccacagcg      60
acggcggcgg ctgcggctta gtcggtggcg gccggcggcg gctgcgggct gagcggcgag     120
tttccgattt aaagctgagc tgcgaggaaa atggcggcgg gaggatcaaa atacttgctg     180
gatggtggac tcagagacca ataaaaataa actgcttgaa catcctttga ctggttagcc     240
agttgctgat gtatattcaa gatgagtgga ttaggagaaa acttggatcc actggccagt     300
gattcacgaa aacgcaaatt gccatgtgat actccaggac aaggtcttac ctgcagtggt     360
gaaaaacgga gacgggagca ggaaagtaaa tatattgaag aattggctga gctgatatct     420
gccaatctta gtgatattga caatttcaat gtcaaaccag ataaatgtgc gatttaaag     480 gaaacagtaa gacagatacg tcaaataaaa gagcaaggaa aaactatttc caatgatgat     540
```

```
gatgttcaaa aagccgatgt atcttctaca gggcagggag ttattgataa agactcctta    600
ggaccgcttt tacttcaggc attggatggt ttcctatttg tggtgaatcg agacggaaac    660
attgtatttg tatcagaaaa tgtcacacaa tacctgcaat ataagcaaga ggacctggtt    720
aacacaagtg tttacaatat cttacatgaa gaagacagaa aggatttttct taagaattta    780
ccaaaatcta cagttaatgg agtttcctgg acaaatgaga cccaaagaca aaaaagccat    840
acatttaatt gccgtatgtt gatgaaaaca ccacatgata ttctggaaga cataaacgcc    900
agtcctgaaa tgcgccagag atatgaaaca atgcagtgct ttgccctgtc tcagccacga    960
gctatgatgg aggaagggga agatttgcaa tcttgtatga tctgtgtggc acgccgcatt   1020
actacaggag aaagaacatt tccatcaaac cctgagagct ttattaccag acatgatctt   1080
tcaggaaagg ttgtcaatat agatacaaat tcactgagat cctccatgag gcctggcttt   1140
gaagatataa tccgaaggtg tattcagaga ttttttagtc taaatgatgg gcagtcatgg   1200
tcccagaaac gtcactatca agaagcttat cttaatggcc atgcagaaac cccagtatat   1260
cgattctcgt tggctgatgg aactatagtg actgcacaga caaaaagcaa actcttccga   1320
aatcctgtaa caaatgatcg acatggcttt gtctcaaccc acttccttca gagagaacag   1380
aatggatata gaccaaaccc aaatcctgtt ggacaaggga ttagaccacc tatggctgga   1440
tgcaacagtt cggtaggcgg catgagtatg tcgccaaacc aaggcttaca gatgccgagc   1500
agcagggcct atggcttggc agaccctagc accacagggc agatgagtgg agctaggtat   1560
gggggttcca gtaacatagc ttcattgacc cctgggccag gcatgcaatc accatcttcc   1620
taccagaaca caactatgg gctcaacatg agtagccccc cacatgggag tcctggtctt   1680
gccccaaacc agcagaatat catgatttct cctcgtaatc gtgggagtcc aaagatagcc   1740
tcacatcagt tttctcctgt tgcaggtgtg cactctccca tggcatcttc tggcaatact   1800
gggaaccaca gcttttccag cagctctctc agtgccctgc aagccatcag tgaaggtgtg   1860
gggacttccc ttttatctac tctgtcatca ccaggcccca aattggataa ctctcccaat   1920
atgaatatta cccaaccaag taaagtaagc aatcaggatt ccaagagtcc tctgggcttt   1980
tattgcgacc aaaatccagt ggagagttca atgtgtcagt caaatagcag agatcacctc   2040
agtgacaaag aaagtaagga gagcagtgtt gaggggcag agaatcaaag gggtcctttg    2100
gaaagcaaag gtcataaaaa attactgcag ttacttacct gttcttctga tgaccggggt   2160
cattcctcct tgaccaactc cccctagat tcaagttgta aagaatcttc tgttagtgtc    2220
accagcccct ctggagtctc ctcctctaca tctggaggag tatcctctac atccaatatg   2280
catgggtcac tgttacaaga gaagcaccgg attttgcaca agttgctgca gaatgggaat   2340
tcaccagctg aggtagccaa gattactgca gaagccactg ggaaagacac cagcagtata   2400
acttcttgtg gggacggaaa tgttgtcaag caggagcagc taagtcctaa gaagaaggag   2460
aataatgcac ttcttagata cctgctggac agggatgatc ctagtgatgc actctctaaa   2520
gaactacagc cccaagtgga aggagtggat aataaaatga gtcagtgcac cagctccacc   2580
attcctagct caagtcaaga gaaagaccct aaaattaaga cagagacaag tgaagaggga   2640
tctggagact tggataatct agatgctatt cttggtgatc tgactagttc tgacttttac   2700
aataattcca tatcctcaaa tggtagtcat ctggggacta agcaacaggt gtttcaagga   2760
actaattctc tgggtttgaa aagttccacag tctgtgcagt ctattcgtcc tccatataac   2820
cgagcagtgt ctctgatag ccctgttttct gttggctcaa gtcctccagt aaaaaatatc    2880
agtgcttttcc ccatgttacc aaagcaaccc atgttgggtg ggaatccaag aatgatggat   2940
```

```
agtcaggaaa attatggctc aagtatgggt gggccaaacc gaaatgtgac tgtgactcag    3000
actccttcct caggagactg gggcttacca aactcaaagg ccggcagaat ggaacctatg    3060
aattcaaact ccatgggaag accaggagga gattataata cttctttacc cagacctgca    3120
ctgggtggct ctattcccac attgcctctt cggtctaata gcataccagg tgcgagacca    3180
gtattgcaac agcagcagca gatgcttcaa atgaggcctg gtgaaatccc catgggaatg    3240
ggggctaatc cctatggcca agcagcagca tctaaccaac tgggttcctg cccgatggc     3300
atgttgtcca tggaacaagt ttctcatggc actcaaaata ggcctcttct taggaattcc    3360
ctggatgatc ttgttgggcc accttccaac ctggaaggcc agagtgacga aagagcatta    3420
ttggaccagc tgcacactct tctcagcaac acagatgcca caggcctgga agaaattgac    3480
agagcttttgg gcattcctga acttgtcaat cagggacagg cattagagcc caaacaggat    3540
gctttccaag gccaagaagc agcagtaatg atggatcaga aggcaggatt atatggacag    3600
acataccccag cacaggggcc tccaatgcaa ggaggctttc atcttcaggg acaatcacca    3660
tcttttaact ctatgatgaa tcagatgaac cagcaaggca atttttcctct ccaaggaatg    3720
cacccacgag ccaacatcat gagaccccgg acaaacaccc caagcaact tagaatgcag     3780
cttcagcaga ggctgcaggg ccagcagttt ttgaatcaga gccgacaggc acttgaattg    3840
aaaatggaaa accctactgc tggtggtgct gcggtgatga ggcctatgat gcagccccag    3900
gtgagctccc agcagggttt tcttaatgct caaatggtcg cccaacgcag cagagagctg    3960
ctaagtcatc acttccgaca acagagggtg gctatgatga tgcagcagca gcagcagcag    4020
caacagcagc agcagcagca gcagcagcag caacagcaac agcaacagca acagcagcaa    4080
cagcagcaaa cccaggcctt cagcccacct cctaatgtga ctgcttcccc cagcatggat    4140
gggcttttgg caggacccac aatgccacaa gctcctccgc aacagtttcc atatcaacca    4200
aattatggaa tgggacaaca accagatcca gcctttggtc gagtgtctag tcctcccaat    4260
gcaatgatgt cgtcaagaat gggtccctcc cagaatccca tgatgcaaca cccgcaggct    4320
gcatccatct atcagtcctc agaaatgaag ggctggccat caggaaattt ggccaggaac    4380
agctcctttt cccagcagca gtttgcccac caggggaatc ctgcagtgta tagtatggtg    4440
cacatgaatg gcagcagtgg tcacatggga cagatgaaca tgaaccccat gccatgtctt    4500
ggcatgccta tgggtcctga tcagaaatac tgctgacatc tctgcaccag gacctcttaa    4560
ggaaaccact gtacaaatga cactgcacta ggattattgg gaaggaatca ttgttccagg    4620
catccatctt ggaagaaagg accagctttg agctccatca agggtatttt aagtgatgtc    4680
atttgagcag gactggattt taagccgaag ggcaatatct acgtgttttt ccccctcct     4740
tctgctgtgt atcatggtgt tcaaaacaga aatgtttttt ggcattccac ctcctaggga    4800
tataattctg gagacatgga gtgttactga tcataaaact tttgtgtcac tttttctgc     4860
cttgctagcc aaaatctctt aaatacacgt aggtgggcca gaacattg gaagaatcaa      4920
gagagattag aatatctggt ttctctagtt gcagtattgg acaaagagca tagtcccagc    4980
cttcaggtgt agtagttctg tgttgaccct ttgtccagtg gaattggtga ttctgaattg    5040
tcctttacta atggtgttga gttgctctgt ccctattatt tgccctaggc tttctcctaa    5100
tgaaggtttt catttgccat tcatgtcctg taatacttca cctccaggaa ctgtcatgga    5160
tgtccaaatg gctttgcaga aaggaaatga gatgacagta tttaatcgca gcagtagcaa    5220
acttttcaca tgctaatgtg cagctgagtg cactttattt aaaaagaatg gataaatgca    5280
```

```
atattcttga ggtcttgagg gaatagtgaa acacattcct ggttttgcc tacacttacg    5340 tgttagacaa gaactatgat tttttttttt aaagtactgg tgtcaccctt tgcctatatg    5400
gtagagcaat aatgcttttt aaaaataaac ttctgaaaac ccaaggccag gtactgcatt    5460
ctgaatcaga atctcgcagt gtttctgtga atagattttt ttgtaaatat gacctttaag    5520
atattgtatt atgtaaaata tgtatatacc ttttttttgta ggtcacaaca actcattttt    5580
acagagtttg tgaagctaaa tatttaacat tgttgatttc agtaagctgt gtggtgaggc    5640
taccagtgga agagacatcc cttgactttt gtggcctggg ggaggggtag tgctccacag    5700
cttttccttc cccaccccc agccttagat gcctcgctct tttcaatctc ttaatctaaa     5760
tgctttttaa agagattatt tgtttagatg taggcatttt aatttttttaa aaattcctct    5820 accagaacta agcactttgt taatttgggg ggaaagaata gatatgggga aataaactta    5880
aaaaaaaatc aggaatttaa aaaaacgagc aatttgaaga gaatcttttg gattttaagc    5940
agtccgaaat aatagcaatt catgggctgt gtgtgtgtgt gtatgtgtgt gtgtgtgtgt    6000
gtatgtttaa ttatgttacc ttttcatccc ctttaggagc gttttcagat tttgttgct     6060 aagacctgaa tcccatattg agatctcgag tagaatcctt ggtgtggttt ctggtgtctg    6120
ctcagctgtc ccctcattct actaatgtga tgctttcatt atgtccctgt ggattagaat    6180
agtgtcagtt atttcttaag taactcagta cccagaacag ccagttttac tgtgattcag    6240
agccacagtc taactgagca cctttttaaac ccctccctct tctgcccct accacttttc     6300 tgctgttgcc tctctttgac acctgttttta gtcagttggg aggaagggaa aaatcaagtt    6360 taattcccctt tatctgggtt aattcatttg gttcaaatag ttgacggaat tgggtttctg    6420
aatgtctgtg aatttcagag gtctctgcta gccttggtat cattttctag caataactga    6480
gagccagtta attttaagaa tttcacacat ttagccaatc tttctagatg tctctgaagg    6540
taagatcatt taatatcttt gatatgctta cgagtaagtg aatcctgatt atttccagac    6600
ccaccaccag agtggatctt attttcaaag cagtatagac aattatgagt ttgccctctt    6660
tcccctacca agttcaaaat atatctaaga aagattgtaa atccgaaaac ttccattgta    6720
gtggcctgtg cttttcagat agtatactct cctgttggga gacagaggaa gaaccaggtc    6780
agtctgtctc ttttcagct caattgtatc tgaccttct ttaagttatg tgtgtggga       6840 gaaatagaat ggtgctctta tctttcttga ctttaaaaaa attattaaaa acaaaaaaaa    6900
aataaatttt tttgcaatcc tttcctcaga cctggctcca ggctaactgg aaggcagcac    6960 tcccttttt atatagtaga aaatgaagt ttattataag ttttttatatt ttctacttgt      7020 tcatttggtg caaactcaag atttctttta ataggtgcag tctttgagat aatttgtttt    7080
tacctgtatt gcccttatc ttttttaggt aattctttgt actcctgctg tctacctctc     7140 ctcacaccc agcaccccc atttttcaa accttggtat ctgttgggtg aacagtataa       7200
tcttttcatc tgcttttaga atgtgggata tttccagtac ctactttttt tttttttttt   7260
tgctgaatcc aaagatatat aaataaaata tatatatttt ataaagatca gaatgatata    7320
aaggagatac atgtttcttc ctttaaaaaa taaacggaag ttacattgtt aatgttcata    7380
ttatgatgcc actttctaa actgcatctg gattgaaagg tgtaaatatc aataacagtg     7440
ctacttagtt atcagtattt aatatctgag gtgagttggg ggtatctata ttaggggtag    7500
ggtattacag aagataattg gcttgatgtc ctagaagttc tttgatccag aggtgggtgc    7560
agctgaaagt aaacagaatg gattgccagt tacatgtatg cctgcccagt tccctttttta  7620 tttgcagaag ctgtgagttt tgttcacaat taggttccta ggagcaaaac ctcaaggatt    7680
```

```
gatttattgt tttcaactcc aaggcacact gttaataaac gagcagggtg ttttctctct    7740
tcctttctaa tatatggagt ttcgaagaat aaaatatgag agcaatattt aaattctcag    7800
gaattgactt atactcttga gaatgaattc agtttcaatc aagtttacat tatgttgctt    7860
aaaaaaatag aaattattct ttatcttgca aagaattgaa accacatgaa atgacttatg    7920
ggggatggtg agctgtgact gctttgctga ccattttgga tgtcattgta aataaaggtt    7980
tctatttaaa attgga                                                    7996

<210> SEQ ID NO 31
<211> LENGTH: 3070
<212> TYPE: DNA
<213> ORGANISM: Homo sapiens

<400> SEQUENCE: 31
ggcgccgtct tgatactttc agaaagaatg cattccctgt aaaaaaaaaa aaaaaatact      60
gagagaggga gagagagaga gaagaagaga gagagacgga gggagagcga gacagagcga     120
gcaacgcaat ctgaccgagc aggtcgtacg ccgccgcctc ctcctcctct ctgctcttcg     180
ctacccaggt gacccgagga gggactccgc ctccgagcgg ctgaggaccc cggtgcagag     240
gagcctggct cgcagaattg cagagtcgtc gccccttttt acaacctggt cccgttttat     300
tctgccgtac ccagtttttg gattttttgtc ttcccttct tctctttgct aaacgacccc     360
tccaagataa ttttttaaaaa accttctcct ttgctcacct ttgcttccca gccttcccat     420 cccccccaccg aaagcaaatc attcaacgac ccccgaccct ccgacggcag gagcccccg     480 acctcccagg cggaccgccc tccctccccg cgcgcgggtt ccgggcccgg cgagagggcg     540
cgagcacagc cgaggccatg gaggtgacgg cggaccagcc gcgctgggtg agccaccacc     600
accccgccgt gctcaacggg cagcacccgg acacgcacca cccgggcctc agccactcct     660
acatggacgc ggcgcagtac ccgctgccgg aggaggtgga tgtgcttttt aacatcgacg     720
gtcaaggcaa ccacgtcccg ccctactacg gaaactcggt cagggccacg gtgcagaggt     780
accctccgac ccaccacggg agccaggtgt gccgcccgcc tctgcttcat ggatccctac     840
cctggctgga cggcggcaaa gccctgggca gccaccacac cgcctccccc tggaatctca     900
gccccttctc caagacgtcc atccaccacg gctcccgggg gcccctctcc gtctacccc      960 cggcctcgtc ctcctccttg tcgggggggcc acgccagccc gcacctcttc accttcccgc    1020
ccaccccgcc gaaggacgtc tccccggacc catcgctgtc caccccaggc tcggccggct    1080
cggcccggca ggacgagaaa gagtgcctca gtaccaggt gccctgccc gacagcatga    1140 agctggagtc gtcccactcc cgtggcagca tgaccgccct gggtggagcc tcctcgtcga    1200
cccaccaccc catcaccacc tacccgccct acgtgcccga gtacagctcc ggactcttcc    1260
cccccagcag cctgctgggc ggctcccccca ccggcttcgg atgcaagtcc aggcccaagg    1320
cccggtccag cacagaaggc agggagtgtg tgaactgtgg ggcaacctcg acccactgt    1380 ggcggcgaga tggcacggga cactacctgt gcaacgcctg cgggctctat acaaaaatga    1440
acggacagaa ccggcccctc attaagccca gcgaaggct gtctgcagcc aggagagcag    1500
ggacgtcctg tgcgaactgt cagaccacca caaccacact ctggaggagg aatgccaatg    1560
gggaccctgt ctgcaatgcc tgtgggctct actacaagct tcacaatatt aacagacccc    1620
tgactatgaa gaaggaaggc atccagacca gaaaccgaaa aatgtctagc aaatccaaaa    1680
agtgcaaaaa agtgcatgac tcactggagg acttcccccaa gaacagctcg tttaacccgg    1740
```

```
ccgccctctc cagacacatg tcctccctga gccacatctc gcccttcagc cactccagcc    1800
acatgctgac cacgcccacg ccgatgcacc cgccatccag cctgtccttt ggaccacacc    1860 accccctccag catggtcacc gccatgggtt agagccctgc tcgatgctca cagggccccc    1920
agcgagagtc cctgcagtcc ctttcgactt gcattttgc aggagcagta tcatgaagcc     1980
taaacgcgat ggatatatgt ttttgaaggc agaaagcaaa attatgtttg ccactttgca    2040
aaggagctca ctgtggtgtc tgtgttccaa ccactgaatc tggacccat ctgtgaataa     2100 gccattctga ctcatatccc ctatttaaca gggtctctag tgctgtgaaa aaaaaatgc    2160 tgaacattgc ataaactta tattgtaaga aatactgtac aatgacttta ttgcatctgg    2220
gtagctgtaa ggcatgaagg atgccaagaa gtttaaggaa tatgggagaa atagtgtgga    2280
aattaagaag aaactaggtc tgatattcaa atggacaaac tgccagtttt gtttcctttc    2340
actggccaca gttgtttgat gcattaaaag aaaataaaaa aagaaaaaa gagaaaagaa    2400 aaaaaagaa aaaagttgta ggcgaatcat ttgttcaaag ctgttggcct ctgcaaagga     2460
aataccagtt ctgggcaatc agtgttaccg ttcaccagtt gccgttgagg gtttcagaga    2520 gccttttct aggcctacat gctttgtgaa caagtccctg taattgttgt ttgtatgtat     2580
aattcaaagc accaaaataa gaaaagatgt agatttattt catcatatta tacagaccga    2640
actgttgtat aaatttattt actgctagtc ttaagaactg cttctttcg tttgtttgtt    2700 tcaatatttt ccttctctct caattttggg ttgaataaac tagattacat tcagttggcc    2760
taaggtggtt gtgctcggag ggtttcttgt ttcttttcca ttttgttttt ggatgatatt    2820
tattaaatag cttctaagag tccggcggca tctgtcttgt ccctattcct gcagcctgtg    2880
ctgagggtag cagtgtatga gctaccagcg tgcatgtcag cgaccctggc ccgacaggcc    2940
acgtcctgca atcggcccgg ctgcctcttc gccctgtcgt gttctgtgtt agtgatcact    3000
gcctttaata cagtctgttg gaataatatt ataagcataa taataaagtg aaatatttt     3060 aaaactacaa                                                            3070
```

<210> SEQ ID NO 32
<211> LENGTH: 3140
<212> TYPE: DNA
<213> ORGANISM: Homo sapiens

<400> SEQUENCE: 32

```
ggcgggcgct cggcgactcg tccccggggc cccgcgcggg cccgggcagc aggggcgtga     60
tgtcacggca gggagggggc gcgggagccg ccgggccggc ggggaggcgg gggaggtgtt    120
ttccagcttt aaaaaggcag gaggcagagc gcggccctgc gtcagagcga gactcagagg    180
ctccgaactc gccggcggag tcgccgcgcc agatcccagc agcagggcgc gggcaccggg    240
gcgcgggcag ggctcggagc caccgcgcag gtcctagggc cgcggccggg ccccgccacg    300
cgcgcacacg cccctcgatg actttcctcc ggggcgcgcg gcgctgagcc cggggcgagg    360
gctgtcttcc cggagacccg accccggcag cgcggggcgg ccgcttctcc tgtgcctccg    420
cccgccgctc cactccccgc cgccgccgcg cggatgccaa gcaccagctt ccagtccct    480 tccaagtttc cacttggccc tgcggctgcg gtcttcggga gaggagaaac tttgggccc    540 gcgccgcgcg ccggcggcac catgaagtca gcggaggaag aacactatgg ctatgcatcc    600
tccaacgtca gcccgccct gcgctcccc acggcgcact ccaccctgcc ggccccgtgc    660
cacaaccttc agacctccac accgggcatc atcccgccgg cggatcaccc ctcggggtac    720
ggagcagctt tggacggtgg gccgcgggc tacttcctct cctccggcca caccaggcct    780
```

```
gatgggcccc ctgccctgga gagtcctcgc atcgagataa cctcgtgctt gggcctgtac    840
cacaacaata accagttttt ccacgatgtg gaggtggaag acgtcctccc tagctccaaa    900
cggtccccct ccacggccac gctgagtctg cccagcctgg aggcctacag agacccctcg    960
tgcctgagcc cggccagcag cctgtcctcc cggagctgca actcagaggc ctcctcctac   1020
gagtccaact actcgtaccc gtacgcgtcc cccagacgt cgccatggca gtctccctgc   1080
gtgtctccca agaccacgga ccccgaggag ggctttcccc gcgggctggg ggcctgcaca   1140
ctgctgggtt ccccgcggca ctcccctcc acctcgcccc gcgccagcgt cactgaggag   1200
agctggctgg gtgcccgctc ctccagaccc gcgtcccctt gcaacaagag gaagtacagc   1260
ctcaacggcc ggcagccgcc ctactcaccc caccactcgc ccacgccgtc cccgcacggc   1320
tccccgcggg tcagcgtgac cgacgactcg tggttgggca acaccaccca gtacaccagc   1380
tcggccatcg tggccgccat caacgcgctg accaccgaca gcagcctgga cctgggagat   1440
ggcgtccctg tcaagtcccg caagaccacc ctggagcagc cgccctcagt ggcgctcaag   1500
gtggagcccg tcggggagga cctgggcagc cccccgcccc cggccgactt cgcgcccgaa   1560
gactactcct ctttccagca catcaggaag gcggcttct gcgaccagta cctggcggtg   1620
ccgcagcacc cctaccagtg ggcgaagccc aagcccctgt ccctacgtc ctacatgagc   1680
ccgaccctgc ccgccctgga ctggcagctg ccgtcccact caggcccgta tgagcttcgg   1740
attgaggtgc agcccaagtc ccaccaccga gcccactacg agacggaggg cagccggggg   1800
gccgtgaagg cgtcggccgg aggacacccc atcgtcagc tgcatggcta cttggagaat   1860
gagccgctga tgctgcagct tttcattggg acggcggacg accgcctgct gcgcccgcac   1920
gccttctacc aggtgcaccg catcacaggg aagaccgtgt ccaccaccag ccacgaggcc   1980
atcctctcca acaccaaagt cctggagatc ccactcctgc cggagaacag catgcgagcc   2040
gtcattgact gtgccggaat cctgaaactc agaaactccg acattgaact tcggaaagga   2100
gagacggaca tcggaggaa gaacacacgg gtacggctgg tgttccgcgt tcacgtcccg   2160
caacccagcg gccgcacgct gtccctgcag gtggcctcca accccatcga atgctcccag   2220
cgctcagctc aggagctgcc tctggtggag aagcagagca cggacagcta ccggtcgtg   2280
ggcgggaaga agatggtcct gtctggccac aacttcctgc aggactccaa ggtcattttc   2340
gtggagaaag ccccagatgg ccaccatgtc tgggagatgg aagcgaaaac tgaccgggac   2400
ctgtgcaagc cgaattctct ggtggttgag atcccgccat ttcggaatca gaggataacc   2460
agccccgttc acgtcagttt ctacgtctgc aacgggaaga gaaagcgaag ccagtaccag   2520
cgtttcacct accttcccgc caacggtaac gccatctttc taaccgtaag ccgtgaacat   2580
gagcgcgtgg ggtgcttttt ctaaagacgc agaaacgacg tcgccgtaaa gcagcgtggc   2640
gtgttgcaca tttaactgtg tgatgtcccg ttagtgagac cgagccatcg atgccctgaa   2700
aaggaaagga aaagggaagc ttcggatgca ttttccttga tccctgttgg gggtgggggg   2760
cggggggttgc atactcagat agtcacggtt attttgcttc ttgcgaatgt ataacagcca   2820
aggggaaaac atggctcttc tgctccaaaa aactgagggg gtcctggtgt gcatttgcac   2880
cctaaagctg cttacggtga aaaggcaaat aggtatagct attttgcagg cacctttagg   2940
aataaacttt gcttttaagc ctgtagtcct gatgtggtct ttaaggatgg tgaatgagct   3000
ttgtgctggg cggacgtccc cgagacactt ctccaggggt aacttcatct cctgggacca   3060
cgggcatcca ggctggggca ccttctcctc aacctgcctg cccctcaccc gccgtgggaa   3120
```
tggctccttt tcactcatac                                              3140

<210> SEQ ID NO 33
<211> LENGTH: 2337
<212> TYPE: DNA
<213> ORGANISM: Homo sapiens

<400> SEQUENCE: 33

| | |
|---|---:|
| gttaggccaa cagggaagcg cggagccgca gatctggtcc gtcgctcgcc tgggtgcctg | 60 |
| gagctgagct gcggcaaggc ccggctcctg ttcgaccgcc cgaggggtgt gcgtgtgcgc | 120 |
| gttgcggagg gtgcgctcag agggccgcgt cgtggctgca gcggctgctg ccgccgcagg | 180 |
| ggatctaata tcacctacct gtccctgtca ctcttgacac ttctctgtca gggctgccgc | 240 |
| gtggggggg ggcgggcaga gcgcggtcgg cgttagcttt ccttattgga ggggttcttg | 300 |
| ggggagggag ggagagaaga aggggtctt tgcccactct tgtttcgctt tggagcttgg | 360 |
| aagcctgctc cctaaagacg ctctgagtgg tgcccttctg cccacatccc atgtcttcgt | 420 |
| ttgcccgctg actttccgtc tccggacttt ttcgcttgag ccttccggag gagacggggg | 480 |
| cagcttggct tgagaactcg gcggggttg cgtccctgg ctctccccgc agcggggaaa | 540 |
| ctccgcgcct agagcgcgac ccggagcggg cagcggcggc tacggggct cggcgggca | 600 |
| gtagccaagg actagtagag cgtcgcgctc cctcgtccat gaactgcatg aaaggcccgc | 660 |
| ttcacttgga gcaccgagca gcggggacca agctgtcggc cgtctcctca tcttcctgtc | 720 |
| accatcccca gccgttagcc atggcttcgg ttctggctcc cggtcagccc cggtcgctgg | 780 |
| actcctccaa gcacaggctg gaggtgcaca ccatctccga cacctccagc ccggaggccg | 840 |
| cagagaaaga taaaagccag caggggaaga atgaggacgt gggcgccgag gacccgtcta | 900 |
| agaagaagcg gcaaagcgg cagcggactc actttaccag ccagcagctc caggagctgg | 960 |
| aggccacttt ccagaggaac cgctacccgg acatgtccac acgcgaagaa atcgctgtgt | 1020 |
| ggaccaacct tacggaagcc cgagtccggg tttggttcaa gaatcgtcgg gccaaatgga | 1080 |
| gaaagaggga gcgcaaccag caggccgagc tatgcaagaa tggcttcggg ccgcagttca | 1140 |
| atgggctcat gcagccctac gacgacatgt acccaggcta ttcctacaac aactgggccg | 1200 |
| ccaagggcct tacatccgcc tccctatcca ccaagagctt cccccttcttc aactctatga | 1260 |
| acgtcaaccc cctgtcatca cagagcatgt tttccccacc caactctatc tcgtccatga | 1320 |
| gcatgtcgtc cagcatggtg ccctcagcag tgacaggcgt cccgggctcc agtctcaaca | 1380 |
| gcctgaataa cttgaacaac ctgagtagcc cgtcgctgaa ttccgcggtg ccgacgcctg | 1440 |
| cctgtccctta cgcgccgccg actcctccgt atgtttatag ggacacgtgt aactcgagcc | 1500 |
| tggccagcct gagactgaaa gcaaagcagc actccagctt cggctacgcc agcgtgcaga | 1560 |
| acccggcctc caacctgagt gcttgccagt atgcagtgga ccggcccgtg tgagccgcac | 1620 |
| ccacagcgcc gggatcctag gaccttgccg gatgggcaa ctccgcccctt gaaagactgg | 1680 |
| gaattatgct agaaggtcgt gggcactaaa gaaagggaga gaaagagaag ctatatagag | 1740 |
| aaaaggaaac cactgaatca agagagagc tcctttgatt tcaaagggat gtcctcagtg | 1800 |
| tctgacatct ttcactacaa gtatttctaa cagttgcaag gacacataca caaacaaatg | 1860 |
| tttgactgga tatgacattt taacattact ataagcttgt tattttttaa gtttagcatt | 1920 |
| gttaacattt aaatgactga aaggatgtat atatatcgaa atgtcaaatt aattttataa | 1980 |
| aagcagttgt tagtaatatc acaacagtgt ttttaaaggt taggctttaa aataaagcat | 2040 |
| gttatacaga agcgattagg attttttcgct tgcgagcaag ggagtgtata tactaaatgc | 2100 |

-continued

| | |
|---|---|
| cacactgtat gtttctaaca tattattatt attataaaaa atgtgtgaat atcagtttta | 2160 |
| gaatagtttc tctggtggat gcaatgatgt ttctgaaact gctatgtaca acctaccctg | 2220 |
| tgtataacat ttcgtacaat attattgttt tacttttcag caaatatgaa acaaatgtgt | 2280 |
| tttatttcat gggagtaaaa tatactgcat acaaaaaaaa aaaaaaaaaa aaaaaaa | 2337 |

<210> SEQ ID NO 34
<211> LENGTH: 6531
<212> TYPE: DNA
<213> ORGANISM: Homo sapiens

<400> SEQUENCE: 34

| | |
|---|---|
| gcccagccag cttgcgtcac cgcttcagag cggagaagag cgagcagggg agagcgagac | 60 |
| cagttttaag gggaggaccg gtgcgagtga ggcagcccg aggctctgct cgcccaccac | 120 |
| ccaatcctcg cctcccttct gctccacctt ctctctctgc cctcacctct cccccgaaaa | 180 |
| cccctattt agccaaagga aggaggtcag gggaacgctc tcccctcccc ttccaaaaaa | 240 |
| caaaaacaga aaaacccttt tccaggccgg ggaaagcagg agggagaggg gccgccgggc | 300 |
| tggccatgga gctgctgtgc cacgaggtgg accggtccg cagggccgtg cgggaccgca | 360 |
| acctgctccg agacgaccgc gtcctgcaga acctgctcac catcgaggag cgctaccttc | 420 |
| cgcagtgctc ctacttcaag tgcgtgcaga aggacatcca accctacatg cgcagaatgg | 480 |
| tggccacctg gatgctggag gtctgtgagg aacagaagtg cgaagaagag gtcttccctc | 540 |
| tggccatgaa ttacctggac cgtttcttgg ctggggtccc gactccgaag tcccatctgc | 600 |
| aactcctggg tgctgtctgc atgttcctgg cctccaaact caaagagacc agcccgctga | 660 |
| ccgcggagaa gctgtgcatt tacaccgaca actccatcaa gcctcaggag ctgctggagt | 720 |
| gggaactggt ggtgctgggg aagttgaagt ggaacctggc agctgtcact cctcatgact | 780 |
| tcattgagca catcttgcgc aagctgcccc agcagcggga gaagctgtct ctgatccgca | 840 |
| agcatgctca gaccttcatt gctctgtgtg ccaccgactt taagtttgcc atgtaccac | 900 |
| cgtcgatgat cgcaactgga agtgtgggag cagccatctg tgggctccag caggatgagg | 960 |
| aagtgagctc gctcacttgt gatgccctga ctgagctgct ggctaagatc accaacacag | 1020 |
| acgtggattg tctcaaagct tgccaggagc agattgaggc ggtgctcctc aatagcctgc | 1080 |
| agcagtaccg tcaggaccaa cgtgacggat ccaagtcgga ggatgaactg gaccaagcca | 1140 |
| gcacccctac agacgtgcgg gatatcgacc tgtgaggatg ccagttgggc cgaaagagag | 1200 |
| agacgcgtcc ataatctggt ctcttcttct ttctggttgt ttttgttctt tgtgttttag | 1260 |
| ggtgaaactt aaaaaaaaaa ttctgccccc acctagatca tatttaaaga tcttttagaa | 1320 |
| gtgagagaaa aaggtcctac gaaaacggaa taataaaaag catttggtgc ctatttgaag | 1380 |
| tacagcataa gggaatccct tgtatatgcg aacagttatt gtttgattat gtaaagtaa | 1440 |
| tagtaaaatg cttacaggaa aacctgcaga gtagttagaa aatatgtatg cctgcaatat | 1500 |
| gggaacaaat tagaggagac tttttttttt catgttatga gctagcacat acacccctt | 1560 |
| gtagtataat ttcaaggaac tgtgtacgcc atttatggca tgattagatt gcaaagcaat | 1620 |
| gaactcaaga aggaattgaa ataaggaggg acatgatggg gaaggagtac aaaacaatct | 1680 |
| ctcaacatga ttgaaccatt tgggatggag aagcacctt gctctcagcc acctgttact | 1740 |
| aagtcaggag tgtagttgga tctctacatt aatgtcctct tgctgtctac agtagctgct | 1800 |
| acctaaaaaa agatgtttta ttttgccagt tggacacagg tgattggctc ctgggtttca | 1860 |

```
tgttctgtga catcctgctt cttcttccaa atgcagttca ttgcagacac caccatattg    1920
ctatctaatg gggaaatgta gctatgggcc ataaccaaaa ctcacatgaa acggaggcag    1980
atggagacca agggtgggat ccagaatgga gtcttttctg ttattgtatt taaaagggta    2040
atgtggcctt ggcatttctt cttagaaaaa aactaatttt tggtgctgat tggcatgtct    2100
ggttcacagt ttagcattgt tataaaccat tccattcgaa aagcactttg aaaaattgtt    2160
cccgagcgat agatgggatg gtttatgcaa gtcatgctga atactcctcc cctcttctct    2220
tttgccccct cccttcctgc ccccagtctg ggttactctt cgcttctggt atctggcgtt    2280
ctttggtaca cagttctggt gttcctacca ggactcaaga dacacccctt cctgctgaca    2340
ttcccatcac aacattcctc agacaagcct gtaaactaaa atctgttacc attctgatgg    2400
cacagaagga tcttaattcc catctctata cttctccttt ggacatggaa agaaaagtta    2460 tgctggtgc aaagatagat ggctgaacat cagggtgtgg cattttgttc ccttttccgt    2520 ttttttttt ttattgttgt tgttaatttt attgcaaagt tgtattcagc gtacttgaat    2580
ttttcttcct ctccacttct tagaggcatt cagttagcaa agaggttgga gcaacaactt    2640 ttttttttt ttttgcacaa ttgtaattga caggtaatga agctatttgt taaaatattt    2700 gccttttaa gtaaaaaaga aaatcagaa cagggctatt tgaagaatta tttttatacac    2760 agattctgcc ttgtttcata gtatgagggt tgaagacgga aaacaatcta agggtctctc    2820 attttttttaa ttttgtttttg ttcagtttgg ttttttttt tttttgcgct gctaagaagc    2880
taaagtcatc catccttatt cacgttgaca gtacctagct gtaatgtttc acagagtgtg    2940
ctgctatttt ataaacattt ttataatata ttatttact gcttaaattc caagtcctga    3000
agtagatggt tgagatatga gttcttcgta ctggaaaagc ccttccgtag tttgttttct    3060
tctggtagca tattcatggt tgttttttt tttcttttt ggtttttgg ttttttttt    3120 ttcctctgat cacattcttc aaagacggag tattctttac ctcaggttta ctggacaaaa    3180
tcaataacta caaaaggcaa tgattcacgc ttttgttttc ataataccctc acaaccgtac    3240 agtttctgct tgggagccca ttcgcatgag gaatacagaa gcagtgtgag cagggctgac    3300
tccctctcag gtggaaggca gggcggtctc actcccaggg acctttttgg tcatggaggc    3360
catcgggctc ccagttagac cctggtatcc tcatcatgat ggaaaaaata cattgaacca    3420
agggatcctc cctcccctcc aaggcagacg ttcagtacaa acatttatgc ggtaggctca    3480
gatgtcgtaa tttgcactta ggtaccaggt gtcaggaaac agactaaaaa gaattccacc    3540
aggctgtttg gagatcctca tcttggagct ttttcaaaag cggggcttca tctgcaaagg    3600
gccctttcat cttgaagttt ttcccctccg tctttcccct ccctggcat ggacaccttg    3660 tgtttaggat catctctgca ggtttcctag gtctgaatct gcgagtagat gaacctgcag    3720
caagcagcgt ttatggtgct tccttctccc tcctctgtct caaactgcgc aggcaagcac    3780
tatgcaagcc caggccctct gctgagcggt actaaacggt cgggttttca atcacactga    3840
attggcagga taagaaaaat aggtcagata agtatgggat gatagttgaa gggaggtgaa    3900
gaggctgctt ctctacagag gtgaaattcc agatgagtca gtctcttggg aagtgtgttt    3960
agaagggttc aggactttgt gagttagcat gaccctaaaa ttctagggga tttctggtgg    4020
gacaatgggt ggtgaattct gaagttttgg agagggaagt ggagcagcca gcaagtaagc    4080
tagccagagt tttctcaaga gccagctttg ctcagcacac tctcctgggc cccaaggagt    4140 cccacgaat gggaaagcg ggaaccctgg agttcttggg aatcttggag cctaaagaga    4200
aaccgaggtg caaattcatt tcatggtgac tgacccttga gcttaaacag aagcagcaaa    4260
```

```
tgaaagaacc ggacaaataa ggaagggcac aagcctaccc gactctattt acagtctgta    4320
actttccact cttcctgtag tcccgaggcc cctgggtcct tctagctttt ctctttccca    4380
tccttggggc cttgtgtgat gatgggtgtg gggctgccga tgggaaagtc ggggggttgtt   4440 aggcttttct gcctgctcct gcttaaacac aagaaggaat cctggatttt gccctctcct    4500
tagctcttag tctctttggt aggagttttg ttccagagga gctctccccc ttggatttga    4560
acttgctctt tttgttgttg ttgttctttc tcttcttttt cttacctccc actaaagggg    4620
ttccaaatta tcctggtctt tttctacctt gttgtgtttc tatctcgtct ttacttccat    4680
ctgtttgttt ttttctccat cagtgggggc cgagttgttc ccccagcctg ccaaattttg    4740
atccttcccc tcttttggcc aaatcctagg gggaagaaat cctagtatgc caaaaatata    4800
tgctaagcat aattaaactc catgcgggtc cataacagcc aagaagcctg caggagaaag    4860
ccaagggcag ttccctccgc agaacacccc atgcgtgctg agaggcgagc tccttgaaga    4920
aggggctgtt cttccaggag gcctattttt gaactgcctc aggaccccac tggagagcac    4980
agcatgcctt actactgggt catccttggt ctatgtgctc tgtactggag gctctgttct    5040
gcctcttatc agccaggtca ggggcacaca tggcttaagt gacaaagcca gaggagaaga    5100
caaccctgac agcatcacgc tgcatcccat tgctagcagg attggcaact cttcagacgg    5160
agctgcgctt ccctgcagtc tagcacctct agggcctctc cagactgtgc cctgggagct    5220
ctgggactga aggttaaga acataaggca ggatcagatg actctctcca agagggcagg    5280
ggaattttct ctccatgggc cacaggggac agggctggga aagaaatag acttgcacct    5340 tatgtcatgt aaataattga ttttctagtt caagaagata atattggtag tgtgggaatt    5400
ggaggtagga aggggaggaa gtctgagtaa gccagttggc ttctaagcca aaaggattcc    5460
tctttgttta tctctgagac agtccaacct tgagaatagc tttaaagggg aaattaatgc    5520
tgagatgata aagtcccctt aagccaacaa accctctgta gctatagaat gagtgcaggt    5580
ttctattggt gtggactcag agcaatttac aagagctgtt catgcagcca tccatttgtg    5640 caaaatagggg taagaagatt caagaggata tttattactt cctcatacca catggctttt    5700
gatgattctg gattctaaac aacccagaat ggtcatttca ggcacaacga tactacattc    5760
gtgtgtgtct gcttttaaac ttggctgggc tatcagaccc tattctcggc tcaggttttg    5820
agaagccatc agcaaatgtg tacgtgcatg ctgtagctgc agcctgcatc ccttcgcctg    5880
cagcctactt tggggaaata aagtgcctta ctgactgtag ccattacagt atccaatgtc    5940
ttttgacagg tgcctgtcct tgaaaaacaa agtttctatt tttatttta attggtttag     6000 ttcttaactg ctggccaact cttacatccc cagcaaatca tcgggccatt ggatttttc     6060 cattatgttc atcaccctta tatcatgtac ctcagatctc tctctctctc ctctctctca    6120
gttatgtagt ttcttgtctt ggactttttt ttttcttttc ttttctttt tttttttgct     6180 ttaaaacaag tgtgatgcca tatcaagtcc atgttattct ctcacagtgt actctataag    6240
aggtgtgggt gtctgtttgg tcaggatgtt agaaagtgct gataagtagc atgatcagtg    6300
tatgcgaaaa ggttttagg aagtatgca aaaatgttgt attggctatg atggtgacat       6360
gatatagtca gctgccttt aagaggtctt atctgttcag tgttaagtga tttaaaaaaa      6420
taataacctg ttttctgact agtttaaaga tggatttgaa aatggttttg aatgcaatta    6480
ggttatgcta tttggacaat aaactcacct tgacctaaat taaaaaaaaa a             6531
```

IDENTIFICATION OF MULTI-MODAL ASSOCIATIONS BETWEEN BIOMEDICAL MARKERS

FIELD OF THE INVENTION

The present invention relates to a method for identifying multi-modal associations between biomedical markers which allows for the determination of network nodes and/or high ranking network members or combinations thereof, indicative of having a diagnostic, prognostic or predictive value for a medical condition, in particular ovarian cancer. The present invention further relates to a biomedical marker or group of biomedical markers associated with a high likelihood of responsiveness of a subject to a cancer therapy, preferably a platinum based cancer therapy, wherein said biomedical marker or group of biomedical markers comprises at least 1, 2, 3, 4, 5, 6, 7, 8, 9, 10, 11, 12, 13, 14, 15, 16, 17, 18, 19, 20 or all markers selected from PKMYT1, SKIL, RAB8A, HIRIP3, CTNNB1, NGFR, ZCCHC11, LSP1, CD200, PAX8, CYBRD1, HOXC11, TCEAL1, FZD10, FZD1, BBS4, IRS2, TLX3, TSPAN2, TXN, and CFLAR. Furthermore, an assay for detecting, diagnosing, graduating, monitoring or prognosticating a medical condition, or for detecting, diagnosing, monitoring or prognosticating the responsiveness of a subject to a therapy against said medical condition, in particular ovarian cancer, is provided, as well as a corresponding method for classifying a subject and a medical decision support system.

BACKGROUND OF THE INVENTION

Ovarian cancer is the leading cause of death from gynecological malignancies mainly due to its late diagnosis, high mortality and low 5-year survival rates of only 30%. Reasons for this poor outcome include non specific presenting symptoms and identification in advanced stages of disease, mainly due to the absence of reliable screening methods for early detection. Ovarian cancer is the $6^{th}$ most common cancer world-wide with 204,000 cases and 125,000 deaths worldwide. The exact cause of developing ovarian cancer is still unknown; however, women with certain risk factors may be more likely than others to develop ovarian cancer. The top ranking factors include age, parity (like for breast cancer), personal and drug history.

Besides the correct and timely diagnosis of ovarian cancer, its treatment poses major challenges. Advanced ovarian cancer patients frequently receive carboplatinum as standard chemotherapy. Most patients initially respond to this chemotherapy. However, up to 75% of initial platinum responders recur with chemoresistant tumor within the first 2 years and eventually succumb to metastatic disease. In addition, a small fraction of ovarian cancers are primarily refractory to platinum compounds.

Thus, information about how a cancer develops through molecular events could not only be very helpful for diagnostic purposes and allow to improve the clinical outcome in patients with cancer at its earliest stage, while it is still localized and readily treatable, but also allow a clinician to predict more accurately how such a cancer is likely to respond to specific therapeutic treatments. In this way, a regimen based on knowledge of the tumor's sensitivity can be rationally designed. Hence, characterization of a cancer patient in terms of predicting treatment outcome enables the physician to make an informed decision as to a therapeutic regimen with appropriate risk and benefit trade-offs to the patient.

US Patent application 20090011049 is related to the area of cancer prognosis and therapeutics and discloses aberrant methylation patterns of particular genes in cancers. Here, the silencing of nucleic acids encoding a DNA repair or DNA damage response enzyme was used prognostically and for selecting treatments that are tailored for an individual patient. Combinations of these markers were used to provide prognostic information.

Although several genes are reported to be differentially regulated in certain cancer types and cancer therapy resistance situations, it is difficult to integrate this information in order to predict a course of events for patients suffering from or being examined for cancer, in particular ovarian cancer, and to assess early therapeutic resistance, in particular a resistance to platinum based therapeutics.

There is thus a need for an improved method for providing cancer prognostic information, as well as assays and diagnostic methods based thereon.

SUMMARY OF THE INVENTION

The present invention addresses this need and provides means and methods which allow the identification of stratifying genes based on multiple high-throughput modalities.

The above objective is in particular accomplished by a method for identifying multi-modal associations between biomedical markers comprising the steps of:

obtaining a plurality of datasets comprising data on multiple molecular profiling modalities from a plurality of primary subjects;

obtaining a plurality of datasets comprising data on multiple molecular profiling modalities from a plurality of secondary subjects;

correlating the pluralities of datasets comprising data on multiple molecular profiling modalities of primary and secondary subjects;

identifying one or more stratifying biomedical markers which have different values for the primary subjects and the secondary subjects;

identifying a network and/or sub-network among the stratifying biomedical markers;

assigning a ranking score to the members of the identified network, said ranking score being based upon a network metric;

determining network nodes and/or high ranking network members or combinations thereof, indicative of having a diagnostic, prognostic or predictive value for a medical condition.

This method provides the advantage of being able to provide predictive information at an early developmental stage of a disease, e.g. a cancer disease, in particular ovarian cancer. Furthermore, it allows the assessment of a therapeutic resistance, such as a resistance to platinum based therapeutics like carboplatinum. The methodology has successfully been used to identify stratifying genes between resistant and sensitive chemotherapy patients.

In a preferred embodiment of the present invention said plurality of datasets on multiple profiling modalities from a plurality of primary and secondary subjects comprises data on methylated loci and on gene expression.

In a further preferred embodiment of the present invention the step of identifying a network and/or sub-network comprises the calculation of significance values for the stratifying biomedical markers.

In another preferred embodiment of the present invention said network metric comprises at least one element selected from the group of connectivity, adjacency, network density, network centralization, network heterogeneity, cliquishness, hub gene significance, network significance, centroid conformity, betweenness, centricity, closeness and eccentricity.

In another preferred embodiment of the present invention said biomedical marker is a gene, a genomic locus in a coding region, a genomic locus in a non-coding region, a transcript and/or a protein.

In yet another preferred embodiment of the present invention said primary subject is a healthy subject and said secondary subject is affected by a medical condition.

In a particularly preferred embodiment of the present invention, said medical condition is cancer.

In another particularly preferred embodiment of the present invention said cancer is ovarian cancer.

In a further preferred embodiment of the present invention, said predictive value is the indication of likelihood of responsiveness of a subject to a therapy comprising one or more platinum based drugs.

In a particularly preferred embodiment of the present invention said platinum based drug is carboplatinum.

In another aspect the present invention relates to a biomedical marker or group of biomedical markers associated with a high likelihood of responsiveness of a subject to a cancer therapy, preferably a platinum based cancer therapy, wherein said biomedical marker or group of biomedical markers comprises at least 1, 2, 3, 4, 5, 6, 7, 8, 9, 10, 11, 12, 13, 14, 15, 16, 17, 18, 19, 20 or all markers selected from PKMYT1, SKIL, RAB8A, HIRIP3, CTNNB1, NGFR, ZCCHC11, LSP1, CD200, PAX8, CYBRD1, HOXC11, TCEAL1, FZD10, FZD1, BBS4, IRS2, TLX3, TSPAN2, TXN, and CFLAR, indicated in Table 1.

In a further aspect the present invention relates to an assay for detecting, diagnosing, graduating, monitoring or prognosticating a medical condition, or for detecting, diagnosing, monitoring or prognosticating the responsiveness of a subject to a therapy against said medical condition, preferably cancer, more preferably ovarian cancer, comprising at least the steps of (a) testing in a sample obtained from a subject for the expression of a stratifying biomedical markers or group of said markers and/or of a network node and/or high ranking network member or group of said nodes or members obtained by a method as defined herein above, or as defined in the list or group of biomedical markers described herein above or below;

(b) testing in a control sample for the expression of the same marker, group of markers, network node, high ranking network member of group thereof as in (a);

(c) determining the difference in expression of markers of steps (a) and (b); and (d) deciding on the presence or stage of a medical condition or the responsiveness of a subject to a therapy against said medical condition, preferably cancer, more preferably ovarian cancer, based on the results obtained in step (c).

In a preferred embodiment of the present invention said assay comprises the additional step of testing in a sample obtained from a subject for the methylation state and/or pattern of a stratifying biomedical marker or group of said markers and/or of a network node and/or high ranking network member or group of said nodes or members obtained by a method as defined herein above, or as defined in the list or group of biomedical markers described herein above, wherein in step (c) additionally the difference in methylation state and/or pattern is determined.

In a further aspect the present invention relates to a method for classifying a subject comprising:

(a) providing a subject's dataset comprising data on methylated loci and data on gene expression of a stratifying biomedical marker or group of said markers and/or of a network node and/or high ranking network member or group of said nodes or members obtained by a method as defined herein above, or as defined in the list or group of biomedical markers described herein above or below;

(b) accessing a database comprising database values for a stratifying biomedical marker or group of said markers and/or of a network node and/or high ranking network member or group of said nodes or members obtained by a method as defined herein above, or as defined in the list or group of biomedical markers described herein above or below; and (c) calculating a subject's classification score based on the difference between database between the results of step (a) and (b).

In a further aspect the present invention relates to a medical decision support system comprising:

an input for providing a subject dataset comprising data on methylated loci and data on gene expression of a stratifying biomedical marker or group of said markers and/or of a network node and/or high ranking network member or group of said nodes or members obtained by a method as defined herein above, or as defined in the list or group of biomedical markers described herein above;

a computer program product for enabling a processor to carry out the method for classifying a subject comprising as define above; and an output for outputting the subject classification score.

DETAILED DESCRIPTION OF EMBODIMENTS

Figure 1:
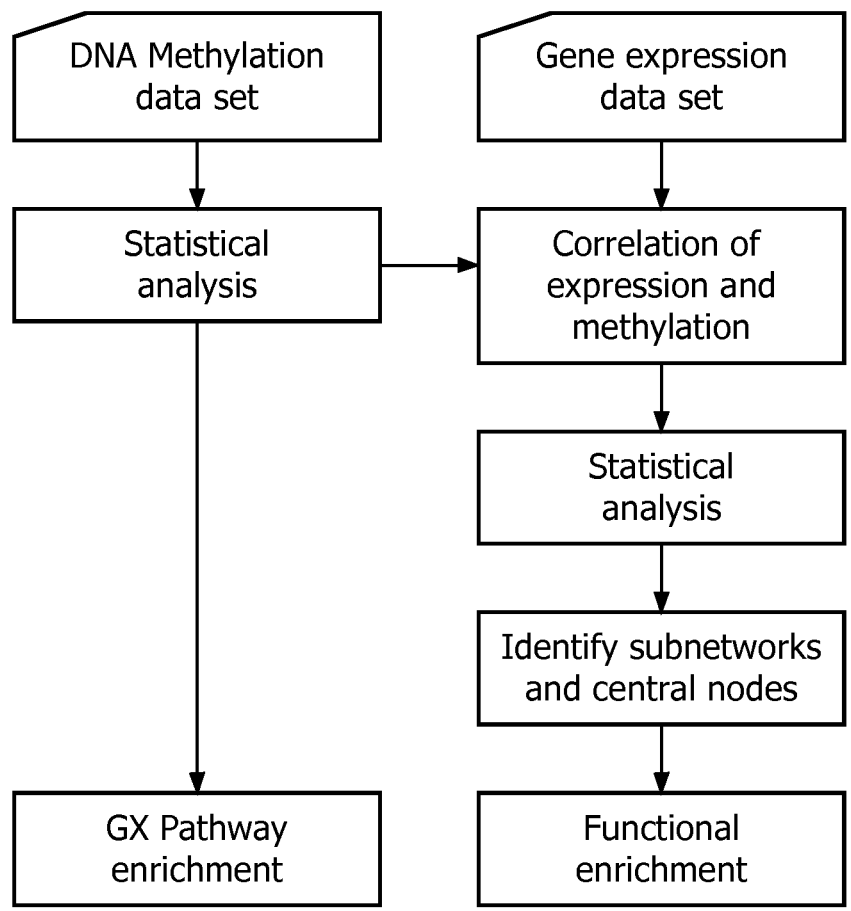
FIG. 1 shows a flow chart of the analyses to indentify key pathways and genes in platinum resistance.

The inventors have developed means and methods which allow the identification of stratifying genes based on multiple high-throughput modalities.

Although the present invention will be described with respect to particular embodiments, this description is not to be construed in a limiting sense.

Before describing in detail exemplary embodiments of the present invention, definitions important for understanding the present invention are given.

As used in this specification and in the appended claims, the singular forms of "a" and "an" also include the respective plurals unless the context clearly dictates otherwise.

In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention the term "consisting of" is considered to be a preferred embodiment of the term "comprising of". If hereinafter a group is defined to comprise at least a certain number of embodiments, this is meant to also encompass a group which preferably consists of these embodiments only.

Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)" etc. relate to steps of a method or use there is no time or time interval coherence between the steps, i.e. the steps may be carried out simultaneously or there may be time intervals of seconds, minutes, hours, days, weeks, months or even years between such steps, unless otherwise indicated in the application as set forth herein above or below.

It is to be understood that this invention is not limited to the particular methodology, protocols, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

As has been set out above, the present invention concerns in one aspect a method for identifying multi-modal associations between biomedical markers comprising the steps of:

obtaining a plurality of datasets comprising data on multiple molecular profiling modalities from a plurality of primary subjects;

obtaining a plurality of datasets comprising data on multiple molecular profiling modalities from a plurality of secondary subjects; gene expression from a plurality of primary subjects;

correlating the pluralities of datasets comprising data on multiple molecular profiling modalities of primary and secondary subjects;

identifying one or more stratifying biomedical markers which have different values for the primary subjects and the secondary subjects;

identifying a network and/or sub-network among the stratifying biomedical markers;

assigning a ranking score to the members of the identified network, said ranking score being based upon a network metric;

determining network nodes and/or high ranking network members or combinations thereof, indicative of having a diagnostic, prognostic or predictive value for a medical condition.

The term "biomedical marker" as used herein refers to a molecular, genetic, medical, biochemical, chemical, biological or physical condition associated with a subject, which may vary from one subject to another, e.g. from a subject afflicted by disease to a healthy subject.

The term "multiple molecular profiling modalities" as used herein refers to a modality associated with a molecular, genetic, medical, biochemical, chemical, biological or physical condition linked to a subject, e.g. a patient to be tested. Non-limiting examples of such modalities comprise the molecular state of a gene or genomic locus, the presence or absence or amount/level of transcripts, proteins, truncated transcripts, truncated proteins, the presence or absence or amount/level of cellular markers, the presence or absence or amount/level of surface markers, the presence or absence or amount/level of glycosylation pattern, the form of said pattern, the presence or absence of expression pattern on mRNA or protein level, the form of said pattern, cell sizes, cell behavior, growth and environmental stimuli responses, motility, the presence or absence or amount/level of histological parameters, staining behavior, the presence or absence or amount/level of biochemical or chemical markers, e.g. peptides, secondary metabolites, small molecules, the presence or absence or amount/level of transcription factors, the form and/or activity of chromosomal regions or loci, as well as further modalities referring to the mentioned conditions or referring to additional conditions known to the person skilled in the art.

The term "plurality of datasets" refers to datasets comprising data on the above mentioned conditions, e.g. comprising data on profiles of one or more of the molecular, genetic, medical, biochemical, chemical, biological or physical conditions associated with a subject. A plurality of datasets may comprise at least one dataset, or more than one dataset, e.g. 2, 3, 4, 5, 6, 7, 8, 9, 10, 20, 50, 100 or more datasets. The datasets may comprise redundant or non-redundant information. The datasets may be provided in any suitable form known to the person skilled in the art, e.g. in suitable input formats for bioinformatic applications, as raw data etc.

The term "primary subjects" as used herein refers to a group of subjects, e.g. animals, in particular mammals. Preferably, a primary subject is a human being, e.g. a patient. The term may, in a specific embodiment, also refer to a sample obtained from a subject. Primary subjects are distinguished form a corresponding group of "secondary subjects" in that they can be associated with one or more of the mentioned molecular, genetic, medical, biochemical, chemical, biological or physical conditions associated with a subject which differ between the primary and secondary subjects.

The term "correlating the pluralities of datasets" as used herein means that the datasets or the comprised information is compared, e.g. between the datasets obtained from the primary and the secondary subjects and/or with datasets derivable from data repositories, from external sources, from literature values, from parallel examinations or the like. Furthermore, the term may include the performance of statistical analyses or procedure. The term thus also means determining the influence of one marker in one modality to another marker's value in another modality. In a preferred embodiment the correlation is a statistically significant relationship or its variation between primary and secondary subjects.

The terms "stratifying biomedical markers" as used herein refers to conditions or features associated with the subjects, being derivable from or associated with the mentioned molecular, genetic, medical, biochemical, chemical, biological or physical condition used as input for the correlation step, wherein these conditions or features separate primary and secondary subjects. Thus, stratifying biomedical markers are differentiating conditions selected from the initially obtained plurality of datasets. In a typical embodiment, these biomedical markers show different values for the mentioned molecular, genetic, medical, biochemical, chemical, biological or physical condition, preferably the values are different in a statistically significant way. The term includes one differentiating marker, but also more than one such marker, e.g. a group of 2, 3, 4, 5, 6, 7, 8, 9, 10 or more markers. The stratification may be based then on comparison operations between the members of the group, e.g. be based on average values over the entire group or other statistical procedures known to the person skilled in the art.

The term "identifying a network" as used herein refers to the identification of relevant relationships between the biomedical markers. The term "relevant" means that suitable statistical procedures as known to the person skilled in the art may be employed in order to determine whether the relationship is significant. Typically, threshold values may be employed or suitable algorithms based on exclusion thresholds in order to eliminate relationships without medical or biological importance or without diagnostic or therapeutic medical value. The procedures may be repeated one or several times. Furthermore, the threshold or elimination values may be changed or varied, e.g. in dependence of the marker under considerations, the number of markers under consideration, the size of the obtained network etc. The "network" requires that every member of the network has at least one relationship or association with another member of the network. Preferably, the network members have more than one relationship or association with one or more other members of the network. Non-limiting examples of networks which may be identified are genetic or biochemical pathways, co-localized genetic markers or genetic loci, markers based on similar environmental inputs, target genes activated by transcription factors, etc.

The term "identifying a sub-network" as used herein means that within an already identified conjunction of markers or elements having relationships with other members of the network a sub-set of members is identified, which show a different type of relationship or a higher degree thereof (e.g. higher values with regard to certain conditions etc.). The term sub-network also comprises networks which only partially overlap with networks. The term also refers to more than one order of hierarchy between the networks, e.g. to sub-sub-networks etc. For example, a sub-network may be enriched in certain clinical parameters from a database, in certain pathway members, in the presence or absence of certain pathways, in genomic locations, the presence of chromosomes etc.

In the context of the present invention, the term "ranking score" refers to a score representing a numerical value. Preferably, the ranking score may be based upon a network metric. The term "network metric" refers to a measurement of performance in the network system. The term may also comprise a composite of two or more independent measures, typically in the form of a ratio. However, other combinations of measures are also possible.

One of the final steps of the method of identifying multi-modal associations between biomedical markers is the determination of network nodes. The term "network node" as used herein refers to a member of the network which shows more than a single association with other network elements.

In a preferred embodiment a network node is a multi association element or network hub. The term "network hub" means a node with a number of connections being larger than an average number of connections per node in a given network.

More preferably an important network hub is identified. The term "important network hub" as used herein refers to a hub with a number of connections being larger than an average number of connections per hub in a given network.

The method may also result in the identification of high ranking network members. The term "high-ranking network members" means that the ranking score of the members of the network is higher than the average ranking score of network members. In a specific embodiment such members may not only have one high-ranking score, but preferably 2, 3, 4, 5 or more. In yet another embodiment, the associations and/or ranking scores may be combined, e.g. a determination step may be based on two or more different informational elements such as nodes and/or hubs and/or important hubs and/or high-ranking network members or any sub-grouping thereof.

These nodes or network members may be indicative for medical conditions or have a diagnostic, prognostic or predictive value for a medical condition. The term "medical condition" as used herein refers to medical situation which differs from a healthy or normal state, e.g. a disease or a predisposition for a disease. The term "diagnostic value for a medical condition" means that one, 2, 3, 4, 5 or more values for a molecular, genetic, medical, biochemical, chemical, biological or physical condition associated with one, 2, 3, 4, 5, 6 identified nodes or network members, respectively, may upon arriving at typical thresholds, e.g. above or below conditions derived from primary subjects as defined above, be considered as indicating the presence of a medical condition, e.g. of a disease or a predisposition for a disease. The term "prognostic value for a medical condition" refers to the prognosis of the development of a medical condition, e.g. form predisposition towards an acute illness, or from a less advanced stage to a more advanced stage, depending on one, 2, 3, 4, 5 or more values for a molecular, genetic, medical, biochemical, chemical, biological or physical condition associated with one, 2, 3, 4, 5, 6 identified nodes or network members, respectively.

The term "predictive value for a medical condition" refers to a value allowing the assessment of a medical condition or the development of said medical condition in the future, e.g. within a defined time frame of 1 to 3 weeks, 1 month, 2 month, 3 month, 4 months, 5 months, 6 months, 1, 2, 3, 4, 5, 6, 7, 10 years or more years or any other period of time. The term also includes all situations associated with said medical condition, e.g. treatment results, responsiveness to treatments, development of resistance etc.

In a preferred embodiment of the present invention the plurality of datasets on multiple molecular profiling modalities from a plurality of primary and secondary subsections comprises data on methylated loci and/or data on gene expression. Particularly preferred are data on methylated loci in combination with data on gene expression.

The term "methylated locus" as used herein refers to a nucleic acid derived from or present in a subject which is characterized by the presence of 5-methylcytosine ("5-mCyt") at one or a plurality of CpG dinucleotides within said nucleic acid. For example, such nucleic acid sequences may be genomic portions or loci which are derived from or which are present in a subject. These loci may, for example, comprise active or inactive portions of the genome. Preferably such loci are genes including all necessary elements for expression of the encoded genetic information, e.g. cis and trans acting elements etc. The information on methylated loci may preferably comprise information on the methylation state of said locus or genomic region or gene or any sub-fragment thereof.

In the context of the present invention the term "methylation state" means the degree of methylation present in a nucleic acid of interest. This may be expressed in absolute or relative terms, i.e. as a percentage or other numerical value or by comparison to another tissue and therein described as hypermethylated, hypomethylated or as having significantly similar or identical methylation status.

The term "hypermethylation" or "hypermethylated" as used herein refers to the average methylation state corresponding to an increased presence of 5-mCyt at one or a plurality of CpG dinucleotides within a DNA sequence of a test DNA sample, relative to the amount of 5-mCyt found at corresponding CpG dinucleotides within a normal control DNA sample.

The term "hypomethylation" as used herein refers to the average methylation state corresponding to a decreased presence of 5-mCyt at one or a plurality of CpG dinucleotides within a DNA sequence of a test DNA sample, relative to the amount of 5-mCyt found at corresponding CpG dinucleotides within a normal control DNA sample.

Thus, in a preferred embodiment the "methylated locus" may show a hypermethylation, a hypomethylation or an unmodified methylation status in comparison to a the methylation state of a primary subject.

The locus or the loci to be analysed may comprise any suitable dimension known to the person skilled in the art. For example, fragments of about 5, 10, 20, 50, or 100 nucleotides, of about 1 kbp, 2 kbp, 3 kbp, 4 kbp 5 kbp, 6 kbp, 7 kbp 10 kbp, 15 kbp, 20 kbp, 25 kbp, 30 kbp, 35 kbp, 40 kbp, 100 kbp, entire chromosomes, more than one chromosome (e.g. 2, 3, 4, 5, 6 etc. chromosomes), or the entire genome may be analysed with regard to the methylation state.

In one embodiment the epigenetic analysis of single genes (including all elements necessary for their expression, e.g. promoter, enhancer elements, open reading frame, terminator etc. or only sub-fragments thereof), or of conjunctions of genes, e.g. of pathway members, or of any combination or conjunction of genes is envisaged. Further envisaged is the epigenetic analysis of regulatory regions. The term "regulatory region" means a nucleotide sequences which affect the expression of a gene. Said regulatory regions may be located within, proximal or distal to said gene. The regulatory regions include but are not limited to constitutive promoters, tissue-specific promoters, developmental-specific promoters, inducible promoters, as well as non-coding RNAs (such as microRNAs) and the like. Promoter regulatory elements may also include certain enhancer sequence elements that control transcriptional or translational efficiency of the gene. These sequences can have various levels of binding specificity and can bind to transcription factors as well as DNA methyl-binding proteins, e.g. MeCP, Kaiso, MBD1-MBD4. The term "epigenetic" as used herein refers to the modification of biological, i.e. genetic behavior due to changes other than changes in the underlying DNA sequence. Typical, non-limiting examples of epigenetic modifcations are methylation of a genomic sector or locus, chromatin remodeling, or the interaction of DNA with RNA transcripts. Thus, besides or in addition to the analysis of methylation or methylation pattern or states also the status of chromatin and/or the presence of interaction RNA species may be determined.

The term "pathway" as used herein refers to the set of interactions occurring between a group of genes, which genes depend on each other's individual functions in order to make the aggregate function of the network available to the cell.

Methylation may be determined with any suitable means known to the person skilled in the art, for example, with an methylation assay, e.g. an assay for determining the methylation state of one or more CpG dinucleotide sequences within a sequence of DNA. Such assays may be based on the employment of methylation specific PCR or methylation specific sequencing to assess the level of DNA methylation. Details would be known to the person skilled in the art.

"Gene expression" as used herein refers to the transcription and/or translation of a gene. "Gene expression" or lack thereof may be a consequence of epigenetic modifications of the genomic DNA associated with the marker gene and/or regulatory or promoter regions thereof etc. Genetic modifications may include SNPs, point mutations, deletions, insertions, repeat length, rearrangements, copy number variations and other polymorphisms. The analysis of either the expression levels of protein, or mRNA expression are summarized as the analysis of "expression" of the gene. The term refers to the expression of a single gene, may however also comprise the expression of a group of genes, .e.g. genes located in a pathway, genes co-localized in a genomic region, genes present on a chromosome or in a chromosomal region etc.

In one embodiment of the invention datasets on the methylation state as described above are analysed in conjunction with one ore more other datasets on a molecular, genetic, medical, biochemical, chemical, biological or physical conditions as defined above.

In another embodiment of the invention datasets on gene expression as described above may be analysed in conjunction with one or more datasets on a molecular, genetic, medical, biochemical, chemical, biological or physical conditions as defined above.

Particularly preferred is an analysis of datasets on the methylation state and datasets on gene expression. For example, data on the expression of a gene or of pathway members or of co-localized genes etc. may be correlated with the methylation state or epigenetic status of the very same elements or of neighboring elements or structures, or vice versa. Alternatively, data on the expression of a gene or of pathway members etc. may be correlated with the methylation state or epigenetic status of a different gene or a member of different pathways, e.g. of elements associated on a different level or in a different manner, or vice versa.

In a further embodiment of the invention the step of identifying a network and/or sub-network comprises the step of calculating significance values for the stratifying biomedical markers. The term "significance value" as used herein refers to any suitable statistical value which allows a statistically relevant distinction between two situations. Preferably, the term relates to the calculation of p-values. More preferably, the significance value may be a p-value based on the Hypergeometric distribution or Fisher's exact test.

In a specific embodiment, the calculation of a significance value may be performed according to the following example. Under the assumption that there are N genes, where N would be the number of genes present in primary and secondary datasets and that M genes are linked by a different profiling modality, e.g. annotated to a specific pathway in the set of pathways, or associated by any other mean, n genes are found to be in the input list, such as comprised within the stratifying genes, for example differentially methylated, k represents the number of genes from the input list which are also annotated to the specific pathway. The probability for any given k, where k is an integer in the set of integers from 1 to n, can then be calculated according to the formula:

$$h(k\mid N;M;n) := P(X = k) = \frac{\binom{M}{k}\binom{N-M}{n-k}}{\binom{N}{n}}$$

In a further embodiment of the present invention, the calculation of significance values for the stratifying biomedical markers may be supplemented with the performance of a suitable correction procedure. A particularly preferred procedure is the Benjamini & Hochberg False Discovery Rate (FDR) correction.

In a further embodiment of the invention the network metric to the assessed comprises at least one element selected from the group of connectivity, adjacency, network density, network centralization, network heterogeneity, cliquishness, hub gene significance, network significance, centroid significance, centroid conformity, betweenness, centricity, closeness and eccentricity.

The term "connectivity" as used herein refers to the number of network elements, e.g. genes, adjacent to a network element, e.g. gene, or that are directly linked.

The terms "adjacency" or "closeness" as used herein refers to the number of network elements, e.g. genes, which do not form neutral relationships, e.g. like or dislike others.

The term "network density" as used herein refers to the mean off-diagonal adjacency. This metric measures the overall affection among network elements, e.g. genes.

The term "network centralization" refers to topological structures of a network. For example a centralization of 1 indicates a network with star topology, whereas a centralization of 0 indicates a network where each node has the same connectivity.

The term "network heterogeneity" as used herein refers to the variance of connectivity.

The term "cliquishness" as used herein refers to a density measure of local connections.

The term "hub gene significance" as used herein refers to the association between connectivity and gene significance.

The term "network significance" as used herein refers to the average of gene significance of the genes. This is typically a measure of the average grade point average among the network elements, e.g. genes.

The term "centroid significance" or "centricity" as used herein refers to the gene significance of a suitably chosen representative node (centroid) in a the network.

The term "centroid conformity" as used herein refers to the adjacency between a network element, e.g. a gene, and a suitably chosen representative node (centroid).

The term "betweenness" as used herein refers to a high influence of a network element, e.g. gene, over the information flow between other elements, e.g. genes, in the network.

The term "eccentricity" as used herein refers the accessibility of an element of the network, e.g. a gene, by all other elements, e.g. genes, in the network.

Further details as well as formula for the calculation of the corresponding metrics may be derived from suitable scientific publications known to the person skilled in the art, e.g. from Horvath and Dong, PLoS Computational Biology, 2008, 4(8), e1000117, pages 1 to 27 (which is incorporated herein in its entirety), in particular from pages 3 to 7.

The metrics as mentioned above may be determined according to suitable methods known to the person skilled in the art, e.g. as described in Horvath and Dong. Metrics may be used alone or in any combination. Preferably, the betweenness and/or the eccentricity and/or the connectivity of elements of the network, e.g. of genes, may be determined. For example, the betweenness of network elements, e.g. genes, may be used as ranking method, and the eccentricity and/or connectivity may additionally be used in order to increase the significance of the network element and/or to eliminate non-significant elements. A typical example of such a ranking is provided in Table 3.

In a preferred embodiment of the present invention a ranking score is assigned to a network element or node, e.g. a gene, according to the metric betweenness. In a non-limiting example, only network elements or nodes, e.g. genes, are considered which show a betweenness value of 0.00005 or higher, e.g. 0.0001, 0.00015, 0.0002 etc. In a further embodiment a ranking score is assigned to a network element or node, e.g. a gene, according to the metric eccentricity. In a non-limiting example, only genes are considered which show an eccentricity value of about 1.35 and higher, e.g. about 1.4, 1.45, 1.5, 1.55, 1.6, 1.65, 1.7 or higher etc. In yet another embodiment a ranking score is assigned to a network element or node, e.g. a gene, according to the metric connectivity. In a non-limiting example, only network elements or nodes, e.g. genes, are considered which show a connectivity value of about 2 or higher, e.g. about 3, 4, 5, 6, 7, 8, 9, 10, 15 or higher etc. In another embodiment of the present invention the ranking scores of betweenness, eccentricity and/or connectivity may be combined. The combination may be weighted according to any ranking list mentioned above, e.g. according to the ranking of betweenness, or according to the ranking of eccentricity, or according to the ranking of connectivity, or according to groups of two of the rankings etc.

In a further embodiment any of the other mentioned metrics, i.e. adjacency, network density, network centralization, network heterogeneity, cliquishness, hub gene significance, network significance, centroid significance, centroid conformity, centricity and closeness may also be used as primary ranking input, i.e. for the definition of a ranking score. Accordingly obtained rankings may further be combined with rankings derived from metrics such as betweenness, eccentricity and/or connectivity or any other of the above mentioned group, e.g. as secondary ranking input. A combination may be calculated according to suitable methods, e.g. be based on the average ranking position, or be based on an weighting factor, e.g. according to importance and/or significance of the metric input.

In a specific embodiment of the present invention the method for identifying multi-modal associations between biomedical markers may be carried out with the help of suitable software tools such as BingGO and/or Cytoscape. In a non-limiting example, the following steps may be carried out:

(a) importing network metrics as attributes of the nodes;
(b) selecting a subset of nodes (e.g. top ranked nodes) and edges (e.g. most correlated and anti-correlated nodes), e.g. with a threshold value of 0.5;
(c) invoking of the BingGO plug-in for Cytoscape (further details are described in Maere et al., BINGO: a Cytoscape plugin to assess overrepresentation of Gene Ontology categories in biological networks, Bioinformatics, 2006, 21, 3448, which is incorporated herein in its entirety);

(d) parameters for BinGO may be set (e) ontology: Molecular_Function/Biological Process may be selected (f) annotation (organism): Homo sapiens may be selected;

(g) statistical test: Hypergeometric test may be selected;

(h) correction: Benjamin & Hochberg False Discovery Rate (FDR) correction may be selected;

(i) significance level may be set to 0.05;

(j) testing options may be set to: Test cluster versus whole annotation;

(k) the analysis, e.g. overrepresentation analysis, may be executed.

In a further preferred embodiment of the invention the biomedical marker to be assessed or analysed is a gene, a genomic locus, a transcript and/or a protein. A gene may be an entity comprising all necessary elements ensuring expression of the gene, e.g. promoter, enhancer, open reading frame, terminator or sub-groups thereof. A genomic locus as used herein may be a genomic locus which is located in a non-coding region. Alternatively, the genomic locus may be located in a coding-region. The genomic locus may be of a different size, e.g. encompassing a short fragment of 10 to 1000 nucleotides, or larger fragments of 2 kbp, 5 kbp, 10 kbps, 100 kbp, 1 Mbp, chromosomal arms, or entire chromosomes.

The genomic locus may also be located partially in a coding region and partially in a non-coding region.

The transcript may be any form of nucleic acid derived from an active gene, e.g. an mRNA molecule, a non-spliced mRNA molecule, a truncated mRNA molecule, short fragments thereof etc. The protein may be a full-length protein, or any fragment thereof. Alternatively, an antibody or a ligand specifically binding to the protein, binding to the RNA or DNA or to the chromosomal structure is envisaged as biomedical marker to be tested.

In a further preferred embodiment the mentioned primary subject is a healthy subject. The term "healthy subject" relates to a human being not afflicted by a specific disease in comparison to a second subject, e.g. human being, with regard to the same disease. The term "healthy" thus refers to specific disease situations for which a subject shows no symptoms of disease. The term thus not necessarily means that the person is entirely free of any disease. However, also these persons are envisaged as being healthy for the purpose of the present invention.

In a further preferred embodiment said secondary subject is affected by a medical condition. A medical condition may be any disease or illness known to the person skilled in the art. Such a condition preferably results in the distinguishability of biomedical markers. Preferably the medical condition is cancer. More preferably, the medical condition is an ovarian cancer.

In a further particularly preferred embodiment of the present invention the predictive value which results from the determination of network nodes and/or high ranking network members or combinations thereof is the indication of a likelihood of responsiveness of a subject to a therapy. Such a therapy may be of any type, for instance a chemotherapy, e.g. a chemotherapy against a disease. The term "likelihood of responsiveness" as used herein refers to the probability that a subject may develop a non-responsive state towards the therapy, e.g. develops a resistance against the therapy or the given therapeutic composition. The term "chemotherapy" as used herein means the use of pharmaceutical or chemical substances to a disease, in particular to treat cancer.

In a particularly preferred embodiment the likelihood of responsiveness is a likelihood of responsiveness of a subject to a therapy comprising one or more platinum based drugs. Examples of platinum based drugs are cisplatinum and derivatives or analogs thereof, e.g. oxiplatinum, satraplatinum.

In a particularly preferred embodiment said platinum based drug is carboplatinum. A methodology as described herein above may, hence, be used to identify network elements, e.g. genes and/or genomic loci, which allow an assessment of the likelihood to respond to a platinum based therapy, in particular to a carboplatinum based therapy, e.g. during the treatment of cancer, in particular during the treatment of ovarian cancer.

In another aspect the present invention relates to a biomedical marker or group of biomedical markers associated with the development of a disease, in particular a cancer disease, e.g. ovarian cancer, or associated with a high likelihood of responsiveness of a subject to a cancer therapy. The group of biomedical markers comprises at least 1, 2, 3, 4, 5, 6, 7, 8, 9, 10, 11, 12, 13, 14, 15, 16, 17, 18, 19, 20 or all markers selected from PKMYT1, SKIL, RAB8A, HIRIP3, CTNNB1, NGFR, ZCCHC11, LSP1, CD200, PAX8, CYBRD1, HOXC11, TCEAL1, FZD10, FZD1, BBS4, IRS2, TLX3, TSPAN2, TXN, and CFLAR, as indicated in the following Table 1:

TABLE 1

| Gene Name | Description | SEQ ID NO nucleotide sequence | Genomic DNA Accession No. (with indicated range) |
|---|---|---|---|
| PKMYT1 | Serine threonine kinase | 1 | AC_000148.1 Range: 2995282 . . . 3002378 |
| SKIL | Oncogene; SMAD signaling | 2 | NC_000003.11 Range: 170075472 . . . 170110949 |
| RAB8A | A RAS oncogene; GTP binding; | 3 | NC_000019.9 Range: 16222489 . . . 16244444 |
| HIRIP3 | Histone repressor | 4 | NC_000016.9 Range: 30004315 . . . 30007386 |
| CTNNB1 | WNT Signalling | 5 | NG_013302.1 Range: 5000 . . . 45997 |
| NGFR | P75; cytokine receptor interaction | 6 | NC_000017.10 Range: 47572654 . . . 47592371 |
| ZCCHC11 | Zinc finger | 7 | NC_000001.10 Range: 52888946 . . . 53018742 |
| LSP1 | Lymphocyte specific protein; signal transducer | 8 | NC_000011.9 Range: 1874199 . . . 1913492 |
| CD200 | glycoprotein | 9 | NC_000003.11 Range: 112051915 . . . 112081658 |
| PAX8 | Paired box transcription factor | 10 | NC_000002.11 Range: 113973573 . . . 114036497 |
| CYBRD1 | cytochrome b reductase 1 | 11 | NC_000002.11 Range: 172378865 . . . 172414642 |
| HOXC11 | Homeobox C11 | 12 | NC_000012.11 Range: 4366909 . . . 54370202 |
| TCEAL1 | transcription elongation factor A (SII)-like 1 | 13 | NC_000023.10 Range: 102883647 . . . 102885880 |

TABLE 1-continued

| Gene Name | Description | SEQ ID NO nucleotide sequence | Genomic DNA Accession No. (with indicated range) |
|---|---|---|---|
| FZD10 | frizzled homolog 10 | 14 | NC_000012.11 Range: 130647031 . . . 130650284 |
| FZD1 | frizzled homolog 1 | 15 | NC_000007.13 Range: 90893782 . . . 90898131 |
| BBS4 | Bardet-Biedl syndrome 4 protein | 16 | NG_009416.1 Range: 5000 . . . 57291 |
| IRS2 | insulin receptor substrate 2 | 17 | NG_008154.1 Range: 5000 . . . 37730 |
| TLX3 | T-cell leukemia homeobox 3 | 18 | NC_000005.9 Range: 170736287 . . . 170739137 |
| TSPAN2 | tetraspanin 2 | 19 | NC_000001.10 Range: 115590631 . . . 115632114 |
| TXN | thioredoxin | 20 | NC_000009.11 Range: 113006309 . . . 113018777 |
| CFLAR | CASP8 and FADD-like apoptoswis regulator | 21 | NC_000002.11 Range: 201980815 . . . 202029015 |

In a particularly preferred embodiment of the present invention the mentioned biomedical marker or group of biomedical markers is associated with a high likelihood of responsiveness of a subject to an ovarian cancer therapy. In a further particularly preferred embodiment of the present invention the mentioned biomedical marker or group of biomedical markers is associated with a high likelihood of responsiveness of a subject to an ovarian cancer therapy comprising platinum based drugs. In yet another particularly preferred embodiment of the present invention the mentioned biomedical marker or group of biomedical markers is associated with a high likelihood of responsiveness of a subject to an ovarian cancer therapy comprising carboplatinum.

In a further embodiment of the invention the method of identifying multi-modal associations between biomedical markers as defined herein above may be based on datasets comprising parameters linked to the marker or group of markers defined above, e.g. at least 1, 2, 3, 4, 5, 6, 7, 8, 9, 10, 11, 12, 13, 14, 15, 16, 17, 18, 19, 20 or all markers selected from PKMYT1, SKIL, RAB8A, HIRIP3, CTNNB1, NGFR, ZCCHC11, LSP1, CD200, PAX8, CYBRD1, HOXC11, TCEAL1, FZD10, FZD1, BBS4, IRS2, TLX3, TSPAN2, TXN, and CFLAR, or one or more of the markers or group of markers mentioned in Tables 2, 4 or 5. Preferably, the datasets may comprise data on DNA methylation and/or gene expression.

In a further embodiment the present invention relates to a group of biomedical markers associated with the development of a disease, in particular a cancer disease, e.g. ovarian cancer, or associated with a high likelihood of responsiveness of a subject to a cancer therapy, wherein the group of biomedical markers comprises at least 1, 2, 3, 4, 5, 6, 7, 8, 9, 10, 11, 12, 13, 14, 15, 16, 17, 18, 19, 20 or all markers selected from PKMYT1, SKIL, RAB8A, HIRIP3, CTNNB1, NGFR, ZCCHC11, LSP1, CD200, PAX8, CYBRD1, HOXC11, TCEAL1, FZD10, FZD1, BBS4, IRS2, TLX3, TSPAN2, TXN, and CFLAR, as indicated in Table 1 in combination with at least 1, 2, 3, 4, 5, 6, 7, 8, 9, 10 or more of the markers mentioned in Tables 2, 4 and/or 5. Particularly preferred is a group of markers comprising at least 1, 2, 3, 4, 5, 6, 7, 8, 9, 10, 11, 12, 13, 14, 15, 16, 17, 18, 19, 20 or all markers selected from PKMYT1, SKIL, RAB8A, HIRIP3, CTNNB1, NGFR, ZCCHC11, LSP1, CD200, PAX8, CYBRD1, HOXC11, TCEAL1, FZD10, FZD1, BBS4, IRS2, TLX3, TSPAN2, TXN, and CFLAR and 1, 2, 3, 4, 5, 6, 7, 8, 9, 10 or more of the markers indicated in Table 2. In a further embodiment the group of biomedical markers comprises at least 1, 2, 3, 4, 5, 6, 7, 8, 9, 10, 11, 12, 13, 14, 15, 16, 17, 18, 19, 20 or all markers selected from PKMYT1, SKIL, RAB8A, HIRIP3, CTNNB1, NGFR, ZCCHC11, LSP1, CD200, PAX8, CYBRD1, HOXC11, TCEAL1, FZD10, FZD1, BBS4, IRS2, TLX3, TSPAN2, TXN, and CFLAR and at least one member of one or more of the pathways indicated in Table 2, e.g. Androgen receptor, Pitx2 driven transcription regulation, Wnt signaling pathway, Gata3 and th2 cytokine gene expression, Segmentation clock, PI3K-akt, Leukocyte transendothelial migration and/or Phosphorylation of mek1 by cdk5/p35. Members of the indicated pathway are known to the person skilled in the art, and/or can be derived from qualified textbooks.

The present invention envisages the markers in the form of genetic units, e.g. as genes, or in the form of expressed units, e.g. as transcripts, proteins or derivatives thereof. Furthermore, the marker may comprise secondary binding elements, such as an antibody, a binding ligand, siRNA or antisense RNA molecules specific for the marker transcript. Further included are genomic loci of the mentioned marker, e.g. the genomic DNA indicated in Table 1, or sub-fragments thereof. The marker may also comprise epigenetic modifications within the gene or genomic locus associated with the marker, e.g. methylated forms of the gene or genomic locus, hypomethylated forms of the gene or genomic locus etc.

In one embodiment of the present invention, the group of markers comprises PKMYT1 and SKIL. In a further embodiment of the present invention the group of marker comprises PKMYT1 and RAB8A. In a further embodiment of the present invention the group of marker comprises PKMYT1 and HIRIP3. In yet another embodiment of the present invention the group of marker comprises PKMYT1 and CTNNB1. In yet another embodiment of the present invention the group of marker comprises PKMYT1 and NGFR. In yet another embodiment of the present invention the group of marker comprises PKMYT1 and ZCCHC11. In yet another embodiment of the present invention the group of marker comprises PKMYT1 and LSP1. In yet another embodiment of the present invention the group of marker comprises PKMYT1 and CD200. In yet another embodiment of the present invention the group of marker comprises PKMYT1 and PAX8. In yet another embodiment of the present invention the group of marker comprises PKMYT1 and CYBRD1. In yet another embodiment of the present invention the group of marker comprises PKMYT1 and HOXC11. In yet another embodiment of the present invention the group of marker comprises PKMYT1 and TCEAL1. In yet another embodiment of the present invention the group of marker comprises PKMYT1 and FZD10. In yet another embodiment of the present invention the group of marker comprises PKMYT1 and FZD1. In yet another embodiment of the present invention the group of marker comprises PKMYT1 and BBS4. In yet another embodiment of the present invention the group of marker comprises PKMYT1 and IRS2. In yet another embodiment of the present invention the group of marker comprises PKMYT1 and TLX3. In yet another embodiment of the present invention the group of marker comprises PKMYT1 and TSPAN2. In yet another embodiment of the present invention the group of marker comprises PKMYT1 and TXN. In yet another embodiment of the present invention the group of marker comprises PKMYT1 and CFLAR.

In a further embodiment of the present invention, the group of markers comprises PKMYT1 and SKIL and RAB8A. In a further embodiment of the present invention the group of marker comprises PKMYT1 and SKIL and HIRIP3. In yet another embodiment of the present invention the group of marker comprises PKMYT1 and SKIL and CTNNB1. In yet another embodiment of the present invention the group of marker comprises PKMYT1 and SKIL and NGFR. In yet another embodiment of the present invention the group of marker comprises PKMYT1 and SKIL and ZCCHC11. In yet another embodiment of the present invention the group of marker comprises PKMYT1 and SKIL and LSP1. In yet another embodiment of the present invention the group of marker comprises PKMYT1 and SKIL and CD200. In yet another embodiment of the present invention the group of marker comprises PKMYT1 and SKIL and PAX8. In yet another embodiment of the present invention the group of marker comprises PKMYT1 and SKIL and CYBRD1. In yet another embodiment of the present invention the group of marker comprises PKMYT1 and SKIL and HOXC11. In yet another embodiment of the present invention the group of marker comprises PKMYT1 and SKIL and TCEAL1. In yet another embodiment of the present invention the group of marker comprises PKMYT1 and SKIL and FZD10. In yet another embodiment of the present invention the group of marker comprises PKMYT1 and SKIL and FZD1. In yet another embodiment of the present invention the group of marker comprises PKMYT1 and SKIL and BBS4. In yet another embodiment of the present invention the group of marker comprises PKMYT1 and SKIL and IRS2. In yet another embodiment of the present invention the group of marker comprises PKMYT1 and SKIL and TLX3. In yet another embodiment of the present invention the group of marker comprises PKMYT1 and SKIL and TSPAN2. In yet another embodiment of the present invention the group of marker comprises PKMYT1 and SKIL and TXN. In yet another embodiment of the present invention the group of marker comprises PKMYT1 and SKIL and CFLAR.

In a further embodiment of the present invention, the group of markers comprises PKMYT1 and 2, 3, 4, 5, 6, 7, 8 or more of the markers of Table 1. In a further embodiment of the present invention, the group of markers comprises SKIL and 2, 3, 4, 5, 6, 7, 8 or more of the markers of Table 1.

In yet another embodiment of the present invention, the group of markers comprises at least 1, 2, 3, 4, 5, 6, 7, 8, 9 or all of PKMYT1, SKIL, RAB8A, HIRIP3, CTNNB1, NGFR, ZCCHC11, LSP1, CD200 and PAX8.

In further specific embodiments the present invention relates to groups of markers as indicated in Table 4 and/or 5, e.g. markers which are overrepresentated in gene ontology categories of molecular function and/or biological processes. For instance, the present invention relates to a group of markers indicated in section "ALL" of Table 4 and/or 5. In a further embodiment, the present invention relates to a group of markers indicated in section "CENTRICITY" of Tables 4 and/or Table 5. In a further embodiment, the present invention relates to a group of markers indicated in section "CLOSENESS" of Tables 4 and/or Table 5. In a further embodiment, the present invention relates to a group of markers indicated in section "HIGHCONN" of Tables 4. In a further embodiment, the present invention relates to a group of markers indicated in section "ECCENTRICITY" of Table 5.

In further specific embodiments the present invention relates to groups comprising at least 1, 2, 3, 4, 5, 6, 7, 8, 9 or all markers of PKMYT1, SKIL, RAB8A, HIRIP3, CTNNB1, NGFR, ZCCHC11, LSP1, CD200 and PAX8 of Table 1 and at least 1, 2, 3, 4, 5 or more markers as indicated in Table 2.

In a further aspect the present invention relates to a method of diagnosis in vitro or in vivo of a medical condition, e.g. a cancer disease, preferably ovarian cancer, wherein said method is based on the determination of molecular parameters linked to the marker as defined above, e.g. a marker or group of markers comprising a at least 1, 2, 3, 4, 5, 6, 7, 8, 9, 10, 11, 12, 13, 14, 15, 16, 17, 18, 19, 20 or all markers of Table 1. Preferably, the method of diagnosis comprises the determination of presence or absence or amount/level of an expression product (e.g. protein, transcript etc.) of one or more of the markers. In addition or alternatively, the determination of a secondary parameter such as the methylation status of the marker may be carried out. In a specific embodiment, the marker for which the expression is determined may not be identical to the marker for which a secondary parameter such as the methylation status is determined.

In a further aspect the present invention relates to a composition for in vivo or in vitro diagnosing, detecting, monitoring or prognosticating a disease, preferably a cancer disease, more preferably ovarian cancer, or for diagnosing, detecting, monitoring or prognosticating the likelihood of responsiveness of a subject to a cancer therapy, preferably the therapy against ovarian cancer, more preferably a platinum drug based therapy, even more preferably a carboplatinum based therapy, comprising a nucleic acid affinity ligand and/or a peptide affinity ligand for the expression product(s) or protein(s) of the above mentioned marker or group of markers. Such a composition may alternatively or additionally comprise an antibody against any of the above mentioned markers.

In a preferred embodiment of the present invention said nucleic acid affinity ligand or peptide affinity ligand is modified to function as an imaging contrast agent.

Further envisaged is a method of identifying a subject for eligibility for a cancer disease therapy comprising:

(a) testing in a sample obtained from subject for a parameter associated with a marker or group of markers as indicated herein above;

(b) classifying the levels of tested parameters; and (c) identifying the individual as eligible to receive a cancer disease therapy where the subject's sample is classified as having an increased expression of one or more of the above mentioned markers and/or as having a modified methylation state of one or more of the above mentioned markers.

In another aspect the present invention relates to an assay for detecting, diagnosing, graduating, monitoring or prognosticating a medical condition, preferably cancer, more preferably ovarian cancer, comprising at least the steps of (a) testing in a sample obtained from a subject for the expression of a stratifying biomedical markers or group of said markers and/or of a network node and/or high ranking network member or group of said nodes or members wherein said members can be obtained according to the above described method; alternatively, the testing may be carried out with a marker or group of markers as defined herein above;

(b) testing in a control sample for the expression of the same marker, group of markers, network node, high ranking network member of group thereof as in (a);

(c) determining the difference in expression of markers of steps (a) and (b); and (d) deciding on the presence or stage of medical condition or the responsiveness of a subject to a therapy against said medical condition, based on the results obtained in step (c).

In yet another aspect the present invention relates to an assay for detecting, diagnosing, graduating, monitoring or prognosticating the responsiveness of a subject to a therapy against said medical condition, preferably cancer, more preferably ovarian cancer, even more preferably the responsiveness of a subject to a platinum drug based therapy, e.g. carboplatinum, comprising at least the steps of (a) testing in a sample obtained from a subject for the expression of a stratifying biomedical markers or group of said markers and/or of a network node and/or high ranking network member or group of said nodes or members wherein said members can be obtained according to the above described method; alternatively, the testing may be carried out with a marker or group of markers as defined herein above;

(b) testing in a control sample for the expression of the same marker, group of markers, network node, high ranking network member of group thereof as in (a);

(c) determining the difference in expression of markers of steps (a) and (b); and (d) deciding on the presence or stage of medical condition or the responsiveness of a subject to a therapy against said medical condition, preferably cancer, more preferably ovarian cancer, based on the results obtained in step (c).

In a preferred embodiment of the present invention, the assay as described herein above may comprises the additional step of testing in a sample obtained from a subject for the methylation state and/or pattern of a stratifying biomedical markers or group of said markers and/or of a network node and/or high ranking network member or group of said nodes or members, wherein said members can be obtained according to the above described method; alternatively, the testing may be carried out with a marker or group of markers as defined herein above; wherein in step (c) additionally the difference in methylation status and/or pattern is determined.

Alternatively an assay for detecting, diagnosing, graduating, monitoring or prognosticating a medical condition, preferably cancer, more preferably ovarian cancer as defined herein above, may comprise in step (a) the determination of a different parameter in a sample obtained from a subject. Non limiting examples of such parameters are whole genome sequences, genomic methylation pattern, the identity of methylated sections or elements, the molecular state of a gene or genomic locus, the presence or absence or amount/level of transcripts, proteins, truncated transcripts, truncated proteins, the presence or absence or amount/level of cellular markers, the presence or absence or amount/level of surface markers, the presence or absence or amount/level of glycosylation pattern, the form of said pattern, the presence or absence of expression pattern on mRNA or protein level, the form of said pattern, cell sizes, cell behavior, growth and environmental stimuli responses, motility, the presence or absence or amount/level of histological parameters, staining behavior, the presence or absence or amount/level of biochemical or chemical markers, e.g. peptides, secondary metabolites, small molecules, the presence or absence or amount/level of transcription factors, the form and/or activity of chromosomal regions or loci; and the presence or absence of further biochemical or genetic markers, e.g. the expression or methylation of genes or markers not comprised in Table 1, 2, 4 or 5, or any combination thereof.

Alternatively, an assay for detecting, diagnosing, graduating, monitoring or prognosticating the responsiveness of a subject to a therapy against said medical condition, preferably cancer, more preferably ovarian cancer, even more preferably the responsiveness of a subject to a platinum drug based therapy, e.g. carboplatinum, may comprise in step (a) the determination of a different parameter in a sample obtained from a subject. Non limiting examples of such parameters are whole genome sequences, genomic methylation pattern, the identity of methylated sections or elements, the molecular state of a gene or genomic locus, the presence or absence or amount/level of transcripts, proteins, truncated transcripts, truncated proteins, the presence or absence or amount/level of cellular markers, the presence or absence or amount/level of surface markers, the presence or absence or amount/level of glycosylation pattern, the form of said pattern, the presence or absence of expression pattern on mRNA or protein level, the form of said pattern, cell sizes, cell behavior, growth and environmental stimuli responses, motility, the presence or absence or amount/level of histological parameters, staining behavior, the presence or absence or amount/level of biochemical or chemical markers, e.g. peptides, secondary metabolites, small molecules, the presence or absence or amount/level of transcription factors, the form and/or activity of chromosomal regions or loci; and the presence or absence of further biochemical or genetic markers, e.g. the expression or methylation of genes or markers not comprised in Table 1, 2, 4 or 5, or any combination thereof.

In a further specific embodiment the expression may be tested by any suitable means known to the person skilled in the art, preferably by room temperature polymerase chain reaction (RT-PCR), RNA sequencing, or gene expression detection on microarrays.

In yet another specific embodiment the methylation state or methylation pattern may be determined by using methylation specific PCR (MSP), bisulfite sequencing, the employment of microarray techniques, direct sequencing, such as, for example, implemented by Pacific Biosciences®.

In yet another aspect the invention relates to a method for classifying a subject comprising:

(a) providing a subject's dataset comprising data on methylated loci and data on gene expression of a stratifying biomedical marker or group of said markers and/or of a network node and/or high ranking network member or group of said nodes or members wherein said members can be obtained according to the above described method; alternatively, the dataset may be based on a marker or group of markers as defined herein above;

(b) accessing a database comprising database values for a stratifying biomedical marker or group of said markers and/or of a network node and/or high ranking network member or group of said nodes or members wherein said members can be obtained according to the above described method; alternatively, the database may be accessed for a marker or group of markers as defined herein above;

(c) calculating a subject's classification score based on the difference between database between the results of step (a) and (b).

In a preferred embodiment the dataset to be provided from a subject may comprise data on methylated loci linked to the marker or group of markers defined above, e.g. at least 1, 2, 3, 4, 5, 6, 7, 8, 9, 10, 11, 12, 13, 14, 15, 16, 17, 18, 19, 20 or all markers selected from PKMYT1, SKIL, RAB8A, HIRIP3, CTNNB1, NGFR, ZCCHC11, LSP1, CD200, PAX8, CYBRD1, HOXC11, TCEAL1, FZD10, FZD1, BBS4, IRS2, TLX3, TSPAN2, TXN, and CFLAR, or the markers or group of markers mentioned in Table 2, 4 or 5.

In a further specific embodiment of the present invention preferred methylated loci linked to the marker or group of markers of the present invention, or being located in the vicinity of the marker or group of markers of the present invention, in particular the markers of Table 1, or loci linked to or being located in the vicinity of said markers which are preferably consulted, analysed (e.g. via methylation detection means as defined herein) or tested in order to obtain datasets from a subject, are indicated in the following table which provides genomic coordinates linked to the markers comprised in Table 1:

| Chromosome | Start | End | Closest Gene |
|---|---|---|---|
| 1 | 52730331 | 52730552 | ZCCHC11 |
| 1 | 52730611 | 52730733 | ZCCHC11 |
| 1 | 52730734 | 52730888 | ZCCHC11 |
| 1 | 52731025 | 52731215 | ZCCHC11 |
| 1 | 52731315 | 52731455 | ZCCHC11 |
| 1 | 52731456 | 52732425 | ZCCHC11 |
| 1 | 115343699 | 115343965 | TSPAN2 |
| 1 | 115344225 | 115344328 | TSPAN2 |
| 1 | 115344465 | 115344664 | TSPAN2 |
| 2 | 113750708 | 113750905 | PAX8 |
| 2 | 113751138 | 113751290 | PAX8 |
| 2 | 113751695 | 113751825 | PAX8 |
| 2 | 113751826 | 113751957 | PAX8 |
| 2 | 113751981 | 113752204 | PAX8 |
| 2 | 201808587 | 201808903 | CFLAR |
| 2 | 172204489 | 172204729 | CYBRD1 |
| 2 | 172204730 | 172204867 | CYBRD1 |
| 2 | 172204868 | 172204983 | CYBRD1 |
| 2 | 172205161 | 172205286 | CYBRD1 |
| 2 | 172205287 | 172205410 | CYBRD1 |
| 2 | 172205411 | 172205550 | CYBRD1 |
| 2 | 201806500 | 201806648 | CFLAR |
| 2 | 201806881 | 201806995 | CFLAR |
| 2 | 201807105 | 201808144 | CFLAR |
| 3 | 41213549 | 41215233 | CTNNB1 |
| 3 | 41215292 | 41215399 | CTNNB1 |
| 3 | 41215404 | 41215527 | CTNNB1 |
| 3 | 41215828 | 41215935 | CTNNB1 |
| 3 | 41216038 | 41216194 | CTNNB1 |
| 3 | 113534054 | 113534772 | CD200 |
| 3 | 113534878 | 113535030 | CD200 |
| 3 | 171557568 | 171557718 | SKIL |
| 3 | 171557857 | 171557961 | SKIL |
| 3 | 171558082 | 171558200 | SKIL |
| 3 | 171558263 | 171558378 | SKIL |
| 3 | 171558697 | 171558855 | SKIL |
| 5 | 170666547 | 170667821 | TLX3 |
| 5 | 170667889 | 170668074 | TLX3 |
| 5 | 170668379 | 170668538 | TLX3 |
| 5 | 170668544 | 170668736 | TLX3 |
| 5 | 170668737 | 170668894 | TLX3 |
| 5 | 170668895 | 170669053 | TLX3 |
| 5 | 170669129 | 170669238 | TLX3 |
| 5 | 170669265 | 170669473 | TLX3 |
| 5 | 170669618 | 170669721 | TLX3 |
| 5 | 170669860 | 170669985 | TLX3 |
| 5 | 170670020 | 170670447 | TLX3 |
| 5 | 170670448 | 170670599 | TLX3 |
| 7 | 90537970 | 90538274 | FZD1 |
| 7 | 90538398 | 90538569 | FZD1 |
| 7 | 90539178 | 90539501 | FZD1 |
| 7 | 90539515 | 90539633 | FZD1 |
| 7 | 90539644 | 90539897 | FZD1 |
| 7 | 90539959 | 90540209 | FZD1 |
| 7 | 90540210 | 90540369 | FZD1 |
| 7 | 90540370 | 90540529 | FZD1 |
| 9 | 110096997 | 110097425 | TXN |
| 9 | 110097512 | 110097666 | TXN |
| 9 | 110097667 | 110097868 | TXN |
| 9 | 110097934 | 110098215 | TXN |
| 11 | 1848448 | 1848761 | LSP1 |
| 11 | 1848762 | 1849063 | LSP1 |
| 11 | 1849064 | 1849183 | LSP1 |
| 12 | 52652610 | 52653249 | HOXC11 |
| 12 | 52653275 | 52653497 | HOXC11 |
| 12 | 52653596 | 52653696 | HOXC11 |
| 12 | 52653697 | 52653807 | HOXC11 |
| 12 | 52653990 | 52654219 | HOXC11 |
| 12 | 52654220 | 52654341 | HOXC11 |
| 12 | 52654342 | 52654469 | HOXC11 |
| 12 | 52654470 | 52654651 | HOXC11 |
| 12 | 52654768 | 52655073 | HOXC11 |
| 12 | 52655173 | 52655281 | HOXC11 |
| 12 | 129169880 | 129170207 | FZD10 |
| 12 | 129170283 | 129170392 | FZD10 |
| 12 | 129170525 | 129170816 | FZD10 |
| 12 | 129170909 | 129171018 | FZD10 |
| 12 | 129171257 | 129171376 | FZD10 |
| 12 | 129171377 | 129171494 | FZD10 |
| 12 | 129171997 | 129172097 | FZD10 |
| 12 | 129172453 | 129172685 | FZD10 |
| 12 | 129173006 | 129173124 | FZD10 |
| 12 | 129173728 | 129173996 | FZD10 |
| 13 | 109234815 | 109234915 | IRS2 |
| 13 | 109235600 | 109235866 | IRS2 |
| 13 | 109235951 | 109236241 | IRS2 |
| 13 | 109236242 | 109236365 | IRS2 |
| 13 | 109236896 | 109237128 | IRS2 |
| 13 | 109237235 | 109237354 | IRS2 |
| 13 | 109237454 | 109237562 | IRS2 |
| 13 | 109237563 | 109237850 | IRS2 |
| 13 | 109237890 | 109238485 | IRS2 |
| 15 | 70765350 | 70765593 | BBS4 |
| 15 | 70765674 | 70765798 | BBS4 |
| 16 | 2969849 | 2969984 | PKMYT1 |
| 16 | 2970065 | 2970187 | PKMYT1 |
| 16 | 2970188 | 2970331 | PKMYT1 |
| 16 | 2970620 | 2970773 | PKMYT1 |
| 16 | 2970867 | 2971519 | PKMYT1 |
| 16 | 29913959 | 29914151 | HIRIP3 |
| 16 | 29914157 | 29914370 | HIRIP3 |
| 16 | 29914439 | 29914684 | HIRIP3 |
| 16 | 29914685 | 29914964 | HIRIP3 |
| 17 | 44927437 | 44927578 | NGFR |
| 17 | 44927579 | 44927679 | NGFR |
| 17 | 44927680 | 44927795 | NGFR |
| 17 | 44928073 | 44928180 | NGFR |
| 17 | 44928181 | 44928315 | NGFR |
| 17 | 44928392 | 44928662 | NGFR |
| 19 | 16083047 | 16083266 | RAB8A |
| 19 | 16083371 | 16083493 | RAB8A |
| 19 | 16083525 | 16083845 | RAB8A |
| 19 | 16083874 | 16084520 | RAB8A |
| 23 | 102690660 | 102690795 | TCEAL1 |
| 11 | 1831415 | 1831798 | LSP1 |

In a particularly preferred embodiment the above indicated genomic regions, or sections comprising said regions, e.g. sections differing by about 10 nt to about 5 kb from the indicated regions, may be analysed for the presence of methylated nucleotides, the presence or absence of methylation pattern etc. These may preferably be correlated with corresponding expression data of one or more of the markers or group of markers indicated in Table 1. These regions may be analysed separately, or in combination, e.g. for each marker all indicated regions or a sub-set thereof may be analysed. Furthermore, any combination of regions for more than one marker may be analysed.

Alternatively, the dataset may comprise data on further parameters linked to the marker or group of markers defined above, e.g. at least 1, 2, 3, 4, 5, 6, 7, 8, 9, 10, 11, 12, 13, 14, 15, 16, 17, 18, 19, 20 or all markers selected from PKMYT1, SKIL, RAB8A, HIRIP3, CTNNB1, NGFR, ZCCHC11, LSP1, CD200, PAX8, CYBRD1, HOXC11, TCEAL1, FZD10, FZD1, BBS4, IRS2, TLX3, TSPAN2, TXN, and CFLAR, or the markers or group of markers mentioned in Table 2, 4 or 5. Non limiting examples of such parameters are whole genome sequences, genomic methylation pattern, the identity of methylated sections or elements, the molecular state of a gene or genomic locus, the presence or absence or amount/level of transcripts, proteins, truncated transcripts, truncated proteins, the presence or absence or amount/level of cellular markers, the presence or absence or amount/level of surface markers, the presence or absence or amount/level of glycosylation pattern, the form of said pattern, the presence or absence of expression pattern on mRNA or protein level, the form of said pattern, cell sizes, cell behavior, growth and environmental stimuli responses, motility, the presence or absence or amount/level of histological parameters, staining behavior, the presence or absence or amount/level of biochemical or chemical markers, e.g. peptides, secondary metabolites, small molecules, the presence or absence or amount/level of transcription factors, the form and/or activity of chromosomal regions or loci; and the presence or absence of further biochemical or genetic markers, e.g. the expression or methylation of genes or markers not comprised in Table 1, 2, 4 or 5, or any combination thereof.

In consequence, the method also may include a step of accessing a database comprising database values for the marker or group of markers defined above, e.g. at least 1, 2, 3, 4, 5, 6, 7, 8, 9, 10, 11, 12, 13, 14, 15, 16, 17, 18, 19, 20 or all markers selected from PKMYT1, SKIL, RAB8A, HIRIP3, CTNNB1, NGFR, ZCCHC11, LSP1, CD200, PAX8, CYBRD1, HOXC11, TCEAL1, FZD10, FZD1, BBS4, IRS2, TLX3, TSPAN2, TXN, and CFLAR, or the markers or group of markers mentioned in Table 4 or 5. Furthermore, the method may alternatively include a step of accessing a database comprising database values with regard to further parameters linked to the marker or group of markers defined above, e.g. at least 1, 2, 3, 4, 5, 6, 7, 8, 9, 10, 11, 12, 13, 14, 15, 16, 17, 18, 19, 20 or all markers selected from PKMYT1, SKIL, RAB8A, HIRIP3, CTNNB1, NGFR, ZCCHC11, LSP1, CD200, PAX8, CYBRD1, HOXC11, TCEAL1, FZD10, FZD1, BBS4, IRS2, TLX3, TSPAN2, TXN, and CFLAR, or the markers or group of markers mentioned in Table 4 or 5. Non limiting examples of such parameters are whole genome sequences, genomic methylation pattern, the identity of methylated sections or elements, the molecular state of a gene or genomic locus, the presence or absence or amount/level of transcripts, proteins, truncated transcripts, truncated proteins, the presence or absence or amount/level of cellular markers, the presence or absence or amount/level of surface markers, the presence or absence or amount/level of glycosylation pattern, the form of said pattern, the presence or absence of expression pattern on mRNA or protein level, the form of said pattern, cell sizes, cell behavior, growth and environmental stimuli responses, motility, the presence or absence or amount/level of histological parameters, staining behavior, the presence or absence or amount/level of biochemical or chemical markers, e.g. peptides, secondary metabolites, small molecules, the presence or absence or amount/level of transcription factors, the form and/or activity of chromosomal regions or loci; and the presence or absence of further biochemical or genetic markers, e.g. the expression or methylation of genes or markers not comprised in Table 1, 2, 4 or 5, or any combination thereof.

In yet another aspect the present invention relates to a medical decision support system comprising:

an input for providing a subject dataset comprising data on methylated loci and data on gene expression of a stratifying biomedical marker or group of said markers and/or of a network node and/or high ranking network member or group of said nodes, wherein said members can be obtained according to the above described method; alternatively, the dataset may be based on a marker or group of markers as defined herein above;

a computer program product for enabling a processor to carry out the method for classifying a subject as defined above, and an output for outputting the subject classification score.

In a preferred embodiment the dataset to be used as input may comprise data on methylated loci linked to or derived from the marker or group of markers defined above, e.g. at least 1, 2, 3, 4, 5, 6, 7, 8, 9, 10, 11, 12, 13, 14, 15, 16, 17, 18, 19, 20 or all markers selected from PKMYT1, SKIL, RAB8A, HIRIP3, CTNNB1, NGFR, ZCCHC11, LSP1, CD200, PAX8, CYBRD1, HOXC11, TCEAL1, FZD10, FZD1, BBS4, IRS2, TLX3, TSPAN2, TXN, and CFLAR, or the markers or group of markers mentioned in Table 4 or 5. E.g. a subject to be tested may specifically be tested for one or more of the mentioned markers, or the group of markers as defined above.

In a specific embodiment said medical decision support system may be a molecular oncology decision making workstation. The decision making workstation may preferably be used for deciding on the initiation and/or continuation of a cancer therapy for a subject. More preferably, the decision making workstation may be used for deciding on the probability and likelihood of responsiveness to a platinum based therapy.

In a further aspect the present invention also envisages a software or computer program to be used on a decision making workstation. The software may, for example, be based on the analysis of datasets or data linked to the marker or group of markers defined above, e.g. at least 1, 2, 3, 4, 5, 6, 7, 8, 9, 10, 11, 12, 13, 14, 15, 16, 17, 18, 19, 20 or all markers selected from PKMYT1, SKIL, RAB8A, HIRIP3, CTNNB1, NGFR, ZCCHC11, LSP1, CD200, PAX8, CYBRD1, HOXC11, TCEAL1, FZD10, FZD1, BBS4, IRS2, TLX3, TSPAN2, TXN, and CFLAR, or the markers or group of markers mentioned in Table 2, 4 or 5.

The following examples and figures are provided for illustrative purposes. It is thus understood that the example and figures are not to be construed as limiting. The skilled person in the art will clearly be able to envisage further modifications of the principles laid out herein.

EXAMPLES

Example 1—General Methodology

Initially, genome-wide DNA methylation data of ovarian cancer patients was obtained. Methylation Oligonucleotide Microarray Analysis (MOMA) was used to perform genome-wide scans of CpG island methylation in normal and tumor samples according to Kamalakaran et al., Nucleic Acids Res (12): e89, 2009, which is incorporated herein in its entirety.

Patient samples were categorized in two groups: platinum-resistant patients have PFI (platinum free interval) of <6 months (12 patients) and platinum-sensitive patients have PFI>24 months (13 patients).

Methylation probes were filtered based on the size of target fragments and intensity to retain ~190,000 probes out of the original 330,000 probes in MOMA covering 27,000 CpG islands in the human genome.

Linear models with Bayesian statistics and leave-one-out cross-validation were used to find statistically significant and robust stratifying probes/loci. A list of 749 candidate loci that stratify resistant and sensitive patients could be derived, which served as input to further pathway and network analysis. FIG. 1 summarizes the steps of the procedure.

The genes in the proximity of the candidate loci were used to identify the most significant pathways using the pathway analysis tool in GeneSpring GX11. The tool takes a list of entities (e.g. gene symbols) as an input and finds all pathways from a collection which have significant overlap with that entity list. The set of pathways used in this analysis was imported from the BioPAx, KEGG repositories (www.biopax.org; www.genome.jp/kegg/pathway.htm). Here, overlap denotes the number of common entities between the list and the pathway. Commonness is determined via the presence of a shared identifier, i.e., Entrez Gene ID. Once the number of common entities is determined, the p-value computation for a pathway is based on the Hypergeometric method (or Fisher's exact test).

Separately, as input gene expression profiles of the genes proximal to the stratifying methylation probes using Affymetrix (HGU133a) were taken. Based on the two distinct measurements, a weighted methylation-expression matrix was constructed. Methylation profiles of the unique stratifying genes were correlated to the expression profiles. The methylation-expression similarity $s_{ij}$ between genes i and j are defined as the absolute value of the correlation coefficient between their expression and methylation profiles according to the formula:

$$s(i,j)=|cor(x_i,x_j)|$$

To obtain a threshold value to select the significant correlations, the methylation profiles were permuted 100 times and 100 methylation-expression correlation matrices were constructed.

Based on the distribution of all correlation values, a hard threshold value of 0.58 ($99^{th}$ percentile) was used to identify the most highly correlated and anti-correlated connections. There were multiple probes (among the 749) representing the same gene and some probes were not present in the Affymetrix data. Ultimately, there were 263 unique genes used in the correlation matrix.

Subsequently a network graph was constructed with genes as nodes and the presence of an edge for all i and j where $s_{ij}>0.58$ was defined. A directed edge between i and j indicates the correlation of the methylation profile of i to expression of j (not expression to methylation). Network centrality measure of node betweenness was used to identify key genes. Nodes that occur on many shortest paths between other nodes have higher betweenness than those that do not. High betweenness of a node indicates that a gene has high influence over the information flow between other genes in the network. Other network metrics computed include: connectivity (number of genes adjacent to a gene) and eccentricity (accessibility of a gene by all other genes in the network).

The network graph based on the correlation matrix was analyzed in Pajek (further details are described in Nooy et al., Exploratory Social Network Analysis with Pajek, Cambridge University Press, 2005, which is incorporated herein in its entirety), a network analysis and visualization software.

Example 2—Assessment of Overrepresentation of Biological Processes

Based on a network as described in Example 1, it is also possible to assess overrepresentation of biological processes or molecular functions in a selected network subset. By selecting a sub network of interconnected genes that are connected and known to be highly ranked by one of the network metrics, it is possible to determine the overrepresentation of categories given by Gene Ontology. The steps taken to characterize the enrichment of these sub-networks involve:

Importing the network into Cytoscape (further details are described in Shannon et al., Cytoscape: a software environment for integrated models of biomolecular interactionnetworks, Genome Research, 2003, 13(11): 2498-2504, which is incorporated herein in its entirety);

Importing the network metrics as attributes of the nodes;

Selecting a subset of nodes (e.g. top ranked nodes) and edges (e.g. most correlated and anti-correlated nodes here the threshold value is 0.55)

Invoke the BingGO plug-in for Cytoscape (further details are described in Maere et al., BINGO: a Cytoscape plugin to assess overrepresentation of Gene Ontology categories in biological networks, Bioinformatics, 2006, 21, 3448, which is incorporated herein in its entirety);

Set the parameters for BinGO;
Select ontology: Mo lecular Function/Bio logical Process;
Select annotation (organism): Homo sapiens;
Select statistical test: Hypergeometric test;
Select correction: Benjamin & Hochberg False Discovery Rate (FDR) correction;
Select significance level: 0.05;
Testing option: Test cluster versus whole annotation; and
Execute overrepresentation analysis.

Example 3—Pathways in Carboplatinum Sensitivity

The linear model analysis as described in Example 1 identified a set of 749 probes that differentiates between resistance and sensitivity to platinum based drugs in ovarian cancer. These were subjected to pathway analysis using GeneSpring. Pathways showing significant overlap with genes (entities) in the gene list (entity list) selected for analysis are displayed in Table 2.

TABLE 2

List of enriched pathways and genes

| Pathways | P-value |
|---|---|
| Androgen receptor | 0.0016 |
| Pitx2 driven transcription regulation | 0.0042 |
| Wnt signaling pathway | 0.0135 |
| Gata3 and th2 cytokine gene expression | 0.0270 |
| Segmentation clock | 0.0297 |
| PI3K-akt | 0.0343 |
| Leukocyte transendothelial migration | 0.0441 |
| Phosphorylation of mek1 by cdk5/p35 | 0.0441 |

| Gene: | Function: | Sequence Identifier: |
|---|---|---|
| GSK3B | glycogen synthase kinase 3 beta | (SEQ ID NO: 22) |
| FZD1 | frizzled homolog 1 | (SEQ ID NO: 15) |
| CTNNB1 | WNT Signalling | (SEQ ID NO: 5) |
| COX5B | cytochrome c oxidase subunit Vb | (SEQ ID NO: 23) |
| PXN | paxilin | (SEQ ID NO: 24) |
| POU2F1 | POU class 2 homeobox 1 | (SEQ ID NO: 25) |

TABLE 2-continued

| | | |
|---|---|---|
| CCNE1 | Cyclin E1 | (SEQ ID NO: 26) |
| TMF1 | TATA element modulatory factor 1 | (SEQ ID NO: 27) |
| MAPK1 | mitogen-activated protein kinase 1 | (SEQ ID NO: 28) |
| PTEN | phosphatase and tensin homolog | (SEQ ID NO: 29) |
| NCOA3 | nuclear receptor coactivator 3 | (SEQ ID NO: 30) |
| GATA3 | GATA binding protein 3 | (SEQ ID NO: 31) |
| NFATC1 | nuclear factor of activated T-cells | (SEQ ID NO: 32) |
| PTX2 | paired-like homeodomain 2 | (SEQ ID NO: 33) |
| CCND2 | cyclin D2 | (SEQ ID NO: 34) |

The table also highlights the genes among the pathways important in chemosensitivity to platinum. Contributions from AR pathway, Wnt pathway and PI3K-akt pathway have been well-characterized in ovarian cancer. Methylated PITX2 has been shown to predict outcome in lymph node-negative breast cancer patients.

Figure 2:
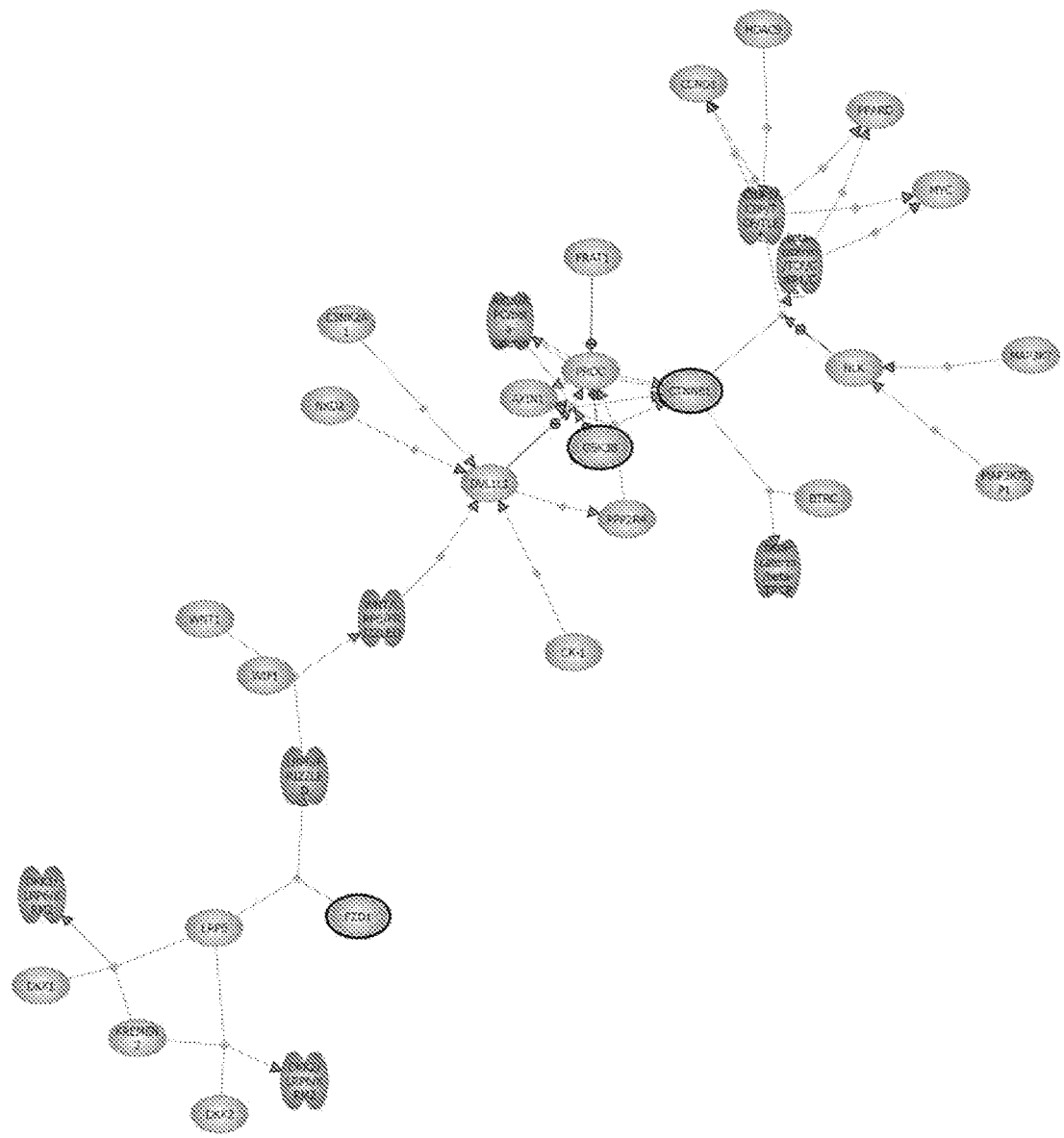
FIG. 2 depicts the Wnt pathway and members of it that are stratifying genes (halos), in particular FZD1, GSK3B and CTNNB1.

In FIG. 2 one of the significant pathways—the Wnt pathway is shown in more detail with the members overlapping with the established list of genes, identified in blue halo: FZD1, GSK3B and CTNNB1. Methylation of another frizzle protein SFRP has been shown to promote ovarian cancer progression and chemoresistance. Suppression of CTNNB1 has also been evident in many cancers.

An analysis of how genes in a list are connected to each other in a target-regulator relationship based on biologically known interactions can also be revealing. Since this exercise is not focused on one particular pathway it can allow investigating the crosstalk between nodes of different pathways.

Figure 3:
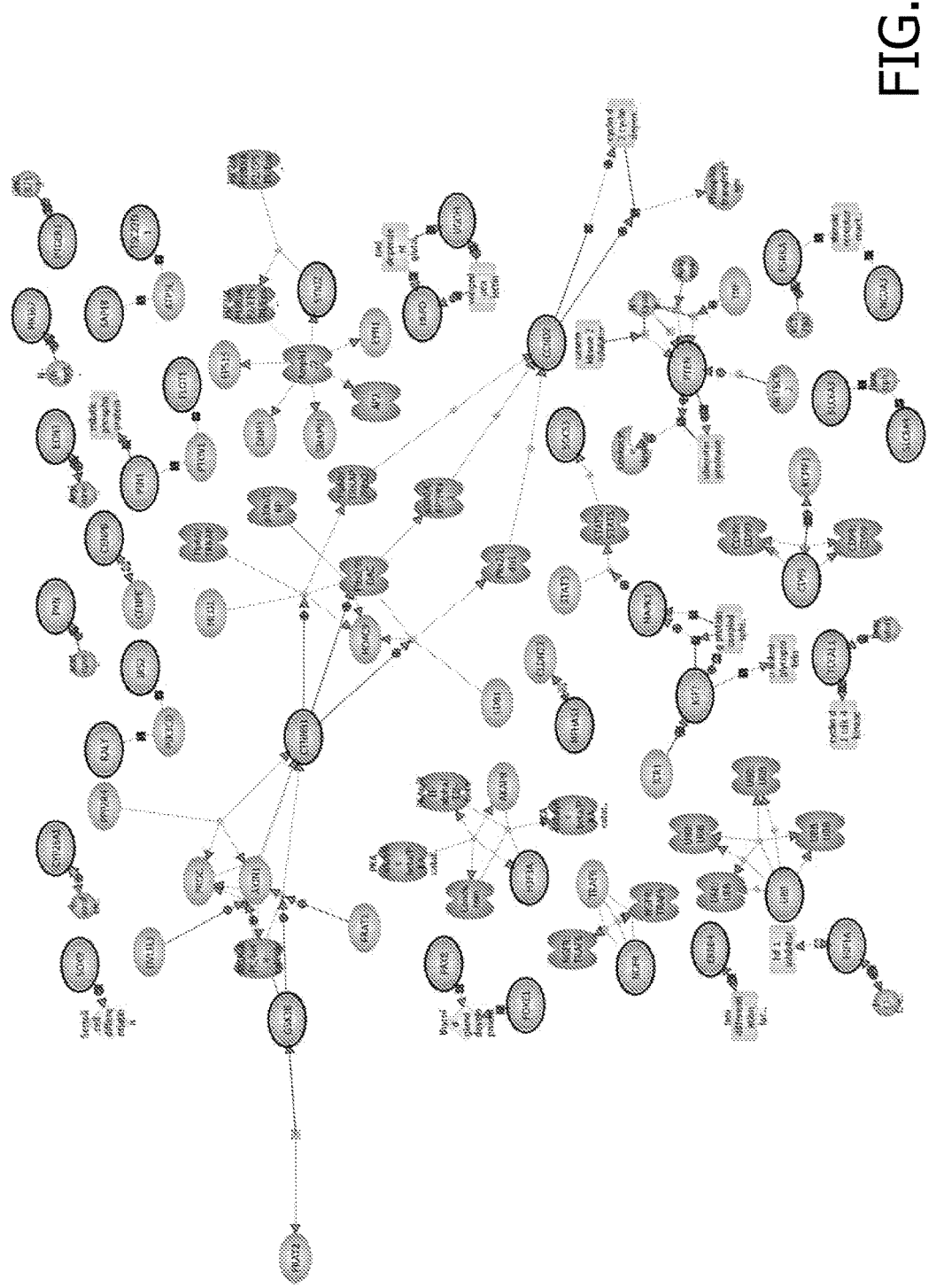
FIG. 3 shows a target-regulator network. The figure shows nodes, which are included if they have at least one known interaction from biological databases with the identified stratifying genes. Further indicated are CTNNB1 and CCND as hubs which are involved mainly in Wnt signaling. Further indicated is PTEN from the p53 signaling pathway.

In FIG. 3, the target-regulator network based on the established list generated by GeneSpring is shown. Nodes are included in this graph if they have at least one known interaction from biological databases with a gene in our list. The hubs CTNNB1, CCND2 appear to be involved mainly in Wnt signaling pathway. PTEN from p53 signaling pathway is also represented but most interactions appear to have one or two links.

Example 4—Network Structure Analysis

A weighted methylation-expression network was constructed as described above. The network centrality measure of betweenness was calculated by noting the shortest paths between all pairs of nodes (see FIG. 4). A large node in this graph corresponds to a gene that is frequently found in shortest paths between gene pairs giving it a high betweenness measure. Edges e(i,j) represent correlation (solid edges) or anti-correlation (dashed edges) between methylation profile of gene i and expression profile of gene j. Table 2 provides, inter alia, information on betweenness, eccentricity and connectivity for the central nodes in FIG. 4.

A majority of these nodes are involved in cancer-related functions or signaling pathways. Some of the central nodes include PKMYT1, CTNNB1, RAB8A and NGFR. NGFR has low connectivity but ranks higher in betweenness and eccentricity measures because it is traversed in the shortest paths of many pairs of genes. NGFR is known to act via cytokine receptor interactions and is often used as a marker (along with CA125 and p55) for ovarian cancer. Recently, expression of NGFR has also been used as a marker to measure toxicity to carboplatin. It was not identified as an enriched pathway in the GeneSpring analysis most likely because enough members of this pathway were not represented in the list or the pathway databases were incomplete. It is also possible that incorporating expression information solidified its correlation characteristics with other genes.

TABLE 3

Identified central nodes: Annotation of central nodes with their corresponding network measure values: betweenness BTW ($\sigma$ = 2.8e−5; $\rho$ = 0.00013), eccentricity ECC ($\sigma$ = 0.59 [−1.72, 1.72]; $\rho$ = 1.5), and connectivity CON ($\sigma$ = 1.07; $\rho$ = 1.8)

| Node (Gene Name) | Description | SEQ ID NO nucleotide sequence | BTW | ECC | CON |
|---|---|---|---|---|---|
| PKMYT1 | Serine threonine kinase | 1 | 0.00088 | 1.48 | 7 |
| SKIL | Oncogene; SMAD signaling | 2 | 0.000877 | 1.71 | 4 |
| RAB8A | A RAS oncogene; GTP binding; | 3 | 0.000866 | 1.48 | 18 |
| HIRIP3 | Histone repressor | 4 | 0.000859 | 1.42 | 5 |
| CTNNB1 | WNT Signalling | 5 | 0.000712 | 1.66 | 3 |
| NGFR | P75; cytokine receptor interaction | 6 | 0.000661 | 1.52 | 2 |
| ZCCHC11 | Zinc finger | 7 | 0.000570 | 1.50 | 4 |
| LSP1 | Lymphocyte specific protein; signal transducer | 8 | 0.00035 | 1.63 | 5 |
| CD200 | glycoprotein | 9 | 0.0002 | 1.68 | 3 |
| PAX8 | Paired box transcription factor | 10 | 0.00019 | 1.62 | 2 |

Figure 4:
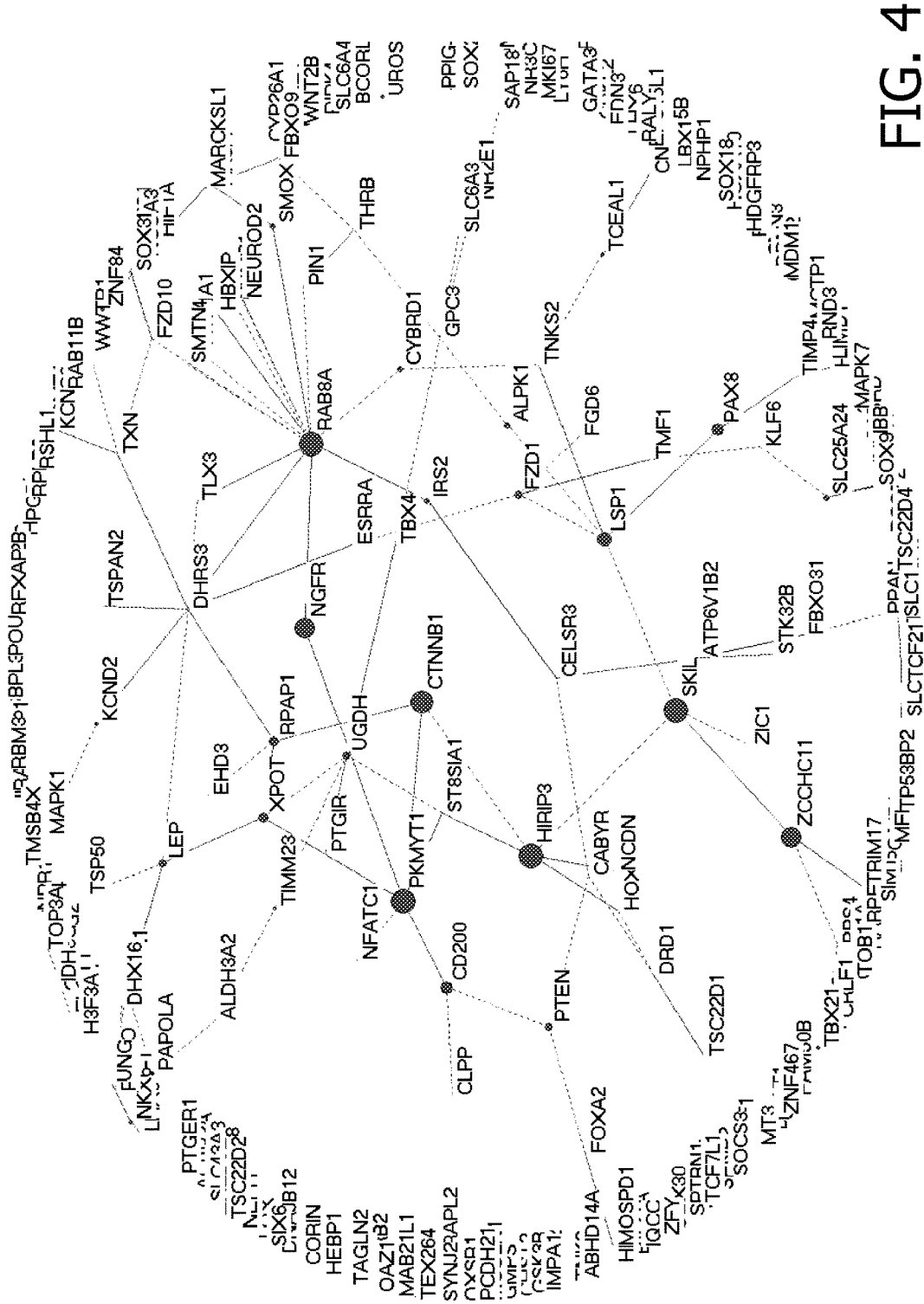
FIG. 4 depicts a methylation-expression correlation sub-network showing the nodes (red) that measure high in betweenness centrality measure.

As can be derived from FIG. 4, RAB8A, a member of the RAS oncogene family, is highly connected. Over-expression of another member of this family, RAB25, has been associated with increased proliferation and aggressiveness in breast and ovarian cancer. Although RAB8A was not identified in the GeneSpring approach, network measures and related literature search suggest that it is likely to have an important role. A directed edge between RAB8A and NGFR implies that the methylation profile of RAB8A and the expression profile of NGFR are highly correlated.

By using the methylation-expression correlation matrix in this analysis, we were able to identify multi-modal associations that are of importance in chemosensitivity. For example, a patient can be predicted sensitive to chemotherapy based on methylated RAB8A and under expressed NGFR. So, the combined analysis based on two data types in some sense reorders the larger list of stratifying genes by incorporation of methylation and expression data with network topological measures.

Example 5—Analysis of Overrepresentation of Gene Ontology Categories

Analysis of overrepresentation of gene ontology categories in the correlation sub-networks (interconnected genes that are connected and known to be highly ranked by one of the network metrics) identified relevant biological processes or molecular functions. Tables 4 and 5, below, represent the results of this analysis:

| GO-ID | p-value | corr p-value | x | n | X | N | Description | Genes in test set |
|---|---|---|---|---|---|---|---|---|
| 30528 | 2.3170E-9 | 9.8007E-7 | 45 | 1473 | 182 | 15247 | transcription regulation activity | CDX2\|E2F5\|FOXA2\|THRB\|TBX21\| SOX3\|NR3C2\|CTCF\|SOX9\|ZIC1\| RFXAP\|NR2E1\|TCEAL1\|TCF7L1\| TMF1\|CTNNB1\|TSC22D1\|CCNE1\| TCF21\|PCGF2\|TSC22D2\|TSC22D4\| PAX8\|JUND\|LHX3\|SOX18\|LHX6\| SKIL\|TLX3\|NFATC1\|KLF6\|ESRRA\| ZFY\|TBX4\|SAP18\|WWTR1\|GTF2B\| SIX6\|NKX61\|HOXC11\|HIF1A\| NCOA3\|SALL1\|NEUROD2\|TOB1 |
| 3700 | 4.3036E-8 | 9.1020E-6 | 34 | 1023 | 182 | 15247 | transcription factor binding | CDX2\|FOXA2\|THRB\|E2F5\|TBX21\| SOX3\|NR3C2\|CTCF\|ZIC1\|RFXAP\| NR2E1\|TCEAL1\|TCF7L1\|CTNNB1\| TSC22D1\|TCF21\|PCGF2\|TSC22D2\| TSC22D4\|PAX8\|LHX3\|JUND\|SOX18\| LHX6\|TLX3\|NFATC1\|ESRRA\|TBX4\| SIX6\|NKX61\|HOXC11\|HIF1A\| SALL1\|NEUROD2 |
| 3677 | 6.5749E-5 | 9.2706E-3 | 47 | 2255 | 182 | 15247 | DNA binding | ZNF84\|CDX2\|E2F5\|ZNF467\|FOXA2\| THRB\|TBX21\|SOX3\|NR3C2\|CTCF\| ZIC1\|SOX9\|RFXAP\|NR2E1\|TCEAL1\| TCF7L1\|DPF1\|TMF1\|CTNNB1\| TSC22D1\|TCF21\|PCGF2\|TSC22D2\| TSC22D4\|CENPB\|PAX8\|LHX3\| JUND\|NEFH\|SOX18\|LHX6\|SKIL\| TLX3\|NFATC1\|HEMK1\|KLF6\|RAB8A\| ESRRA\|ZFY\|TBX4\|SIX6\|NKX61\| HOXC11\|HIF1A\|SALL1\| NEUROD2\|H3F3A |
| 8134 | 2.4290E-4 | 2.1440E-2 | 14 | 389 | 182 | 15247 | transcription factor binding | THRB\|TP53BP2\|SAP18\|CTCF\| HDAC11\|WWTR1\|RFXAP\|CTNNB1\| TMF1\|SENP2\|CCNE1\|NCOA3\|SKIL\| TOB1 |
| 4926 | 2.5726E-4 | 2.1440E-2 | 3 | 11 | 182 | 15247 | non-G-protien coupled 7TM receptor activity | FZD8\|FZD10\|FZD1 |
| 3702 | 3.0411E-4 | 2.1440E-2 | 11 | 261 | 182 | 15247 | RNA polymerase II transcription factor activity | TCF21\|HOXC11\|HIF1A\|JUND\|LHX3\| SOX18\|CTCF\|SOX9\|TCEAL1\|GTF2B\| TMF1 |
| 5488 | 4.9415E-4 | 2.9861E-2 | 153 | 11217 | 182 | 15247 | binding | KIFC1\|AOF2\|CDX2\|THRB\|SLC6A3\| PGD\|PKMYT1\|DNAJB12\|ZIC1\|RFXAP\| COX5B\|NR2E1\|TCEAL1\|CTNNB1\| CDH22\|IDH3G\|SLC25A24\|MCOLN1\| LOX\|IDUA\|SNRPA1\|ALDH6A1\|IRS2\| KCND2\|BAIAP3\|HDAC11\|HBXIP\| SIX6\|BCAP31\|SSTR4\|RND3\|MAPK1\| SPAG7\|AQR\|HIF1A\|MAPK7\|TRAF1\| COASY\|BBS4\|DRD1\|ERBB4\| PCDH21\|SOX3\|OAS3\|ATP6VIB2\| SOX9\|PXN\|PIN1\|KCNS3\|TCF21\| CRMP1\|JUND\|LHX3\|LHX6\|SKIL\| FGD6\|GABRD\|XPOT\|GABARAPL2\| CFLAR\|KLF6\|RAB8A\|ESRRA\| MKI67\|TP53BP2\|SAP18\|CELSR3\| OXSR1\|NKX61\|RPS7\|SALL1\| SLC25A10\|FBXO31\|H3F3A\| TNK2\|BMP7\|ZNF84\|IMPA1\| E2F5\|FOXA2\|CLDN3\|MARCKSL1\| TBX21\|CTCF\|AMN\|PTEN\|TMF1\| GPC4\|CCNE1\|PCGF2\|GPC3\| PAX8\|SYNJ2\|SOX18\|ATP5O\|MT3\| HEMK1\|PTGER1\|ZCCHC11\|ZFY\| FLOT1\|PRKCI\|TIMM23\|GTF2B\| MCTP1\|INHBB\|SENP2\|DHRS3\| DOK2\|SMTN\|HOXC11\|NCOA3\|RIF1\| CCND2\|TXN\|NGFR\|CNN3\| ZNF467\|TRIM17\|UNG\|CRLF1\| NR3C2\|TCF7L1\|DPF1\|HDGFRP3\| CDH8\|TSC22D1\|STK32B\|TSC22D2\| TSC22D4\|CENPB\|NEFH\| DHX16\|TLX3\|EHD3\|NFATC1\|FZD8\| ALPK1\|DGKQ\|TBX4\|FZD1\| ATP1A1\|RACGAP1\|WWTR1\|CABYR\| WNT2B\|LEP\|LSP1\|PAPOLA\| ARSA\|NEUROD2\|RBM16\|TOB1 |

-continued

CENTRICITY

File created with BiNGO (c)
ontology: function
curator: GO
Selected ontology file: jar:file:C:\Program Files\Cytoscape_v2.7.0\plugins\GOlorize2-4.jar!/GO_Molecular_Function
Selected annotation file: jar:file:C:\Program File\Cytoscape_v2.7.0\plugins\GOlorize2-4.jar!/H_sapiens_default
Discarded evidence codes:
Overrepresentation
Selected statistical test: Hypergeometric test
Selected correction: Benjamini & Hochberg False Discovery Rate (FDR) correction
Selected significance level: 0.05
Testing option: Test cluster versus whole annotation
The selected cluster:
GPC4 BBS4 RAB8A HOXC11 ZCCHC11 NCDN CYBRD1 HIRIP3TCEAL1
No annotations were retrieved for the following entities:
NCDN HIRIP3

| GO-ID | p-value | corr p-value | x | n | X | N | Description | Genes in test set |
|---|---|---|---|---|---|---|---|---|
| 293 | 1.3762E-3 | 2.8437E-2 | 1 | 3 | 7 | 15253 | ferric-chelate reductase activity | CYBRD1 |
| 16723 | 1.8346E-3 | 2.8437E-2 | 1 | 4 | 7 | 15253 | oxidoreductase activity, oxidizing metal ions, NAD or NADP as acceptor | CYBRD1 |
| 16722 | 3.2087E-3 | 3.3157E-2 | 1 | 7 | 7 | 15253 | oxidoreductase activity, oxidizing metal ions | CYBRD1 |
| 3702 | 5.7876E-3 | 4.4854E-2 | 2 | 261 | 7 | 15253 | RNA polymerase II transcription factor activity | HOXC11|TCEAL1 |

CLOSENESS

File created with BiNGO (c)
ontology: function
curator: GO
Selected ontology file: jar:file:C:\Program Files\Cytoscape_v2.7.0\plugins\GOlorize2-4.jar!/GO_Molecular_Function
Selected annotation file: jar:file:C:\Program Files\Cytoscape_v2.7.0\plugins\GOlorize2-4.jar!/H_sapiens_dafault
Discarded evidence codes:
Overrepresention
Selected statistical test: Hypergeometric test
Selected correction: Benjamini & Hochberg False Discovery Rate (FDR) correction
Selected significance level: 0.05
Testing option: Test cluster versus whole annotation
The selected cluster:
TRAF1 TSPAN2 ST8SIA1 PKMYT1 CTNNB1 PIN1 JUND SMOX HIRIP3TLX3 XPOT SNRPA1 ESRRA IRS2 RAB8A KCND2 FZD1 TNKS2LSP1 LEP FZD20 RPAP1 DHRS3TXN CYBRD1 NGFR
No annotations were retrieved for the following entities:
RPAP1 TSPAN2 HIRIP3

| GO-ID | p-value | corr p-value | x | n | X | N | Description | Genes in test set |
|---|---|---|---|---|---|---|---|---|
| 4926 | 1.1867E-4 | 1.22342E-2 | 2 | 11 | 23 | 15251 | non-G-protien cupled 7TM receptor activity | FZD10|FZD1 |

HIGHCONN

File created with BiNGO (c)
ontology: function
curator: GO
Selected ontology file: jar:file:C:\Program Files\Cytoscape_v2.7.0\plugins\GOlorize2-4.jar!/GO_Molecular_Function
Selected annotation file: jar:file:C:\Program File\Cytoscape_v2.7.0\plugins\GOlorize2-4.jar!/H_sapiens_default
Discarded evidence codes:
Overrepresentation
Selected statistical test: Hypergeometric test
Selected correction: Benjamini & Hochberg False Discovery Rate (FDR) correction
Selected significance level: 0.05
Testing option: Test cluster versus whole annotation
The selected cluster:
CCBL1 DRD1 THRB UGDH OAS3 ST8SIA1 PKMYT1 ATP6V1B2 PTEN CTNNB1 GPC3 SLC25A24 DHX16 HIRIP3 SKIL XPOT RABSA ZCCHCH11FZD1 CELSR3 WWTR1 CABYR TNKS2 LSP1 LEP DHRS3 F2D10 RPAP1 NCOA3 TXN CD200
No annotations were retrieved for the following entities:
RPAP1 HIRIP3 CD200

-continued

| GO-ID | p-value | corr p-value | x | n | X | N | Description | Genes in test set |
|---|---|---|---|---|---|---|---|---|
| 4926 | 1.7694E-4 | 1.5129E-2 | 2 | 11 | 28 | 15252 | non-G-protien coupled 7TM receptor activity | FZD10\|FZD1 |
| 3712 | 1.9907E-4 | 1.5129E-2 | 5 | 302 | 28 | 15252 | transcriptiom cofactor activity | NCOA3\|THRB\|SKIL\|WWTR1\| |
| 8134 | 6.3700E-4 | 2.1465E-2 | 5 | 389 | 28 | 15252 | transcription factor binding | CTNNB1 |
| 50681 | 7.3390E-4 | 2.1465E-2 | 2 | 22 | 28 | 15252 | androgen receptor binding | NCOA3\|THRB\|SKIL\|WWTR11 |
| 3714 | 1.1334E-3 | 2.1465E-2 | 3 | 113 | 28 | 15252 | transcription corepressor activity | CTNNB1 |
| 35258 | 1.2797E-3 | 2.1465E-2 | 2 | 29 | 28 | 15252 | steroid hormone receptor binding | NCOA3\|CTNNB1 |
| 47316 | 1.8358E-3 | 2.1465E-2 | 1 | 1 | 28 | 15252 | glutamine-phenylpyruvate transaminase activity | THRB\|SKIL\|WWTR1 |
| 51717 | 1.8358E-3 | 2.1465E-2 | 1 | 1 | 28 | 15252 | inositol-1,3,4,5-tetrakisphosphate 3-phosphatase activity | NCOA3\|CTNNB1 CCBL1 |
| 1590 | 1.8358E-3 | 2.1465E-2 | 1 | 1 | 28 | 15252 | dopamine D1 receptor activity | PTEN |
| 1588 | 1.8358E-3 | 2.1465E-2 | 1 | 1 | 28 | 15252 | dopamine D1 receptor-like receptor activity | DRD1 |
| 51800 | 1.8358E-3 | 2.1465E-2 | 1 | 1 | 28 | 15252 | phosphatidylinositol-3,4-bi-phosphate 3-phosphatase activity | DRD1 PTEN |
| 47804 | 1.8358E-3 | 2.1465E-2 | 1 | 1 | 28 | 15252 | cycteine-S-conjugate beta-lyase activity | CCBL1 |
| 3979 | 1.8358E-3 | 2.1465E-2 | 1 | 1 | 28 | 15252 | UDP-glucose 6-dehydrogenase activity | UGDH |
| 35257 | 3.6236E-3 | 3.1838E-2 | 2 | 49 | 28 | 15252 | nulear hormone receptor binding | NCOA3\|CTNNB1 |
| 16314 | 3.6684E-3 | 3.1838E-2 | 1 | 2 | 28 | 15252 | phosphatidylinositol-3,4,5-tri-phosphate 3-phosphatase activity | PTEN |
| 45294 | 3.6684E-3 | 3.1838E-2 | 1 | 2 | 28 | 15252 | alpha-catenin binding | CTNNB1 |
| 16212 | 3.6684E-3 | 3.1838E-2 | 1 | 2 | 28 | 15252 | kynurenine-oxoglutarate transaminase activity | CCBL1 |
| 51427 | 3.7703E-3 | 3.1838E-2 | 2 | 50 | 28 | 15252 | hormone receptor binding | NCOA3\|CTNNB1 |
| 3713 | 4.1315E-3 | 3.3052E-2 | 3 | 178 | 28 | 15252 | transcription coactivator activity | NCOA3\|WWTR1\|CTNNB1 |
| 9055 | 5.1776E-3 | 3.9349E-2 | 3 | 193 | 28 | 15252 | electron carrier activity | DHRS3\|TXN\|UGDH |
| 4438 | 5.4977E-3 | 3.9793E-2 | 1 | 3 | 28 | 15252 | phosphatidylinositol-3-phosphatase activity | PTEN |
| 16564 | 6.1199E-3 | 4.2283E-2 | 3 | 205 | 28 | 15252 | transcriptional repressor activity | THRB\|SKIL\|WWTR1 |

TABLE 5

Cytoscape Bingo results on biological processes

ALL
File created with BiNGO (c)
ontology: process
curator: GO
Selected ontology file: jar:file:C:\Program Files\Cytoscape_v2.7.0\plugins\GOlorize2-4.jar!/GO_Biological_Process
Selected annotation file: jar:file:C:\Program Files\Cytoscape_v2.7.0\plugins\GOlorize2-4.jar!/H_sapiens_default
Discarded evidence codes:
Overrepresentation
Selected statistical test: Hypergeometric test
Seleceted correction: Benjamini & Hochberg False Discovery Rate (FDR) correction
Selected significance level: 0.05
Testing option: Test cluster versus whole annotation
The selected cluster:
KIFC RARRES2AOF2 CDX2 PGD DNAJB12 RFXAP CTNNB1 CDR22 SMOX SGPL1 SSTR4 RND3 MAPK1 AQR SPAG7 RSHL1 MAPK7 COASY ERBB4
PCDH21 OAS3 PXN PIN1 TCF21 PPAN CRMP1 LHX3 DULLARD LHX6 FBXO9 KLF6 ESRRA MKI67 TP53BP2 CELSR3 OXSRI NKX6-1
RPS7 DUSP26 CNIH3 H3F3A TNK2 BMP7 CD200 ENY2 FOXA2 MARCKSL1 TBX21 PTEN CKB CCNE1 SYNJ2 ATPSO ZCCHC11 FLOT1
GTF2B INHBR SENP2 DOK2 H6PD CCND2 TXN CYBRD1 MOSPD1 ZNF467 TRIM17 UNG UGDH UROS HDGFRP3 DHX16 TLX3 FZD8
DGKQ TBX4 FZD1 ATP1A1 WWTR1 CABYR LSP1 PAPOLA LARGE NEUROD2 ARSA SLC15A3 RBM16 TOB1 TSPAN2 THRB SLC6A3
PKMYT1 ZIC1 TCEAL1 NR2E1 COX5B PTGIR IDH3G SLC25A24 MCOLN1 HIRIP3 LOX FBXO22 IDUA SNRPA1 ALDH6A1 IRS2 KCND2
BAIAP3 HDAC11 HBNIP SIX6 BCAP31 TNKS2 HIF1A CLPP TRAF1 BBS4 CCBL1 DRD1 SOX3 ST8S1A1 TIMP4 ATP6V1B2 SOX9 KCNS3
OAZ1 JUND SKIL FGD6 GABRD XPOT GABARAPL2 CFLAR RAB8A SAP18 SLC25A10 SALL1 TSP50 FBXO31 ZNF84 IMPA1 E2F5
CLDNG CTCF AMN TMF1 GPC4 PCGF2 GPC3 PAX8 SOX18 MT3 SLC43A3 HEMK1 PTGER1 ZFy PRKCI CHST2 DDN TIMM23 MCTP1
DHRS3 ADFP SMTIN DGAT1 HOXC11 RIFI NCOA3 NGFR UBB CNN3 CRLF1 NR3C2 TCF7L1 ALDH3A2 DPF1 CDH8 TSC22D1 STK32B TABLE 5-continued Cytoscape Bingo results on biological processes TSC22D2 TSC22D4 CENPS NEFH ETNK2 HS6ST1 EHD3 NFATC1 ALPK1 NCDN RAGAP1 WNT2B LEP FZD10 RPAP1
No annotations were retrieved for the following entities:
FNY2 ZCCHC11NCDN MARCKSL1 FLOT1 DDN CKB RPAP1 ADFP SPAG7 RSHL1 DULLARD SYNJ2 MOSPD1 CD200
EHD3 RBM16
SLC43A3

| GO-ID | p-value | corr p-value | x | n | X | N | Description | Genes in test set |
|---|---|---|---|---|---|---|---|---|
| 9887 | 1.0309E-8 | 1.0186E-5 | 24 | 473 | 177 | 13949 | organ morphogenesis | CDX2\|E2F5\|ERBB4\|FOXA2\|THRB\|SOX3\|TBX4\|SOX9\| ZIC1\|SIX6\|PTEN\|NKX61\|WNT2B\|CTNNB1\|INHBB\| MAPK1\|TCF21\|DGAT1\|GPC3\|HID1A\|PAX8\|LHX3\| BMP7\|NFATC1 |
| 48856 | 2.3545E-8 | 1.1631E-5 | 52 | 1885 | 177 | 13949 | anatomical structure development | CDX2\|THRB\|FOXA2\|E2F5\|TBX21\|PGD\|ZIC1\|PTEN\| NR2E1\|CTNNB1\|GPC4\|GPC3\|PAX8\|MT3\|IRS2\| PRKCI\|SIX6\|INHBB\|MAPK1\|HIF1A\|SMTN\|DGAT1\| HOXC11\|NGFR\|BBS4\|DRD1\|ERBB4\|SOX3\|SOX9\| TCF7L1\|ALDH3A2\|TCF21\|CRMP1\|LHX3\|NEFH\| LHX6\|TLX3\|FGD6\|NFATC1\|KLF6\|TBX4\|FZD1\| RACGAP1\|WWTRA\|NKX61\|WNT2B\|LEP\|LARGE\| SALL1\|NEUROD2\|BMP7\|TOB1 |
| 48513 | 3.8852E-8 | 1.2795E-5 | 35 | 1009 | 177 | 13949 | organ development | CDX2\|E2F5\|FOXA2\|ERBB4\|THRB\|TBX21\|SOX3\|PGD\| SOX9\|ZIC1\|PTEN\|CTNNB1\|TCF21\|GPC3\|PAX8\| LHX3\|LHX6\|NFATC1\|KLF6\|IRS2\|TBX4\|WWTR1\| SIX6\|KNX61\|WNT2B\|LEP\|INHBB\|MAPK1\|DGAT1\| SMTN\|HIF1A\|LARGE\|SALL1\|BMP7\|TOB1 |
| 7275 | 5.2332E-8 | 1.2926E-5 | 60 | 2404 | 177 | 13949 | development | CDX2\|FOXA2\|THRB\|E2F5\|TBX21\|PGD\|ZIC1\|AMN\| PTEN\|NR2E1\|CTNNB1\|GPC4\|GPC3\|PAX8\|MT3\| IRS2\|PRCI\|CHST2\|SIX6\|INHBB\|MAPK1\|HOXC11\| DGAT1\|HIF1A\|SMTN\|NGFR\|BBS4\|DRD1\|ERBB4\| SOX3\|UGDH\|SOX9\|ALDH3A2\|TCF7L1\|TCF21\| CRMP1\|LHX3\|NEFH\|LHX6\|SKIL\|TLX3\|FGD6\| NFATC1\|FZD8\|KLF6\|TBX4\|FZD1\|CELSR3\| RACGAP1\|WWTR1\|NKX61\|WNT2B\|LEP\|FZD10\| LARGE\|SALL1\|NEUROD2\|FBXO31\|BMP7\|TOB1 |
| 9653 | 3.8119E-7 | 7.5322E-5 | 33 | 1007 | 177 | 13949 | morphogenesis | BBS4\|CDX2\|FOXA2\|ERBB4\|THRB\|E2F5\|SOX3\|ZIC1\| SOX9\|PTEN\|CTNNB1\|GPC4\|TCF21\|GPC3\|PAX8\| LHX3\|FGD6\|NFATC1\|MT3\|KLF6\|TBX4\|PRKCI\|FZD1\| SIX6\|NKX61\|WNT2B\|INHBB\|MAPK1\|DGAT1\|HIF1A\| SALL1\|NGFR\|BMP7 |
| 48731 | 2.5263E-6 | 4.1600E-4 | 25 | 698 | 177 | 13949 | system development | BBS4\|DRD1\|ERBB4\|SOX3\|PGD\|ZIC1\|NR2E1\|PTEN\| ALDH3A2\|CTNNB\|GPC3\|CRMP1\|PAX8\|NEFH\|LHX6\| TLX3\|MT3\|IRS2\|RACGAP1\|NKX61\|LARGE\|SALL1\| NEUROD2\|NGFR\|BMP7 |
| 51244 | 4.6156E-6 | 6.5146E-4 | 73 | 3597 | 177 | 13949 | regulation of cellular physiological process | ZNF84\|AOF2\|CDX2\|E2F5\|FOXA2\|THRB\|TBX21\| SLC6A3\|PKMYT1\|CTCF\|PTEN\|TCEAL1\|NR2E1\| TMF1\|CTNNB1\|CCNE1\|PCGF2\|GPC3\|PAX8\|SOX18\| MT3\|IRS2\|ZFY\|HDAC11\|HBXIP\|GTF2B\|SIX6\| SENP2\|INHBB\|SSTR4\|MARK1\|HOXC11\|HIF1A\| NCOA3\|CCND2\|NGFR\|TRAF1\|BBS4\|ZNF467\| SOX3\|NR3C2\|ST8SIA1\|SOX9\|TCF7L1\|DPF1\| PIN1\|TSC22D1\|TCF21\|TSC22D2\|TSC22D4\|CENPB\| LHX3\|JUND\|DHX16\|LHX6\|TLX3\|NFATC1\|KLF6\| CFLAR\|ESRRA\|RAB8A\|MKI67\|TP53BP2\|TBX4\| SAP18\|WWTR1\|NKX61\|SALL1\|NEUROD2\|FBXO31\| TNK2\|BMP7\|TOB1 |
| 50794 | 1.3986E-5 | 1.7272E-3 | 76 | 3913 | 177 | 13949 | regulation of cellular process | ZNF84\|AOF2\|CDX2\|E2F5\|FOXA2\|THRB\|TBX21\| SLC6A3\|PKMYT1\|CTCF\|ZIC1\|PTEN\|TCEAL1\| NR2E1\|TMF1\|CTNNB1\|CCNE1\|PCGF2\|GPC3\|PAX8\| SOX18\|MT3\|IRS2\|ZFY\|HDAC11\|HBXIP\|GTF2B\| SIX6\|SENP2\|INHBB\|SSTR4\|MAPK1\|HOXC11\| HIF1A\|NCOA3\|CCND2\|NGFR\|TRAF1\|BBS4\|ZNF467\| SOX3\|NR3C2\|ST8SIA1\|SOX9\|TCF7L1\|DPF1\|PIN1\| TSC22D1\|TCF21\|TSC22D2\|TSC22D4\|CENPB\|LHX3\| JUND\|DHX16\|LHX6\|TLX3\|FGD6\|NFATC1\|CFLAR\| KLF6\|RAB8A\|ESRRA\|MKI67\|TP53BP2\|TBX4\| SAP18\|WWTR1\|NKX6-1\|LEP\|SALL1\|NEUROD2\| FBXO31\|TNK2\|BMP7\|TOB1 |
| 50791 | 17.191E-5 | 1.8872E-3 | 74 | 3794 | 177 | 13949 | regulation of physiological process | ZNF84\|AOF2\|CDX2\|E2F5\|FOXA2\|THRB\|TBX21\| SLC6A3\|PKMYT1\|CTCF\|PTEN\|TCEAL1\|NR2E1\| TMF1\|CTNNB1\|CCNE1\|PCGF2\|GPC3\|PAX8\|SOX18\| MT3\|IRS2\|ZFY\|HDAC11\|HBXIP\|GTF2B\|SIX6\| SENP2\|INHBB\|SSTR4\|MAPK1\|HOXC11\|HIF1A\| NCOA3\|CCND2\|NGFR\|TRAF1\|BBS4\|ZNF467\|SOX3\| NR3C2\|ST8SIA1\|SOX9\|TCF7L1\|DPF1\|PIN1\| TSC22D1\|TCF21\|TSC22D2\|TSC22D4\|CENPB\|LHX3\| JUND\|DHX16\|LHX6\|TLX3\|NFATC1\|KLF6\|CFLAR\| |

TABLE 5-continued

Cytoscape Bingo results on biological processes

| | | | | | | | | |
|---|---|---|---|---|---|---|---|---|
| 8151 | 2.5839E−5 | 2.5529E−3 | 157 | 10668 | 177 | 13949 | cellular physiological process | ESRRA\|RAB8A\|MKI67\|TP53BP2\|TBX4\|SAP18\|WWTR1\|NKX6-1\|LEP\|SALL1\|NEUROD2\|FBXO31\|TNK2\|BMP7\|TOB1 KIFC1\|AOF2\|RARRES2\|CDX2\|TSPAN2\|THRB\|SLC6A3\|PGD\|PKMYT1\|DNAJB12\|RFXAP\|TCEAL1\|NR2E1\|COX5B\|CTNNB1\|IDH3G\|SLC25A24\|SMOX\|MCOLN1\|HIRIP3\|LOX\|FBXO22\|IDUA\|SGPL1\|SNRPA1\|ALDH6A1\|IRS2\|KCND2\|BAIAP3\|HDAC11\|HBXIP\|SIX6\|BCAP31\|TNKS2\|SSTR4\|MAPK1\|RND3\|AQR\|HIF1A\|CLPP\|MAPK7\|TRAF1\|COASY\|BBS4\|CCBL1\|DRD1\|ERBB4\|SOX3\|ST8SIA1\|OAS3\|ATP6V1BZ\|SOX9\|PXN\|PIN1\|KCNS3\|TCF21\|PPAN\|OAZ1\|CRMP1\|JUND\|LHX3\|LHX6\|SKIL\|FGD6\|FBXO9\|XPOT\|GABRD\|CFLAR\|GABARAPL2\|KLF6\|RAB8A\|ESRRA\|MKI67\|TP53BP2\|SAP18\|OXSR1\|NKX61\|RPS7\|DUSP26\|SALL1\|SLC25A10\|TSP50\|FBXO31\|H3F3A\|TNK2\|BMP7\|ZNF84\|IMPA1\|E2F5\|FOXA2\|TBX21\|CTCF\|AMN\|PTEN\|TMF1\|GPC4\|CCNE1\|PCGF2\|GPC3\|PAX8\|SOX18\|ATP5O\|HEMK1\|MT3\|PTGER1\|ZFY\|CHST2\|PRKCI\|TIMM23\|GTF2B\|SENP2\|INHBB\|DHRS3\|HOXC11\|DGAT1\|NCOA3\|RIF1\|CCND2\|H6PD\|TXN\|CYBRD1\|UBB\|NGFR\|CNN3\|ZNF467\|UNG\|NR3C2\|UGDH\|UROS\|ALDH3A2\|TCF7L1\|DPF1\|HDGFRP3\|TSC22D1\|811628\|TSC22D2\|TSC22D4\|CENPB\|NEFH\|DHX16\|HS6ST1\|TLX3\|NFATC1\|ALPK1\|TBX4\|ATP1A1\|RACGAP1\|WWTR1\|WNT2B\|LEP\|LSP1\|PAPOLA\|LARGE\|NEUROD2\|ARSA\|SLC15A3\|TOB1 |
| 44237 | 3.2608E−5 | 2.9288E−3 | 123 | 7615 | 177 | 13949 | cellular metabolism | AOF2\|RARRES2\|CDX2\|THRB\|SLC6A3\|PGD\|PKMYT1\|DNAJB12\|RFXAP\|TCEAL1\|NR2E1\|COX5B\|CTNNB1\|IDH3G\|SMOX\|HIRIP3\|LOX\|FBXO22\|IDUA\|SGPL1\|SNRPA1\|ALDH6A1\|IRS2\|HDAC11\|SIX6\|TNKS2\|MAPK1\|AQR\|HIF1A\|CLPP\|MAPK7\|COASY\|CCBL1\|ERBB4\|SOX3\|OAS3\|ST8SIA1\|ATP6V1B2\|SOX9\|PIN1\|TCF21\|PPAN\|OAZ1\|CRMP1\|LHX3\|JUND\|LHX6\|SKIL\|FBXO9\|KLF6\|CFLAR\|ESRRA\|RAB8A\|SAP18\|OXSR1\|NKX61\|RPS7\|DUSP26\|SLC25A10\|SALL1\|TSP50\|H3F3A\|FBXO31\|TNK2\|BMP7\|ZNF84\|IMPA1\|FOXA2\|E2F5\|TBX21\|CTCF\|PTEN\|TMF1\|CCNE1\|PCGF2\|PAX8\|ATP5O\|SOX18\|HEMK1\|MT3\|PTGER1\|ZFY\|CHST2\|PRKCI\|GTF2B\|SENP2\|INHBB\|DHRS3\|HOXC11\|DGAT1\|NCOA3\|H6PD\|TXN\|CYBRD1\|UBB\|ZNF467\|UNG\|NR3C2\|UROS\|UGDH\|ALDH3A2\|TCF7L1\|DPF1\|TSC22D1\|STK32B\|TSC22D2\|TSC22D4\|CENPB\|NEFH\|DHX16\|HS6ST1\|TLX3\|NFATC1\|ALPK1\|TBX4\|RACGAP1\|WWTR1\|WNT2B\|LEP\|PAPOLA\|LARGE\|NEUROD2\|ARSA |
| 6350 | 3.3853E−5 | 2.9729E−3 | 53 | 2461 | 177 | 13949 | transcription | ZNF84\|AOF2\|CDX2\|THRB\|FOXA2\|E2F5\|TBX21\|CTCF\|NR2E1\|TCEAL1\|RFXAP\|CTNNB1\|TMF1\|CCNE1\|PCGF2\|PAX8\|SOX18\|ZFY\|HDAC11\|GTF2B\|SIX6\|SENP2\|HIF1A\|HOXC11\|NCOA3\|ZNF467\|SOX3\|NR3C2\|SOX9\|TCF7L1\|DPF1\|TSC22D1\|TCF21\|TSC22D2\|TSC22D4\|CENPB\|LHX3\|JUND\|LHX6\|SKIL\|TLX3\|NFATC1\|KLF6\|ESRRA\|RAB8A\|TBX4\|SAP18\|WWTR1\|NKX6-1\|PAPOLA\|SALL1\|NEUROD2\|BMP7 |
| 48522 | 3.9117E−5 | 2.9729E−3 | 25 | 819 | 177 | 13949 | positive regulation of cellular process | BBS4\|FOXA2\|ST8SIA1\|CTCF\|SOX9\|PTEN\|TCF7L1\|CTNNB1\|DPF1\|CCNE1\|GPC3\|PAX8\|CFLAR\|IRS2\|TP53BP2\|WWTR1\|NKX61\|INHBB\|LEP\|MAPK1\|HIF1A\|NCOA3\|TNK2\|NGFR\|BMP7 |
| 7399 | 4.3379E−5 | 3.0613E−3 | 22 | 673 | 177 | 13949 | nervous system development | BBS4\|DRD1\|IRS2\|ERBB4\|SOX3\|PGD\|RACGAP1\|ZIC1\|PTEN\|NR2E1\|ALDH3A2\|NKX61\|CTNNB1\|LARGE\|CRMP1\|NEUROD2\|NEFH\|LHX6\|NGFR\|BMP7\|TLX3\|MT3 |
| 6139 | 4.9987E−5 | 3.2544E−3 | 70 | 3626 | 177 | 13949 | nucleabase, nucleoside, nucleotide and nucleic acid metabolism | ZNF84\|AOF2\|CDX2\|E2F5\|FOXA2\|THRB\|TBX21\|PGD\|CTCF\|RFXAP\|TCEAL1\|NR2E1\|TMF1\|CTNNB1\|CCNE1\|PCGF2\|PAX8\|SOX18\|ATP5O\|HIRIP3\|HEMK1\|SNRPA1\|ALDH6A1\|ZFY\|HDAC11\|GTF2B\|SIX6\|SENP2\|HOXC11\|AQR\|HIF1A\|NCOA3\|H6PD\|ZNF467\|UNG\|SOX3\|NR3C2\|OAS3\|UGDH\|ATP6V1B2\|SOX9\|TCF7L1\|DPF1\|TSC22D1\|TCF21\|PPAN\|TSC22D2\|TSC22D4\|CRMP1\|CENPB\|LHX3\|JUND\|NEFH\|DHX16\|LHX6\|SKIL\|TLX3\|NFATC1\|KLF6\|ESRRA\|RAB8A\|TBX4\|SAP18\|WWTR1\|NKX61\|PAPOLA\|SALL1\|NEUROD2\|H3F3A\|BMP7 |

TABLE 5-continued

Cytoscape Bingo results on biological processes

| | | | | | | | |
|---|---|---|---|---|---|---|---|
| 30154 | 5.5429E-5 | 3.2544E-3 | 27 | 942 | 177 | 13949 | cell differentiation |

BBS4|CDX2|FOXA2|ERBB4|SOX3|ZIC1|SOX9|
CTNNB1|PAX8|SKIL|TLX3|MT3|NFATC1|KLF6|
FZD1|RACGAP1|WWTR1|NKX61|LEP|INHBB|
HIF1A|SALL1|NEUROD2|FBXO31|NGFR|BMP7|
TOB1

| | | | | | | | |
|---|---|---|---|---|---|---|---|
| 50789 | 5.5996E-5 | 3.2544E-3 | 79 | 4275 | 177 | 13949 | regulation of biological process |

ZNF84|AOF2|CDX2|E2F5|FOXA2|THRB|TBX21|
SLC6A3|PKMYT1|CTCF|ZIC1|PTEN|TCEAL1|
NR2E1|TMF1|CTNNB1|CCNE1|PCGF2|GPC3|
PAX8|SOX18|HEMK1|MT3|IRS2|ZFY|HDAC11|
HBXIP|GTF2B|SIX6|SENP2|INHBB|SSTR4|MAPK1|
HOXC11|HIF1A|NCOA3|CCCND2|NGFR|TRAF1|
BBS4|DRD1|ZNF467|SOX3|NR3C2|ST8SIA1|
SOX9|TCF7L1|DPF1|PIN1|TSC22D1|TCF21|
TSC22D2|TSC22D4|CENPB|JUND|LHX3|DHX16|
LHX6|TLX3|FGD6|NFATC1|CFLAR|KLF6|RAB8A|
ESRRA|DGKQ|MKI67|TP53BP2|TBX4|SAP18|
WWTR1|NKX61|LEP|SALL1|NEUROD2|FBXO31|
TNK2|BMP7|TOB1

| | | | | | | | |
|---|---|---|---|---|---|---|---|
| 44238 | 8.9336E-5 | 4.2648E-3 | 119 | 7413 | 177 | 13949 | primary metabolism |

AOF2|RARRES2|CDX2|THRB|SLC6A3|PGD|
PKMYT1|DNAJBI2|RFXAP|TCEAL1|NR2E1|
CTNNB1|IDH3G|SMOX|HIRIP3|LOX|FBXO22|
IDUA|SGPL1|SNRPA1|ALDH6A1|IRS2|HDAC11|
SIX6|TNKS2|MAPK1|AQR|HIF1A|CLPP|MAPK7|
TRAF1|BBS4|CCBL1|ERBB4|SOX3|OAS3|
ST8SIA1|ATP6V182|SOX9|PIN1|TCF21|PPAN|
OAZ1|CRMP1|LHX3|JUND|LHX6|SKIL|FBXO9|
KLF6|CFLAR|ESRRA|RAB8A|SAP18|OXSR1|
NKX61|RPS7|DUSP26|SLC25A10|SALL1|
TSP50|H3F3A|FBXO31|TNK2|BMP7|ZNF84|
IMPA1|FOXA2|E2F5|TBX21|CTCF|PTEN|TMF1|
CCNE1|PCGF2|PAX8|ATP5O|SOX18|HEMK1|
PTGER1|ZFY|CHST2|PRKCI|GTF2B|SENP2|
INHBB|DHRS3|HOXC11|DGAT1|NCOA3|H6PD|
UBB|NGFR|ZNF467|UNG|NR3C2|UGDH|
ALDH3A2|TCF7L1|DPF1|TSC22D1|STK32B|
TSC22D2|TSC22D4|CENPB|NEFH|DHX16|
HS6ST1|TLX3|NFATC1|ALPK1|TBX4|WWTR1|
WNT2B|LEP|PAPOLA|LARGE|NEUROD2|ARSA

| | | | | | | | |
|---|---|---|---|---|---|---|---|
| 8152 | 9.0426E-5 | 4.2648E-3 | 128 | 8167 | 177 | 13949 | metabolism |

AOF2|RARRES2|CDX2|THRB|SLC6A3|PGD|
PKMYT1|DNAJB12|RFXAP|TCEAL1|NR2E1|
COX5B|CTNNB1|IDH3G|SMOX|HIRIP3|LOX|
FBXO22|IDUA|SGPL1|SNRPA1|ALDH6A1|IRS2|
HDAC11|SIX6|TNKS2|MAPK1|AQR|HIF1A|
CLPP|MAPK7|TRAF1|COASY|BBS4|CCBL1|
ERBB4|SOX3|OAS3|ST8SIA1|ATP6V1B2|
SOX9|PIN1|TCF21|PPAN|OAZ1|CRMP1|LHX3|
JUND|LHX6|SKIL|FBXO9|KLF6|CFLAR|ESRRA|
RAB8A|SAP18|OXSR1|NKX61|RPS7|DUSP26|
SLC25A10|SALL1|TSP50|H3F3A|FBXO31|
TNK2|BMP7|ZNF84|IMPA1|FOXA2|E2F5|
TBX21|CTCF|PTEN|TMF1|CCNE1|PCGF2|PAX8|
SOX18|ATP5O|HEMK1|MT3|PTGER1|ZFY|CHST2|
PRKCI|GTF2B|SENP2|INHBB|DHRS3|HOXC11|
DGAT1|NCOA3|H6PD|TXN|CYBRD1|UBB|NGFR|
ZNF467|UNG|NR3C2|UROS|UGDH|ALDH3A2|
TCF7L1|DPF1|TSC22D1|STK32B|TSC22D2|
TSC22D4|CENPB|NEFH|DHX16|HS6ST1|TLX3|
NFATC1|ALPK1|TBX4|FZD1|ATP1A1|RACGAP1|
WWTR1|WNT2B|LEP|PAPOLA|LARGE|NEUROD2|
ARSA

| | | | | | | | |
|---|---|---|---|---|---|---|---|
| 6351 | 9.1846E-5 | 4.2648E-3 | 49 | 2282 | 177 | 13949 | transcription, DNA-dependent |

ZNF84|AOF2|CDX2|THRB|FOXA2|E2F5|TBX21|
CTCF|NR2E1|TCEAL1|RFXAP|CTNNB1|TMF1|
CCNE1|PCGF2|PAX8|SOX18|ZFY|HDAC11|
SIX6|GTF2B|HIF1A|HOXC11|NCOA3|ZNF467|
SOX3|NR3C2|SOX9|TCF7L1|DPF1|TSC22D1|
TCF21|TSC22D2|TSC22D4|LHX3|JUND|LHX6|
SKIL|TLX3|NFATC1|KLF6|ESRRA|RAB8A|TBX4|
SAP18|WWTR1|NKX61|SALL1|NEUROD2

| | | | | | | | |
|---|---|---|---|---|---|---|---|
| 19222 | 9.4048E-5 | 4.2648E-3 | 55 | 2674 | 177 | 13949 | regulation of metabolism |

ZNF84|AOF2|CDX2|THRB|FOXA2|E2F5|SLC6A3|
TBX21|CTCF|TCEAL1|NR2E1|CTNNB1|TMF1|
CCNE1|PCGF2|PAX8|SOX18|ZFY|HDAC11|GTF2B|
SIX6|SENP2|INHBB|HIF1A|HOXC11|NCOA3|
BBS4|ZNF467|SOX3|NR3C2|SOX9|TCF7L1|
DPF1|TSC22D1|TCF21|TSC22D2|TSC22D4|
CENPB|LHX3|JUND|LHX6|TLX3|NFATC1|KLF6|
ESRRA|RAB8A|TBX4|SAP18|WWTR1|NKX6-1|
LEP|SALL1|NEUROD2|TNK2|BMP7

TABLE 5-continued

Cytoscape Bingo results on biological processes

| 32774 | 9.4965E-5 | 4.2648E-3 | 49 | 2285 | 177 | 13949 | RNA biosynthesis | ZNF84\|AOF2\|CDX2\|THRB\|FOXA2\|E2F5\|TBX21\|CTCF\|NR2E1\|TCEAL1\|RFXAP\|CTNNB1\|TMF1\|CCNE1\|PCGF2\|PAX8\|SOX18\|ZFY\|HDAC11\|SIX6\|GTF2B\|HIF1A\|HOXC11\|NCOA3\|ZNF467\|SOX3\|NR3C2\|SOX9\|TCF7L1\|DPF1\|TSC22D1\|TCF21\|TSC22D2\|TSC22D4\|LHX3\|JUND\|LHX6\|SKIL\|TLX3\|NFATC1\|KLF6\|ESRRA\|RAB8A\|TBX4\|SAP18\|WWTR1\|NKX61\|SALL1\|NEUROD2 |
|---|---|---|---|---|---|---|---|---|
| 45449 | 1.2700E-4 | 5.4554E-3 | 50 | 2376 | 177 | 13949 | regulation of transcription | ZNF84\|AOF2\|CDX2\|THRB\|FOXA2\|E2F5\|TBX21\|CTCF\|NR2E1\|TCEAL1\|CTNNB1\|TMF1\|CCNE1\|PCGF2\|PAX8\|SOX18\|ZFY\|HDAC11\|SIX6\|GTF2B\|SENP2\|HIF1A\|HOXC11\|NCOA3\|ZNF467\|SOX3\|NR3C2\|SOX9\|TCF7L1\|DPF1\|TSC22D1\|TCF21\|TSC22D2\|TSC22D4\|CENPB\|LHX3\|JUND\|LHX6\|TLX3\|NFATC1\|KLF6\|ESRRA\|RAB8A\|TBX4\|SAP18\|WWTR1\|NKX61\|SALL1\|NEUROD2\|BMP7 |
| 31323 | 1.4003E-4 | 5.7644E-3 | 53 | 2581 | 177 | 13949 | regulation of cellular metabolism | ZNF84\|AOF2\|CDX2\|THRB\|FOXA2\|E2F5\|SLC6A3\|TBX21\|CTCF\|TCEAL1\|NR2E1\|CTNNB1\|TMF1\|CCNE1\|PCGF2\|PAX8\|SOX18\|ZFY\|HDAC11\|GTF2B\|SIX6\|SENP2\|INHBB\|HIF1A\|HOXC11\|NCOA3\|ZNF467\|SOX3\|NR3C2\|SOX9\|TCF7L1\|DPF1\|TSC22D1\|TCF21\|TSC22D2\|TSC22D4\|CENPB\|LHX3\|JUND\|LHX6\|TLX3\|NFATC1\|KLF6\|ESRRA\|RAB8A\|TBX4\|SAP18\|WWTR1\|NKX6-1\|SALL1\|NEUROD2\|TNK2\|BMP7 |
| 6355 | 2.0665E-4 | 7.9112E-3 | 47 | 2228 | 177 | 13949 | regulation of transcription, DNA-dependent | ZNF84\|AOF2\|CDX2\|E2F5\|FOXA2\|ZNF467\|THRB\|TBX21\|SOX3\|NR3C2\|CTCF\|SOX9\|TCEAL1\|NR2E1\|TCF7L1\|DPF1\|TMF1\|CTNNB1\|TSC22D1\|CCNE1\|TCF21\|PCGF2\|TSC22D2\|TSC22D4\|PAX8\|JUND\|LHX3\|SOX18\|LHX6\|TLX3\|NFATC1\|KLF6\|RAB8A\|ESRRA\|ZFY\|TBX4\|SAP18\|HDAC11\|WWTR1\|GTF2B\|SIX6\|NKX6-1\|HOXC11\|HIF1A\|NCOA3\|SALL1\|NEUROD2 |
| 48518 | 2.0819E-4 | 7.9112E-3 | 27 | 1020 | 177 | 13949 | positive regulation of biological process | BBS4\|DRD1\|FOXA2\|ST8SIA1\|CTCF\|SOX9\|PTEN\|TCF7L1\|DPF1\|CTNNB1\|CCNE1\|GPC3\|PAX8\|CFLAR\|IRS2\|DGKQ\|TP53BP2\|WWTR1\|NKX6-1\|LEP\|INHBB\|MAPK1\|HIF1A\|NCOA3\|TNK2\|NGFR\|BMP7 |
| 19219 | 2.1659E-4 | 7.9256E-3 | 50 | 2427 | 177 | 13949 | regulation of nucleobase, nucleoside, nucleotide and nucleic acid metabolism | ZNF84\|AOF2\|CDX2\|THRB\|FOXA2\|E2F5\|TBX21\|CTCF\|NR2E1\|TCEAL1\|CTNNB1\|TMF1\|CCNE1\|PCGF2\|PAX8\|SOX18\|ZFY\|HDAC11\|SIX6\|GTF2B\|SENP2\|HIF1A\|HOXC11\|NCOA3\|ZNF467\|SOX3\|NR3C2\|SOX9\|TCF7L1\|DPF1\|TSC22D1\|TCF21\|TSC22D2\|TSC22D4\|CENPB\|LHX3\|JUND\|LHX6\|TLX3\|NFATC1\|KLF6\|ESRRA\|RAB8A\|TBX4\|SAP18\|WWTR1\|NKX6-1\|SALL1\|NEUROD2\|BMP7 |
| 45893 | 2.2725E-4 | 8.0185E-3 | 10 | 199 | 177 | 13949 | positive regulation of transcription DNA-dependent | CCNE1\|HIF1A\|NCOA3\|FOXA2\|PAX8\|CTCF\|SOX9\|WWTR1\|TCF7L1\|CTNNB1 |
| 51242 | 2.4821E-4 | 8.4563E-3 | 21 | 707 | 177 | 13949 | positive regulation of cellular physiology process | CFLAR\|BBS4\|IRS2\|FOXA2\|TP538P2\|ST8SIA1\|CTCF\|SOX9\|WWTR1\|PTEN\|TCF7L1\|DPF1\|CTNNB1\|MAPK1\|CCNE1\|HIF1A\|NCOA3\|PAX8\|NGFR\|TNK2\|BMP7 |
| 6366 | 2.8124E-4 | 9.2621E-3 | 19 | 611 | 177 | 13949 | transcription from RNA polymerase II promoter | CDX2\|FOXA2\|SAP18\|CTCF\|WWTR1\|SOX9\|RFXAP\|GTF2B\|TCEAL1\|TCF7L1\|TMF1\|CTNNB1\|TSC22D1\|HIF1A\|JUND\|NEUROD2\|SOX18\|SKIL\|NFATC1 |
| 7417 | 2.9997E-4 | 9.5603E-3 | 10 | 203 | 177 | 13949 | central nervous system development | IRS2\|SOX3\|PGD\|LHX6\|NGFR\|ZIC1\|TLX3\|PTEN\|ALDH3A2\|CTNNB1 |
| 45941 | 3.5051E-4 | 1.0822E-2 | 11 | 250 | 177 | 13949 | positive regulation of transcription | CCNE1\|HIF1A\|NCOA3\|FOXA2\|PAX8\|CTCF\|SOX9\|WWTR1\|BMP7\|TCF7L1\|CTNNBI |
| 16070 | 3.8419E-4 | 1.1502E-2 | 54 | 2751 | 177 | 13949 | RNA metabolism | ZNF84\|AOF2\|CDX2\|THRB\|FOXA2\|E2F5\|TBX21\|CTCF\|TCEAL1\|RFXAP\|NR2E1\|CTNNB1\|TMF1\|CCNE1\|PCGF2\|PAX8\|SOX18\|SNRPA1\|ZFY\|HDAC11\|GTF2B\|SIX6\|AQR\|HIF1A\|HOXC11\|NCOA3\|ZNF467\|SOX3\|NR3C2\|SOX9\|TCF7L1\|DPF1\|TSC22D1\|TCF21\|PPAN\|TSC22D2\|TSC22D4\|LHX3\|JUND\|DHX16\|LHX6\|SKIL\|TLX3\|NFATC1\|KLF6\|ESRRA\|RAB8A\|TBX4\|SAP18\|WWTR1\|NKX6-1\|PAPOLA\|SALL1\|NEUROD2 |
| 43119 | 4.2153E-4 | 1.2249E-2 | 22 | 789 | 177 | 13949 | positive regulation of physiological process | CFLAR\|BBS4\|IRS2\|FOXA2\|TP53BP2\|ST8SIA1\|CTCF\|SOX9\|WWTR1\|PTEN\|TCF7L1\|DPF1\|CTNNB1\|INHBB\|MAPK1\|CCNE1\|HIF1A\|NCOA3\|PAX8\|NGFR\|TNK2\|BMP7 |
| 45935 | 4.4277E-4 | 1.2499E-2 | 11 | 257 | 177 | 13949 | positive regulation of nuleobase, nuleoside, nucleotide and nucleic acid metabolism | CCNE1\|HIF1A\|NCOA3\|FOXA2\|PAX8\|CTCF\|SOX9\|WWTR1\|BMP7\|TCF7L1\|CTNNB1 |

TABLE 5-continued

Cytoscape Bingo results on biological processes

| | | | | | | | | |
|---|---|---|---|---|---|---|---|---|
| 35295 | 4.9531E−4 | 1.3594E−2 | 6 | 79 | 177 | 13949 | tube development | BBS4\|GPC3\|FOXA2\|TBX4\|BMP7\|CTNNB1 |
| 1822 | 5.6035E−4 | 1.4170E−2 | 4 | 30 | 177 | 13949 | kidney development | GPC3\|SALL1\|PAX8\|BMP7 |
| 35239 | 6.4502E−4 | 1.4171E−2 | 5 | 53 | 177 | 13949 | tube morphogenesis | BBS4\|GPC3\|FOXA2\|BMP7\|CTNNB1 |
| 16055 | 6.5204E−4 | 1.6518E−2 | 7 | 115 | 177 | 13949 | Wnt receptor signaling pathway | SENP2\|FZD8\|FZD10\|FZD1\|TCF7L1\|WNT2B\|CTNNB1 |
| 9987 | 6.9769E−4 | 1.7233E−2 | 172 | 12663 | 177 | 13949 | cellular process | KIFC1\|AOF2\|RARRES2\|CDX2\|TSPAN2\|THRB\|SLC6A3\|PGD\|PKMYT1\|DNAJB12\|ZIC1\|RFXAP\|TCEAL1\|NR2E1\|COX5B\|CTNNB1\|CDH22\|PTGIR\|IDH3G\|SLC25A24\|SMOX\|MCOLN1\|HIRIP3\|LOX\|FBXO22\|IDUA\|SGPL1\|SNRPA1\|ALDH6A1\|IRS2\|KCND2\|BAIAP3\|HDAC11\|HBXIP\|SIX6\|TNKS2\|BCAP31\|SSTR4\|RND3\|MAPK1\|HIF1A\|AQR\|CLPP\|MAPK7\|TRAF1\|BBS4\|COASY\|DRD1\|CCBL1\|ERBB4\|PCDH21\|SOX3\|ST8SIA1\|OAS3\|ATP6V1B2\|SOX9\|PXN\|PIN1\|KCNS3\|TCF21\|PPAN\|OAZ1\|CRMP1\|JUND\|LHX3\|LHX6\|SKIL\|FGD6\|FBXO9\|XPOT\|GABRD\|CFLAR\|GABARAPL2\|KLF6\|RAB8A\|ESRRA\|MK167\|TP53BP2\|8AP18\|CELSR3\|OXSR1\|NKX61\|RPS7\|DUSP26\|CNIH3\|SALL1\|SLC25A10\|TSP50\|FBXO31\|H3F3A\|TNK2\|BMP7\|ZNF84\|IMPA1\|E2F5\|FOXA2\|CLDN3\|TBX21\|CTCF\|AMN\|PTEN\|TMF1\|GPC4\|CCNE1\|PCGF2\|GPC3\|PAX8\|SOX18\|ATP5O\|HEMK1\|MT3\|PTGER1\|ZFY\|CHST2\|PRKCI\|TIMM23\|GTF2B\|MCTP1\|SENP2\|INHBB\|DHRS3\|DOK2\|HOXC11\|DGAT1\|NCOA3\|RIF1\|H6PD\|CCND2\|TXN\|CYBRD1\|UBB\|NGFR\|CNN3\|ZNF467\|UNG\|NR3C2\|UGDH\|UROS\|ALDH3A2\|TCF7L1\|DPF1\|HDGFRP3\|TSC2D1\|CDH8\|STK32B\|TSC22D2\|TSC22D4\|CENPB\|NEFH\|DHX16\|HS6ST1\|TLX3\|NFATC1\|FZD8\|ALPK1\|DGKQ\|TBX4\|FZD1\|ATP1A1\|RACGAP1\|WWTR1\|CABYR\|WNT2B\|LEP\|LSP1\|FZD10\|PAPOLA\|LARGE\|NEUROD2\|ARSA\|SLC15A3\|TOB1 |
| 44262 | 7.2493E−4 | 1.7469E−2 | 13 | 362 | 177 | 13949 | cellular carbohydrate metabolism | IRS2\|IMPA1\|PGD\|UGDH\|CHST2\|PTEN\|LEP\|IDH3G\|LARGE\|H6PD\|SLC25A10\|HS6ST1\|IDUA |
| 51094 | 7.6343E−4 | 1.7850E−2 | 5 | 57 | 177 | 13949 | positive regulation of development | LEP\|BBS4\|BMP7\|NKX6-1\|CTNNB1 |
| 19318 | 7.7686E−4 | 1.7850E−2 | 8 | 154 | 177 | 13949 | hexose metabolism | LEP\|IRS2\|IMPA1\|H6PD\|SLC25A10\|PGD\|UGDH\|PTEN |
| 31325 | 7.9668E−4 | 1.7889E−2 | 12 | 320 | 177 | 13949 | positive regulation of cellular metabolism | CCNE1\|HIF1A\|NCOA3\|FOXA2\|PAX8\|CTCF\|TNK2\|SOX9\|WWTR1\|BMP7\|TCF7L1\|CTNNB1 |
| | | | | | | | | GPC3\|FOXA2\|BMP7\|CTNNB1 |
| 1708 | 8.1688E−4 | 1.7935E−2 | 3 | 15 | 177 | 13949 | cell fate specification | SOX9\|TLX3\|CTNNB1 |
| 48754 | 8.6322E−4 | 1.8541E−2 | 4 | 34 | 177 | 13949 | branching morphogenesis of a tube | GPC3\|FOXA2\|BMP7\|CTNNB1 |
| 5996 | 9.5659E−4 | 1.9682E−2 | 8 | 159 | 177 | 13949 | monosaccharide metabolism | LEP\|IRS2\|IMPA1\|H6PD\|SLC25A10\|PGD\|UGDH\|PTEN |
| 1655 | 9.6504E−4 | 1.9682E−2 | 4 | 35 | 177 | 13949 | urogenital system development | GPC3\|SALL1\|PAX8\|BMP7 |
| 48762 | 9.9605E−4 | 1.9682E−2 | 3 | 15 | 177 | 13949 | mesenchymal cell differentiation | HIF1A\|SOX9\|NFATC1 |
| 10431 | 9.9605E−4 | 1.9682E−2 | 3 | 15 | 177 | 13949 | mesenchymal cell development | HIF1A\|SOX9\|NFATC1 |
| 51093 | 1.0414E−3 | 2.0123E−2 | 5 | 61 | 177 | 13949 | negative regulation of development | WWTR1\|NKX6-1\|MT3\|TOB1\|CTNNB1 |
| 43283 | 1.0768E−3 | 2.0123E−2 | 80 | 4724 | 177 | 13949 | biopolymer metabolism | ZNF84\|AOF2\|CDX2\|E2F5\|FOXA2\|THRB\|TBX21\|PKMYT1\|CTCF\|PTEN\|RFXAP\|TCEAL1\|NR2E1\|TMF1\|CTNNB1\|CCNE1\|PCGF2\|PAX8\|SOX18\|HIRIP3\|LOX\|FBXO22\|HEMK1\|PTGER1\|SNRPA1\|ZFY\|PRKCI\|HDAC11\|GTF2B\|SIX6\|TNKS2\|SENP2\|MAPK1\|HOXC11\|AQR\|HIF1A\|NCOA3\|UBB\|MAPK7\|ERBB4\|ZNF467\|UNG\|SOX3\|NR3C2\|ST8SIA1\|SOX9\|TCF7L1\|DPF1\|TSC22D1\|TCF21\|PPAN\|STK32B\|TSC22D2\|TSC22D4\|JUND\|LHX3\|NEFH\|DHX16\|LHX6\|SKIL\|TLX3\|FBXO9\|NFATC1\|KLF6\|ALPK1\|RAB8A\|ESRRA\|TBX4\|SAP18\|OXSR1\|WWTR1\|NKX61\|PAPOLA\|DUSP26\|LARGE\|SALL1\|NEUROD2\|FBXO31\|H3F3A\|TNK2 |
| 50793 | 1.0795E−3 | 2.0123E−2 | 8 | 162 | 177 | 13949 | regulation of development | LEP\|BBS4\|WWTR1\|BMP7\|NK6-1\|MT3\|TOB1\|CTNNB1 |
| 45597 | 1.1935E−3 | 2.1270E−2 | | 37 | 177 | 13949 | positive regulation of cell differentiation | LEP\|BMP7\|NKX6-1\|CTNNB1 |
| 1763 | 1.1935E−3 | 2.1207E−2 | 4 | 37 | 177 | 13949 | morphogenesis of a branching structure | GPC3\|FOXA2\|BMP7\|CTNNB1 |
| 2009 | 1.2056E−3 | 2.1270E−2 | 5 | 63 | 177 | 13949 | morphogenesis of an epithelium | BBS4\|FOXA2\|TBX4\|FZD1\|CTNNB1 |
| 7507 | 1.3110E−3 | 2.2724E−2 | 6 | 95 | 177 | 13949 | heart development | HIF1A\|ERBB4\|SOX9\|PTEN\|NFATC1\|CTNNB1 |
| 9893 | 1.3760E−3 | 2.3439E−2 | 12 | 341 | 177 | 13949 | positive regulation of metabolism | CCNE1\|HIF1A\|NCOA3\|FOXA2\|PAX8\|CTCF\|TNK2\|SOX9\|WWTR1\|BMP7\|TCF7L1\|CTNNB1 |
| 1649 | 1.4246E−3 | 2.3855E−2 | 3 | 18 | 177 | 13949 | osteoblast differentiation | WWTR1\|TOB1\|CTNNB1 |
| 1837 | 1.5613E−3 | 2.5710E−2 | 2 | 5 | 177 | 13949 | epithelial to mesenchymal transition | SOX9\|NFATC1 |

TABLE 5-continued

Cytoscape Bingo results on biological processes

| | | | | | | | | |
|---|---|---|---|---|---|---|---|---|
| 45165 | 1.9932E−3 | 3.1312E−2 | 5 | 70 | 177 | 13949 | cell fate commitment | ERBB4\|SALL1\|SOX9\|TLX3\|CTNNB1 |
| 30509 | 2.5902E−3 | 4.1277E−2 | 3 | 22 | 177 | 13949 | BMP signaling pathway | GPC3\|BMP7\|TOB1 |
| 6006 | 2.7650E−3 | 4.3363E−2 | 6 | 110 | 177 | 13949 | glucose metabolism | LEP\|IRS2\|H6PD\|SLC25A10\|PGD\|UGDH |
| 48468 | 2.8342E−3 | 4.3754E−2 | 12 | 372 | 177 | 13949 | cell development | BBS4\|HIF1A\|FBXO31\|NGFR\|RACGAP1\|SOX9\|TLX3\|BMP7\|NKX6-1\|NFATC1\|MT3\|CTNNBI |
| 31032 | 3.2244E−3 | 4.8268E−2 | 2 | 7 | 177 | 13949 | actomyosin structure organization and biogenesis | CNN3\|RACGAP1 |
| 6020 | 3.2244E−3 | 4.8268E−2 | 2 | 7 | 177 | 13949 | myo-inositol metabolism | IMPA1\|PTEN |
| 7420 | 3.3031E−3 | 4.8552E−2 | 6 | 114 | 177 | 13949 | brain development | IRS2\|SOX3\|PGD\|LHX6\|ZIC1\|CTNNB1 |
| 1656 | 3.3416E−3 | 4.8552E−2 | 3 | 24 | 177 | 13949 | metanephros development | GPC3\|SALL1\|PAX8 |
| 43170 | 3.4271E−3 | 4.9072E−2 | 100 | 6435 | 177 | 13949 | macromolecule metabolism | AOF2\|CDX2\|THRB\|PGD\|PKMYT1\|DNAJB12\|NR2E1\|TCEAL1\|RFXAP\|CTNNB1\|IDH3G\|HIRIP3\|LOX\|FBXO22\|IDUA\|SNRPA1\|IRS2\|HDAC11\|SIX6\|TNKS2\|MAPK1\|AQR\|HIF1A\|CLPP\|MAPK7\|TRAF1\|ERBB4\|SOX3\|ST8SIA1\|SOX9\|PIN1\|PPAN\|TCF21\|LHX3\|JUND\|LHX6\|SKIL\|FBXO9\|KLF6\|CFLAR\|ESRRA\|RAB8A\|SAP18\|OXSR1\|NKX61\|RPS7\|DUSP26\|SLC25A10\|SALL1\|TSP50\|H3F3A\|FBXO31\|TNK2\|ZNF84\|IMPA1\|FOXA2\|E2F5\|TBX21\|CTCF\|PTEN\|TMF1\|CCNE1\|PCGF2\|PAX8\|SOX18\|HEMK1\|PTGER1\|ZFY\|PRKCI\|CHST2\|GTF2B\|SENP2\|INHBB\|HOXC11\|NCOA3\|H6PD\|UBB\|ZNF467\|UNG\|UGDH\|NR3C2\|TCF7L1\|DPF1\|TSC22D1\|STK32B\|TSC22D2\|TSC22D4\|DHX16\|NEFH\|HS6ST1\|TLX3\|NFATC1\|ALPK1\|TBX4\|WWTR1\|WNT2B\|LEP\|PAPOLA\|LARGE\|NEUROD2 |

CENTRICITY

File created with BiNGO (c)
ontology: function
curator: GO
Selected ontology file: jar:file:C:\Program Files\Cytoscape_v2.7.0\plugins\GOlorize2-4.jar!/GO_Molecular_Function
Selected annotation file: jar:file:C:\Program File\Cytoscape_v2.7.0\plugins\GOlorize2-4.jar!/H_sapiens_default
Discarded evidence codes:
Overrepresentation
Selected statistical test: Hypergeometric test
Selected correction: Benjamini & Hochberg False Discovery Rate (FDR) correction
Selected significance level: 0.05
Testing option: Test cluster versus whole annotation
The selected cluster:
GPC4 BBS4 RAB8A ZCCHC11 HOXC11 NCDN CYBRD1 HIRIP3 TCEAL1
No annotations were retrieved for the following entities:
ZCCHC11 NCDN

| GO-ID | p-value | corr p-value | x | n | X | N | Description | Genes in test set |
|---|---|---|---|---|---|---|---|---|
| 30092 | 5.0154E−4 | 3.0594E−2 | 1 | 1 | 7 | 13957 | regulation of flagellum biogenesis | BBS4 |
| 45724 | 5.0154E−4 | 3.0594E−2 | 1 | 1 | 7 | 13957 | positive regulation of flagellum biogenesis | BBS4 |
| 1895 | 1.0029E−4 | 4.0783E−2 | 1 | 2 | 7 | 13957 | retinal homeostasis | BBS4 |
| 35058 | 1.5040E−4 | 4.5871E−2 | 1 | 3 | 7 | 13957 | sensory cilium biogenesis | BBS4 |

CLOSENESS

File created with BiNGO (c)
ontology: process
curator: GO
Selected ontology file: jar:file:C:\Program Files\Cytoscape_v2.7.0\plugins\GOlorize2-4.jar!/GO_Biological_Process
Selected annotation file: jar:file:C:\Program Files\Cytoscape_v2.7.0\plugins\GOlorize2-4.jar!/H_sapiens_default
Discarded evidence codes:
Overrepresentation
Selected statistical test: Hypergeometric test
Seleceted correction: Benjamini & Hochberg False Discovery Rate (FDR) correction
Selected significance level: 0.05
Testing option: Test cluster versus whole annotation
The selected cluster:
TRAF1 TSPAN2 ST8SIA1 PKMYT1 CTNNB1 PIN1 JUND HIRIP3 SMOX TLX3 XPOT SNRPA1 ESRRA RAB8A
IRS2 KCND2 FZD1 TNKS2 LSP1 LEP
RPAP1 FZD10 DHRS3 TXN CYBRD1 NGFR
No annotations were retrieved for the following entities:
RPAP1

TABLE 5-continued

Cytoscape Bingo results on biological processes

| GO-ID | p-value | corr p-value | x | n | X | N | Description | Genes in test set |
|---|---|---|---|---|---|---|---|---|
| 1708 | 3.1894E-4 | 3.0921E-2 | 2 | 15 | 25 | 13955 | cell fate specification | TLX3\|CTNNB1 |
| 6928 | 4.0068E-4 | 3.0921E-2 | 5 | 363 | 25 | 13955 | cell motility | LSP1\|TSPAN2\|TXN\|NGFR\|TLX3 |
| 51674 | 4.0068E-4 | 3.0921E-2 | 5 | 363 | 25 | 13955 | localization of cell | LSP1\|TSPAN2\|TXN\|NGFR\|TLX3 |
| 40011 | 4.2134E-4 | 3.0921E-2 | 5 | 367 | 25 | 13955 | locomotion | LSP1\|TSPAN2\|TXN\|NGFR\|TLX3 |
| 7417 | 4.5742E-4 | 3.0921E-2 | 4 | 206 | 25 | 13955 | central nervous system development | IRS2\|NGFR\|TLX3\|CTNNB1 |

ECCENTRICITY

File created with BiNGO (c)
ontology: process
curator: GO
Selected ontology file: jar:file:C:\Program Files\Cytoscape_v2.7.0\plugins\GOlorize2-4.jar!/GO_Molecular_Function
Selected annotation file: jar:file:C:\Program File\Cytoscape_v2.7.0\plugins\GOlorize2-4.jar!/H_sapiens_default
Discarded evidence codes:
Overrepresentation
Selected statistical test: Hypergeometric test
Selected correction: Benjamini & Hochberg False Discovery Rate (FDR) correction
Selected significance level: 0.05
Testing option: Test cluster versus whole annotation
The selected cluster:
BBS4 CPLAR AOF2
No annotations were retrieved for the following entities:

| GO-ID | p-value | corr p-value | x | n | X | N | Description | Genes in test set |
|---|---|---|---|---|---|---|---|---|
| 30092 | 2.1495E-4 | 1.3649E-2 | 1 | 1 | 3 | 13957 | regulation of flagellum biogenesis | BBS4 |
| 45724 | 2.1495E-4 | 1.3649E-2 | 1 | 1 | 3 | 13957 | positive regulation of flagellum biogenesis | BBS4 |
| 1895 | 4.2986E-4 | 1.8197E-2 | 1 | 2 | 3 | 13957 | retinal homeostasis | BBS4 |
| 35058 | 6.4475E-4 | 2.0471E-2 | 1 | 3 | 3 | 13957 | sensory cilium biogenesis | BBS4 |
| 9296 | 1.0744E-3 | 2.3390E-2 | 1 | 5 | 3 | 13957 | flagellum biogenesis | BBS4 |
| 42384 | 1.2892E-3 | 2.3390E-2 | 1 | 6 | 3 | 13957 | cillium biogenesis | BBS4 |
| 43064 | 1.2892E-3 | 2.3390E-2 | 1 | 6 | 3 | 13957 | flagellum organization and biogenesis | BBS4 |
| 31344 | 1.5040E-3 | 2.3876E-2 | 1 | 7 | 3 | 13957 | regulation of cell projection organization and biogenesis | BBS4 |
| 51130 | 1.9334E-3 | 2.7282E-2 | 1 | 9 | 3 | 13957 | positive regulation of cell organization and biogenesis | BBS4 |
| 1843 | 3.0064E-3 | 3.0673E-2 | 1 | 14 | 3 | 13957 | neural tube closure | BBS4 |
| 14020 | 3.0064E-3 | 3.0673E-2 | 1 | 14 | 3 | 13957 | primary neural tube formation | BBS4 |
| 1679 | 3.6499E-3 | 3.0673E-2 | 1 | 17 | 3 | 13957 | neural tube formation | BBS4 |
| 1838 | 3.8643E-3 | 3.0673E-2 | 1 | 18 | 3 | 13957 | embryonic epithelial tube formation | BBS4 |
| 1839 | 3.8643E-3 | 3.0673E-2 | 1 | 18 | 3 | 13957 | neural plate morphogenesis | BBS4 |
| 16358 | 3.8643E-3 | 3.0673E-2 | 1 | 18 | 3 | 13957 | dendrite development | BBS4 |
| 21915 | 3.8643E-3 | 3.0673E-2 | 1 | 18 | 3 | 13957 | neural tube development | BBS4 |
| 1894 | 4.2931E-3 | 3.2072E-2 | 1 | 20 | 3 | 13957 | tissue homeostasis | BBS4 |
| 16331 | 5.1502E-3 | 3.4064E-2 | 1 | 24 | 3 | 13957 | morphogenesis of embryonic epithelium | BBS4 |
| 19216 | 5.3644E-3 | 3.4064E-2 | 1 | 25 | 3 | 13957 | regulation of lipid metabolism | BBS4 |
| 30534 | 5.3644E-3 | 3.4064E-2 | 1 | 25 | 3 | 13957 | adult behavior | BBS4 |
| 51242 | 7.4287E-3 | 4.4926E-2 | 2 | 707 | 3 | 13957 | positive regulation of cellular physiological process | CFLAR\|BBS4 |
| 30031 | 7.9325E-3 | 4.4982E-2 | 1 | 37 | 3 | 13957 | cell projection biogenesis | BBS4 |
| 8624 | 8.1463E-3 | 4.4982E-2 | 1 | 38 | 3 | 13957 | induction of apoptosis by extracellular signals | CFLAR |
| 43119 | 9.2157E-3 | 4.8766E-2 | 2 | 789 | 3 | 13957 | positve regulation of physiological process | CFLAR\|BBS4 |

According to the results presented in Tables 4 and 5, above the following genes were identified as highlighted, i.e. very relevant:

1) Molecular Function: (cytoscape bingo MF corr 0.55.docx; Table 4)

ALL (a special case of the analysis where all nodes with highly (anti) correlated edges are selected regardless of their network metrics values). In this group a large number of genes is highlighted, corresponding to the detection of overrepresentation of transcription regulation and DNA binding functions (see Table 4, "All").

CENTRICITY. In this group the genes CYBRD1, HOXC11, and TCEAL1 are highlighted.

CLOSENESS. In this group the genes FZD10 and FZD1 are highlighted.

HIGHCONN. In this group a large number of genes is highlighted, corresponding to the detection of overrepresentation of transcription activation, repression and receptor binding.

2) Biological Process: (cytoscape bingo BP con 0.55.docx; Table 5)

ALL (a special case of the analysis where all nodes with highly (anti) correlated edges are selected regardless of their network metrics values). In this group a large number of genes is highlighted, corresponding to the detection of overrepresentation of regulatory and developmental processes (see Table 5, "All").

CENTRICITY. In this group gene BBS4 is highlighted.

CLOSENESS. In this group genes CTNNB1, IRS2, LSP1, NGFR, TLX3, TSPAN2, TXN are highlighted, corresponding to the detection of overrepresentation of cell motility localization, and fate.

ECCENTRICITY. In this group genes CFLAR and BBS4 are highlighted, corresponding to the detection of overrepresentation of regulation of biogenesis.

The invention claimed is:

1. A method for identifying and treating a patient responsive to cancer therapy comprising:
   receiving a primary dataset comprising data on at least one stratifying biomedical marker and/or a network node, the primary dataset being associated with a healthy subject;
   receiving a secondary dataset comprising data on at least one stratifying biomedical marker and/or a network node, the secondary dataset being associated with a subject affected by a medical condition which may be treatable by cancer therapy;
   comparing said primary dataset with said secondary dataset and/or with external datasets to generate a significance value for said stratifying biomedical markers;
   identifying a network among the stratifying biomedical markers with other members of the network based on the significance value supplemented with a correction procedure;
   ranking members of the identified network according to a ranking score based upon a reference network metric to identify network nodes and/or high ranking network members associated with the medical condition of the secondary subject;
   determining potential responsiveness of the patient to cancer therapy based on the association between the identified network nodes and/or high ranking network members and the stratifying biomedical markers;
   selecting and treating patients with a cancer therapy based on the identified high ranking network members and the stratifying biomedical markers.

2. The method of claim 1, wherein said network metric comprises at least one element selected from the group of connectivity, adjacency, network density, network centralization, network heterogeneity, cliquishness, hub gene significance, network significance, centroid significance, centroid conformity, betweenness, centricity, closeness and eccentricity.

3. The method of claim 1, wherein said biomedical marker is a gene, a genomic locus in a coding region, a genomic locus in a non-coding region, a transcript and/or a protein.

4. The method of claim 1, wherein said medical condition is ovarian cancer.

5. The method of claim 1, wherein the cancer therapy is chemotherapy.

6. The method of claim 5, wherein said predictive value is the indication of likelihood of responsiveness of a subject to a therapy comprising one or more platinum based drugs.

7. The method of claim 1, wherein the chemotherapy comprises one or more platinum based drugs.

8. The method of claim 7, wherein the platinum based drug is carboplatinum.

9. The method of claim 1, wherein the primary dataset comprises data on methylated loci and gene expression of the at least one stratifying biomedical marker and/or a network node.

10. The method of claim 1, wherein the secondary dataset comprises data on methylated loci and gene expression of the at least one stratifying biomedical marker and/or a network node.

* * * * *